United States Patent
Lorberboum-Galski et al.

(10) Patent No.: US 10,287,331 B2
(45) Date of Patent: May 14, 2019

(54) MITOCHONDRIAL PROTEINS CONSTRUCTS AND USES THEREOF

(71) Applicant: Yissum Research Development Company of the Hebrew University of Jerusalem Ltd, Jerusalem (IL)

(72) Inventors: Haya Lorberboum-Galski, Jerusalem (IL); Hagar Greif, Ness Ziona (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 0 days.

(21) Appl. No.: 14/784,253

(22) PCT Filed: Apr. 10, 2014

(86) PCT No.: PCT/IL2014/050354
§ 371 (c)(1),
(2) Date: Oct. 13, 2015

(87) PCT Pub. No.: WO2014/170896
PCT Pub. Date: Oct. 23, 2014

(65) Prior Publication Data
US 2016/0075745 A1    Mar. 17, 2016

Related U.S. Application Data

(63) Continuation-in-part of application No. 14/034,224, filed on Sep. 23, 2013, now Pat. No. 8,912,147.

(60) Provisional application No. 61/811,934, filed on Apr. 15, 2013, provisional application No. 61/869,981, filed on Aug. 26, 2013.

(51) Int. Cl.
| | |
|---|---|
| *A61K 38/45* | (2006.01) |
| *C07K 19/00* | (2006.01) |
| *C07K 14/16* | (2006.01) |
| *C07K 14/47* | (2006.01) |
| *C12N 9/10* | (2006.01) |
| *C07K 14/435* | (2006.01) |
| *A61K 9/00* | (2006.01) |
| *C07K 14/005* | (2006.01) |
| *A61K 38/00* | (2006.01) |

(52) U.S. Cl.
CPC .......... *C07K 14/435* (2013.01); *A61K 9/0019* (2013.01); *C07K 14/005* (2013.01); *C07K 14/47* (2013.01); *C12N 9/1018* (2013.01); *A61K 38/00* (2013.01); *C07K 2319/07* (2013.01); *C07K 2319/10* (2013.01); *C07K 2319/21* (2013.01); *C12N 2740/16033* (2013.01); *C12Y 108/01004* (2013.01); *C12Y 203/03001* (2013.01); *Y10S 530/826* (2013.01); *Y10S 530/827* (2013.01)

(58) Field of Classification Search
None
See application file for complete search history.

(56) References Cited

U.S. PATENT DOCUMENTS

| | | |
|---|---|---|
| 7,101,844 B2 | 9/2006 | Kim et al. |
| 7,405,284 B2 | 7/2008 | Guy |
| 8,003,609 B2 | 8/2011 | Salter et al. |
| 8,158,749 B2 | 4/2012 | Salter et al. |
| 8,278,428 B2 | 10/2012 | Guy et al. |
| 8,283,444 B2 | 10/2012 | Payne |
| 8,466,140 B2 | 6/2013 | Altieri et al. |
| 8,729,021 B2 | 5/2014 | Kwon et al. |
| 8,735,341 B2 | 5/2014 | Payne |
| 8,859,500 B2 | 10/2014 | Salter et al. |
| 8,865,160 B2 | 10/2014 | Wilson et al. |
| 9,017,999 B2 | 4/2015 | Corral-Debrinski et al. |
| 9,045,552 B2 | 6/2015 | Payne |
| 9,139,628 B2 | 9/2015 | Minczuk et al. |
| 2005/0147993 A1* | 7/2005 | Khan .................. A61K 48/005 435/6.17 |
| 2005/0169904 A1 | 8/2005 | Payne |
| 2006/0211647 A1 | 9/2006 | Khan |
| 2007/0196334 A1 | 8/2007 | Khan |
| 2010/0222263 A1 | 9/2010 | Ma et al. |
| 2011/0177051 A1* | 7/2011 | Galski-Lorberboum .................... C12Y 108/01004 424/94.3 |
| 2011/0190224 A1* | 8/2011 | Payne .............. A61K 47/48246 514/21.2 |
| 2014/0135275 A1 | 5/2014 | Keefe et al. |
| 2014/0142121 A1 | 5/2014 | Altieri et al. |
| 2015/0011611 A1 | 1/2015 | Kim et al. |
| 2015/0118217 A1 | 4/2015 | Wilson et al. |

(Continued)

FOREIGN PATENT DOCUMENTS

| | | |
|---|---|---|
| EP | 2891661 A1 | 7/2015 |
| WO | WO 2003/097671 A1 | 11/2003 |

(Continued)

OTHER PUBLICATIONS

Calvo et al., The Mitochondrial Proteome and Human Disease, Annu. Rev. Genomics Hem. Genet., 2010, 11, 25-44.*
Uniprot, Accession No. P40926, 2013, www.uniprot.org.*
Uniprot, Accession No. P09622, 2013, www.uniprot.org.*
Prieve et al., Targeted mRNA therapy for ornithine transcarbamylase deficiency, Molecular Therapy, 2018, accepted manuscript, doi: 10.1016/j.ymthe.2017.12.024.*
Angdisen et al., "Mitochondrial Trifunctional Protein Defects: Molecular Basis and Novel Therapeutic Approaches", Current Drug Targets—Immune Endocrine & Metabolic Disorders, pp. 27-40 (2005).

(Continued)

*Primary Examiner* — Robert B Mondesi
*Assistant Examiner* — Todd M Epstein
(74) *Attorney, Agent, or Firm* — Sheppard Mullin Richter & Hampton LLP

(57) ABSTRACT

Disclosed are fusion protein constructs comprising a functional mitochondrial protein, that can enter mitochondria within intact cells. Further disclosed are methods of treating mitochondrial disorders by the disclosed fusion proteins and compositions therefor.

7 Claims, 28 Drawing Sheets

Specification includes a Sequence Listing.

(56) References Cited

U.S. PATENT DOCUMENTS

| | | |
|---|---|---|
| 2015/0225740 A1 | 8/2015 | Corral-Debrinski et al. |
| 2015/0297742 A1 | 10/2015 | Strieker et al. |
| 2015/0361140 A1 | 12/2015 | Kim et al. |

FOREIGN PATENT DOCUMENTS

| | | | |
|---|---|---|---|
| WO | WO 2006/117250 A2 | 11/2006 | |
| WO | WO 2007/071962 A1 | 6/2007 | |
| WO | WO 2008/025130 A1 | 3/2008 | |
| WO | WO 2008/060776 A2 | 5/2008 | |
| WO | WO 2008/101233 A2 | 8/2008 | |
| WO | WO 2009/036092 A2 | 3/2009 | |
| WO | WO2009/098682 | 8/2009 | |
| WO | WO 2012/174452 A1 | 12/2012 | |
| WO | WO 2013/120086 A1 | 8/2013 | |
| WO | WO 2014/086835 A1 | 6/2014 | |

OTHER PUBLICATIONS

Backman et el., "Lack of correlation between in vitro and in vivo studies on the effects of tangeretin and tangerine juice on midazolam hydroxylation," Clin Pharmacal Ther, 67(4): 382-90 (2000).
Bencze et al. "The Structure and Function of Frataxin." Grit. Rev. Biochem. Mol. Biol.41.5:269-291 (2006).
Berger et el., "Lipoamide Dehydrogenase Activity in Lymphocytes", Elsevier, Clinica Chimica Acta 256 pp. 197-201 (1996).
Bourgeron et al., "Isolation and Characterization of Mitochondria from Human B Lymphoblastoid Cell Lines", Biochemical and Biophysical Research Communications, vol. 186, No. 1, pp. 16-23 (1992).
Brady, R. O. et al., "Enzyme-replacement therapy for metabolic storage disorders," Lancet Neurol., 3(12):752-756 (2004).
Braun, H. P. et el., "The mitochondrial processing peptidase," Int. J. Biochem. Cell Biol., 29:1043-1045 (1997).
Brautigam, C. A. et al., "Crystal structure of human dihydrolipoamide dehydrogenase: NAD+/NADH binding and the structural basis of disease-causing mutations," J. Mol. Biol., 350(3):543-552 (2005).
Bulteau, A. L. et al., "Frataxin acts as an iron chaperone protein to modulate mitochondrial aconitase activity," Science, 305(5681):242-245 (2004).
Campuzano, V. et al., "Frataxin is reduced in Friedreich ataxia patients and is associated with mitochondrial membranes," Hum. Mol. Genet., 6(11):1771-1780 (1997).
Cavadini, P. et al., "Two-step processing of human frataxin by mitochondrial processing peptidase. Precursor and intermediate forms are cleaved at different rates," J. Biol. Chem., 275(52):41469-41475 (2000).
Cheng, T. L. et al., "Identification and characterization of the mitochondrial targeting sequence and mechanism in human citrate synthase," J. Cell. Biochem., 107(5):1002-1015 (2009).
Chinnery, P. F. et al., "Mitochondria," J. Neurol. Neurosurg. Psychiatry, 74:1188-1199 (2003).
COX6B1; OMIM:124089 (Sep. 24, 1991).
COX1O; OMIM:602125 (Nov. 17, 1997).
Cossee et al., "Friedreich's Ataxia: Point Mutations and Clinical Presentation of Compound Heterozygotes", Annals of Neurology, 45(2): 200-206 (1999).
Del Gaizo et al., "A Novel TAT-Mitochondrial Signal Sequence Fusion Protein is Processed, Stays in Mitochondria, and Crosses the Placenta", Molecular Therapy, vol. 7, No. 6, pp. 720-730 (2003).
Delatycki, M. B. et al., "Direct evidence that mitochondrial iron accumulation occurs in Friedreich ataxia," Ann. Neurol., 45(5):673-675 (1999).
Desnick et el., "Fabry Disease: Clinical Spectrum and Evidence-based Enzyme Replacement Therapy", Department of Human Genetics, Mount Sinai School of Medicine of New York University, Fifth Avenue and 100th Street, New York, NY 10029, Abstract, (2006).
DiMauro, S. et el., "Mitochondrial respiratory-chain diseases," N. Engl. J. Med., 348(26):2656-2668 (2003).
Durr, A. et al., "Clinical and genetic abnormalities in patients with Friedreich's ataxia," N. Engl. J. Med., 335(16):1169-1175 (1996).
Elpeleg et al., "Lipoamide Dehydrogenase Deficiency: A new cause for Recurrent Myoglobinuria", Short Report, Muscle & Nerve, February, pp. 238-240 (1997).
FASTKD2; OMIM:612322 (Sep. 26, 2008).
Frankel, A. D. et al., "Cellular uptake of the tat protein from human immunodeficiency virus," Cell, 55(6):1189-1193 (1988).
Futaki, S. et al., "Arginine-rich peptides. An abundant source of membrane-permeable peptides having potential as carriers for intracellular protein delivery," J. Biol. Chem., 276(8):5836-5840 (2001).
Gakh, O. et al., "Mitochondrial processing peptidases," Biochim. Biophys. Acta, 1592(1):63-77 (2002).
Gakh, O. et al., "Normal and Friedreich ataxia cells express different isoforms of frataxin with complementary roles in iron-sulfur cluster assembly," J. Biol. Chem., 285(49):38486-38501 (2010).
Gavel, Y. et al., "Cleavage-site motifs in mitochondrial targeting peptides," Protein Eng., 4(1):33-37 (1990).
GenBank, Accession No. NM_000144.4, 2011, www.ncbi.nlm.nih.gov.
George et al., "An analysis of protein domain linkers: their classification and role in protein folding", Protein Eng., 15, 871-79 (2003).
Green, M. et al.,"Autonomous functional domains of chemically synthesized human immunodeficiency virus tat trans-activator protein," Cell, 55(6):1179-1188 (1988).
Guo, X. et al., "Transduction of functionally active TAT fusion proteins into cornea," Exp. Eye Res., 78(5):997-1005 (2004).
Harding, A. E., "Friedreich's ataxia: a clinical and genetic study of 90 families with an analysis of early diagnostic criteria and intrafamilial clustering of clinical features," Brain, 104:589-620 (1981).
Horwich, A., "Protein import into mitochondria and peroxisomes," Curr. Opin. Cell Biol., 2:625-633 (1990).
Horwich et al. "The Ornithine Transcarbamylase Leader Peptide Directs Mitochondrial Import through Both Its Mid portion Structure and Net Positive Charge", J. Cell Biol., 105:669-677 (1987).
Howell et al., "Leber Hereditary Optic Neuropathy: Involvement of the Mitochondrial NDI Gene and Evidence for an Intragenic Suppressor Mutation", Am. J. Hum. Genet., 48:935-942 (1991).
Kabouridis, P. S., "Biological applications of protein transduction technology," Trends Biotechnol., 21(11):498-503 (2003).
Khan et al., "Development of Mitochondrial Gene Replacement Therapy", Journal of Bioenergetics and Biomembranes, vol. 36, No. 4, pp. 387-393 (2004).
Kuppuswamy et al, "Multiple Functional Domains of Tat, the Trans-Activator of HIV-1, Defined by Mutational Analysis", IRL Press, vol. 17, No. 9, pp. 3551-3561 (1989).
Liu et al., "Identification of two missense mutations in a dihydrolipoamide dehydrogenase-deficient patient", 90:5186-5190 (1993).
Lodi, R. et al., "Deficit of in vivo mitochondrial ATP production in patients with Friedreich ataxia," Proc. Natl. Acad. Sci. USA, 96(20):11492-11495 (1999).
Luft, F. C., "Transducing proteins to manipulate intracellular targets," J Mol. Med. (Berl), 81(9):521-523 (2003).
Maddalena et al., "Characterization of Point Mutations in the Same Arginine Codon in Three Unrelated Patients with Ornithine Transcarbamylase Deficiency", J. Clin. Invest, 82:1353-1358 (1988).
MTCO1; OMIM:516030 (Mar. 2, 1993).
MTCO2; OMIM:516040 (Mar. 2, 1993).
MTCO3; OMIM:516050 (Mar. 2, 1993).
NCBI Protein Database Accession No. P08559; OMIM:312170 (Aug. 1, 1988).
NCBI Protein Database Accession No. P11177; OMIM:208800 (Jul. 1, 1989).
NCBI Protein Database Accession No. P11310; OMIM:201450 (Jul. 1, 1989).
NCBI Protein Database Accession No. P12694; OMIM:248600 (Oct. 1, 1989).
NCBI Protein Database Accession No. P21953 (Aug. 1, 1991).
NCBI Protein Database Accession No. P40939; OMIM:609015 (Feb. 1, 1995).

(56) References Cited

OTHER PUBLICATIONS

NCBI Protein Database Accession No. P49748; OMIM:201475 (Oct. 1, 1996).
NCBI Protein Database Accession No. P55084 (Oct. 1, 1996).
NCBI Protein Database Accession No. Q16595 (Jul. 15, 1999).
NDUFV1; OMIM:161015 (Jan. 14, 1993).
NDUFS1; OMIM:157655 (Jul. 1, 1993).
NDUFV2; OMIM:600532 (May 17, 1995).
NDUFS7; OMIM:601825 (May 23, 1997).
NDUFS8; OMIM:602141 (Dec. 2, 1997).
NDUFA2; OMIM:602137 (Dec. 2, 1997).
NDUFS4; OMIM:602694 (Jun. 8, 1998).
NDUFS2; OMIM:602985 (Aug. 19, 1998).
NDUFS3; OMIM:603846 (May 25, 1999).
NDUFS6; OMIM:603848 (May 25, 1999).
OMIM:220110 (Jun. 3, 1986).
OMIM:124000 (Jun. 4, 1986).
OMIM:252010 (Sep. 30, 1987).
OMIM:252011 (Dec. 9, 1989).
OMIM:604273 (Nov. 1, 1999).
Perlman, S. L., "A review of Friedreich ataxia clinical trial results," J. Child. Neurol., 27(9):1217-1222 (2012).
Rapoport, M. et al., "TAT-mediated delivery of LAD restores pyruvate dehydrogenase complex activity in the mitochondria of patients with LAD deficiency," Mol. Ther., 16(4):691-697 (2008).
Rapoport, M. et al., "Successful TAT-mediated enzyme replacement therapy in a mouse model of mitochondrial E3 deficiency," J. Mol. Med. (Bed), 89(2):161-170 (2011).
Rapoport et al., "Enzyme replacement therapy for mitochondrial disorders—the lipoamide dehydrogenase deficiency as a model," J Inherit Metab Dis 29 (Suppl 1), p. 15. Abstract No. WS-2-3 (2006).
Richardson, T. E. et al., "Estrogen prevents oxidative damage to the mitochondria in Friedreich's ataxia skin fibroblasts," PLoS One, 7(4):e34600 (2012).
Robinson et al. "Identification of Canine Model of Pyruvate Dehydrogenase Phosphate 1 Deficiency", J Inherit Metab Dis, 29 (Suppl) p. 15 (2006).
Rotig, A. et al., "Aconitase and mitochondrial iron-sulphur protein deficiency in Friedreich ataxia," Nat. Genet., 17(2):215-217 (1997).
Saada, A. et al., "C6ORF66 is an assembly factor of mitochondrial complex I," Am. J. Hum. Genet., 82(1):32-38 (2008).
Saada et al., "ATP Synthesis in Lipoamide Dehydrogenase Deficiency", Biochemical and Biophysical Research Communications 269, (2000).
Santos, R. et al., "Friedreich ataxia: molecular mechanisms, redox considerations, and therapeutic opportunities," Antioxid. Redox Signal, 13(5):651-690 (2010).
Scarpa et al., "Mucopolysaccharidosis VI: the Italian Experience", Eur. J. Pediatr., vol. 168, pp. 1203-1206 (2009).
Schmucker, S. et al., "The in vivo mitochondrial two-step maturation of human frataxin," Hum. Mol. Genet., 17(22):3521-3531 (2008).
Schulz, J. B. et al., "Diagnosis and treatment of Friedreich ataxia: a European perspective," Nat. Rev. Neurol., 5:222-234 (2009).
Schwarze, S. R. et al., "In vivo protein transduction: delivery of a biologically active protein into the mouse," Science, 285(5433):1569-1572 (1999).
SCO1; OMIM:603644 (Mar. 15, 1999).
SCO2; OMIM:604272 (Nov. 1, 1999).
Shaag et al., "Molecular Basis of Upoamide Dehydrogenase Deficiency in Ashkenazi Jews", American Journal of Medical Genetics, vol. 82, pp. 177-182 (1999).
Sly, "Enzyme Replacement Therapy: from Concept to Clinical Practice", Acta Paediatr Suppl 439: pp. 71-78 (2002).
Toro et al., "TAT-Mediated Intracellular Delivery of Purine Nucleoside Phosphorylase Corrects its Deficiency in Mice", The Journal of Clinical Investigation, vol. 116, No. 10, pp. 2717-2726 (2006).
Tsou, A. Y. et al., "Pharmacotherapy for Friedreich ataxia," CNS Drugs, 23(3):213-223 (2009).
Tuchman et al. "The biochemical and molecular spectrum of ornithine transcarbamylase deficiency", J. Inher. Metab. Dis., 21 (Suppl 1):40-58 (1998).
Vettakkorumakankav et al., "Dihydrolipoamide Dehydrogenase: Structural and Mechanistic Aspects", Indian Journal of Biochemistry & Biophysics, vol. 33, Minireview, pp. 168-176 (1996).
Vyas, P. M. et al., "A TAT-frataxin fusion protein increases lifespan and cardiac function in a conditional Friedrich's ataxia mouse model," Hum. Mol. Genet., 21(6):1230-1247 (2012).
Vyas et al. "TAT Opens the Door", Mol. Ther, 16(4): 647-648, Apr. 2008.
Wang, D. et al., "Short-term, high dose enzyme replacement therapy in sialidosis mice," Mol. Genet. Metab., 85(3):181-189 (2005).
Yoon et el., "TAT-mediated delivery of human glutamate dehydrogenase into PC12 cells", Neurochemistry Int., 41, 37-42 (2002).
Del Gaizo et al "Targeting proteins to mitochondria using TAT", *Molecular Genetics and Metabolism*, vol. 80, No. 1-2, Sep. 1, 2003.
Koczor et al "Mitochondrial DNA Damage Initiates a Cell Cycle Arrest by a Chk2-associated Mechanism in Mammalian Cells", *Journal of Biological Chemistry*, vol. 284, No. 52, Oct. 19, 2009.

* cited by examiner

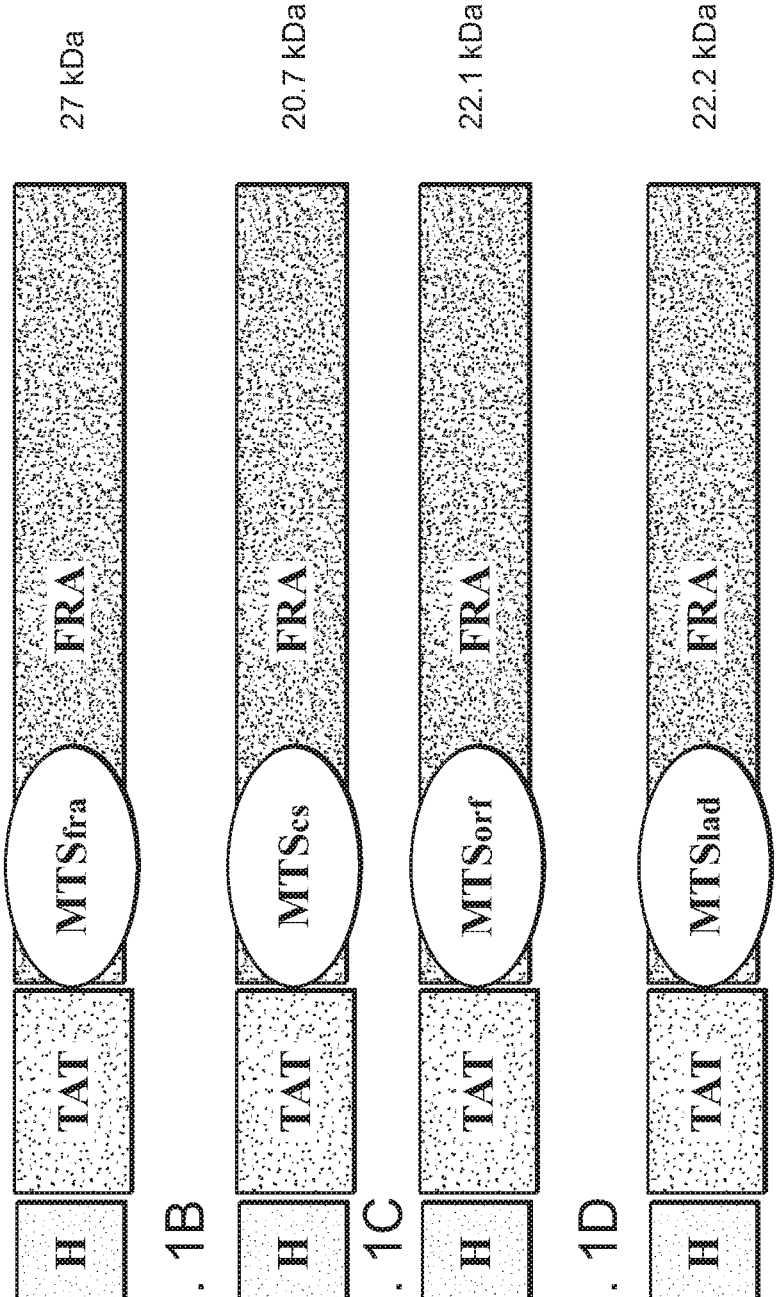

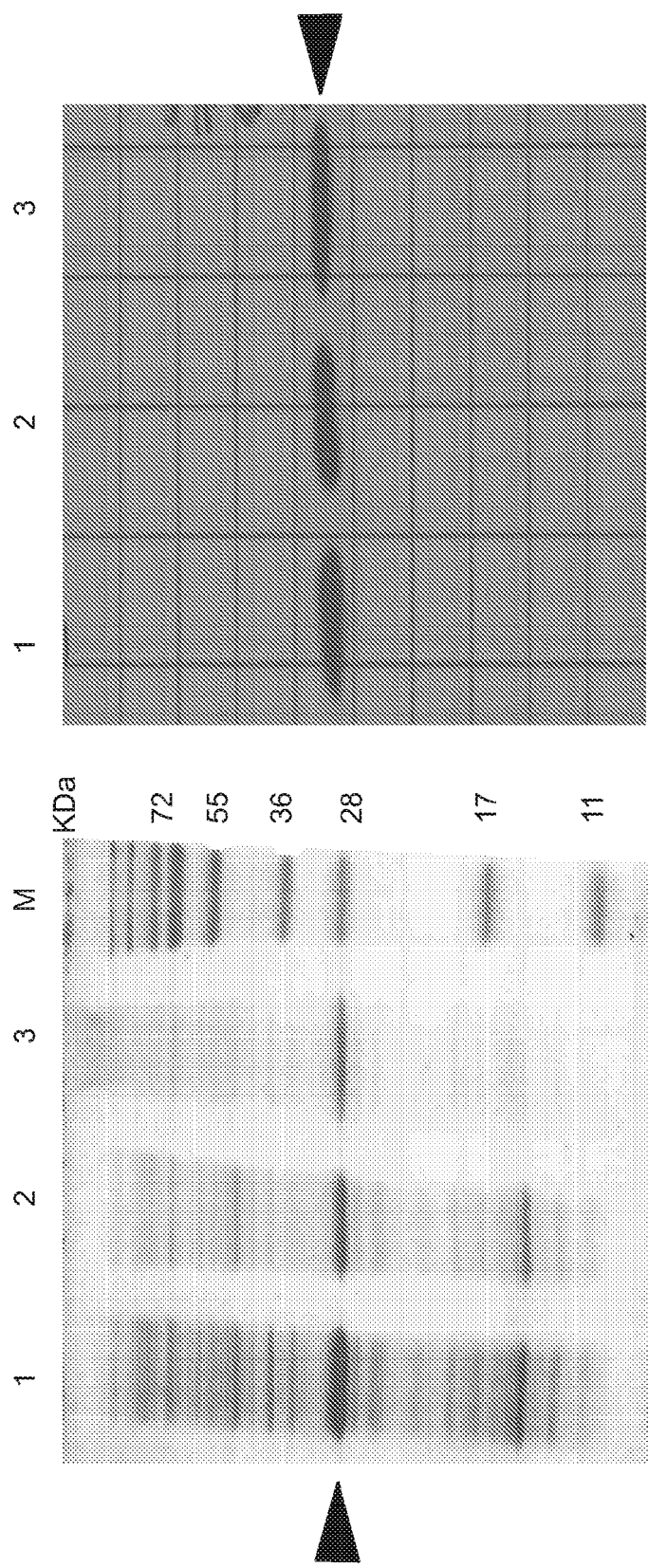

FIG. 15A

MRKKRRQRRRGSDPWTLGRRAVAGLLASPSPAQAQTLTRVPRPAELAPLCGRR
GLRTDIDATCTPRRASSNQRGLNQIWNVKKQSVYLMNLRKSGTLGHPGSLDETT
YERLAEETLDSLAEFFEDLADKPYTFEDYDVSFGSGVLTVKLGGDLGTYVINKQT
PNKQIWLSSPSSGPKRYDWTGKNWVYSHDGVSLHELLAAELTKALKTKLDLSSL
AYSGKDA

FIG. 15B

MRKKRRQRRRGSDPALLTAAARLLGTKNASCLVLAARHASSGTLGHPGSLDETT
YERLAEETLDSLAEFFEDLADKPYTFEDYDVSFGSGVLTVKLGGDLGTYVINKQT
PNKQIWLSSPSSGPKRYDWTGKNWVYSHDGVSLHELLAAELTKALKTKLDLSSL
AYSGKDA

FIG. 15C

MRKKRRQRRRGSDPQSWSRVYCSLAKRGHFNRISHGLQGLSAVPLRTYASGTLG
HPGSLDETTYERLAEETLDSLAEFFEDLADKPYTFEDYDVSFGSGVLTVKLGGDL
GTYVINKQTPNKQIWLSSPSSGPKRYDWTGKNWVYSHDGVSLHELLAAELTKAL
KTKLDLSSLAYSGKDA

FIG. 15D

MRKKRRQRRRGSDPGALVIRGIRNFNLENRAEREISKMKPSVAPRHPSSGTLGHP
GSLDETTYERLAEETLDSLAEFFEDLADKPYTFEDYDVSFGSGVLTVKLGGDLGT
YVINKQTPNKQIWLSSPSSGPKRYDWTGKNWVYSHDGVSLHELLAAELTKALKT
KLDLSSLAYSGKDA

MITOCHONDRIAL PROTEINS CONSTRUCTS AND USES THEREOF

This application is the National Stage of International Application No. PCT/IL2014/050354, filed Apr. 10, 2014, which claims priority to and benefit of U.S. Provisional Patent Application No. 61/811,934, filed Apr. 15, 2013, and U.S. Provisional Patent Application No. 61/869,981, filed Aug. 26, 2013. International Application No. PCT/IL2014/050354 is also a continuation-in-part of U.S. patent application Ser. No. 14/034,224, filed Sep. 23, 2013 and issued as U.S. Pat. No. 8,912,147. The contents of each above-listed application are herein incorporated by reference in their entireties.

SEQUENCE LISTING

The present application contains a Sequence Listing which has been submitted in ASCII format via EFS-Web and is hereby incorporated by reference in its entirety. Said ASCII copy, created on Oct. 13, 2015, is named BIOB-001N01US$_{13}$ $_{ST}$25.txt and is 76,765 bytes in size.

TECHNOLOGICAL FIELD

Disclosed are novel fusion protein constructs comprising a functional mitochondrial protein. Further disclosed are methods of treating mitochondrial disorders by the disclosed fusion proteins and compositions therefor.

PRIOR ART

References considered to be relevant as background to the presently disclosed subject matter are listed below:
[1] Chinnery PF, Schon EA (2003) Mitochondria. J Neurol Neurosurg Psychiatry 74: 1188-1199.
[2] DiMauro S, Schon EA (2003) Mitochondrial respiratory-chain diseases. N Engl J Med 348: 2656-2668.
[3] Brautigam CA, Chuang JL, Tomchick DR, Machius M, Chuang DT (2005) Crystal structure of human dihydrolipoamide dehydrogenase: NAD+/NADH binding and the structural basis of disease-causing mutations. J Mol Biol 350: 543-552.
[4] Brady RO, Schiffmann R (2004) Enzyme-replacement therapy for metabolic storage disorders. Lancet Neurol 3: 752-756.
[5] Wang D, Bonten EJ, Yogalingam G, Mann L, d'Azzo A (2005) Short-term, high dose enzyme replacement therapy in sialidosis mice. Mol Genet Metab 85: 181-189.
[6] Luft FC (2003) Transducing proteins to manipulate intracellular targets. J Mol Med (Berl) 81: 521-523.
[7] Kabouridis PS (2003) Biological applications of protein transduction technology. Trends Biotechnol 21: 498-503.
[8] Green M, Loewenstein PM (1988) Autonomous functional domains of chemically synthesized human immunodeficiency virus tat trans-activator protein. Cell 55: 1179-1188.
[9] Frankel AD, Pabo CO (1988) Cellular uptake of the tat protein from human immunodeficiency virus. Cell 55: 1189-1193.
[10] Futaki S, Suzuki T, Ohashi W, Yagami T, Tanaka S, et al. (2001) Arginine-rich peptides. An abundant source of membrane-permeable peptides having potential as carriers for intracellular protein delivery. J Biol Chem 276: 5836-5840.
[11] Schwarze SR, Ho A, Vocero-Akbani A, Dowdy SF (1999) In vivo protein transduction: delivery of a biologically active protein into the mouse. Science 285: 1569-1572.
[12] Guo X, Hutcheon AE, Zieske JD (2004) Transduction of functionally active TAT fusion proteins into cornea. Exp Eye Res 78: 997-1005.
[13] Del Gaizo V, MacKenzie JA, Payne RM (2003) Targeting proteins to mitochondria using TAT. Mol Genet Metab 80: 170-180.
[14] Harding AE (1981) Friedreich's ataxia: a clinical and genetic study of 90 families with an analysis of early diagnostic criteria and interfamilial clustering of clinical features. Brain 104: 589-620.
[15] Schulz JB, Boesch S, Burk K, Durr A, Giunti P, et al. (2009) Diagnosis and treatment of Friedreich ataxia: a European perspective. Nat Rev Neurol 5: 222-234.
[16] Dun A, Cossee M, Agid Y, Campuzano V, Mignard C, et al. (1996) Clinical and genetic abnormalities in patients with Friedreich's ataxia. N Engl J Med 335: 1169-1175.
[17] Campuzano V, Montermini L, Lutz Y, Cova L, Hindelang C, et al. (1997) Frataxin is reduced in Friedreich ataxia patients and is associated with mitochondrial membranes. Hum Mol Genet 6: 1771-1780.
[18] Rotig A, de Lonlay P, Chretien D, Foury F, Koenig M, et al. (1997) Aconitase and mitochondrial iron-sulphur protein deficiency in Friedreich ataxia. Nat Genet 17: 215-217.
[19] Lodi R, Cooper JM, Bradley JL, Manners D, Styles P, et al. (1999) Deficit of in vivo mitochondrial ATP production in patients with Friedreich ataxia. Proc Natl Acad Sci USA 96: 11492-11495.
[20] Delatycki MB, Camakaris J, Brooks H, Evans-Whipp T, Thorburn DR, et al. (1999) Direct evidence that mitochondrial iron accumulation occurs in Friedreich ataxia. Ann Neurol 45: 673-675.
[21] Tsou AY, Friedman LS, Wilson RB, Lynch DR (2009) Pharmacotherapy for Friedreich ataxia. CNS Drugs 23: 213-223.
[22] Perlman SL (2012) A review of Friedreich ataxia clinical trial results. J Child Neurol 27: 1217-1222.
[23] Rapoport M, Saada A, Elpeleg O, Lorberboum-Galski H (2008) TAT-mediated delivery of LAD restores pyruvate dehydrogenase complex activity in the mitochondria of patients with LAD deficiency. Mol Ther 16: 691-697.
[24] Rapoport M, Salman L, Sabag O, Patel MS, Lorberboum-Galski H (2011) Successful TAT-mediated enzyme replacement therapy in a mouse model of mitochondrial E3 deficiency. J Mol Med (Berl) 89: 161-170.
[25] Vyas PM, Tomamichel WJ, Pride PM, Babbey CM, Wang Q, et al. (2012) A TAT-frataxin fusion protein increases lifespan and cardiac function in a conditional Friedreich's ataxia mouse model. Hum Mol Genet 21: 1230-1247.
[26] Gakh O, Cavadini P, Isaya G (2002) Mitochondrial processing peptidases. Biochim Biophys Acta 1592: 63-77.
[27] Cavadini P, Adamec J, Taroni F, Gakh O, Isaya G (2000) Two-step processing of human frataxin by mitochondrial processing peptidase. Precursor and intermediate forms are cleaved at different rates. J Biol Chem 275: 41469-41475.
[28] Schmucker S, Argentini M, Carelle-Calmels N, Martelli A, Puccio H (2008) The in vivo mitochondrial two-step maturation of human frataxin. Hum Mol Genet 17: 3521-3531.

[29] Gakh O, Bedekovics T, Duncan SF, Smith DYt, Berkholz DS, et al. (2010) Normal and Friedreich ataxia cells express different isoforms of frataxin with complementary roles in iron-sulfur cluster assembly. J Biol Chem 285: 38486-38501.

[30] Gavel Y, von Heijne G (1990) Cleavage-site motifs in mitochondrial targeting peptides. Protein Eng 4: 33-37.

[31] Braun HP, Schmitz UK (1997) The mitochondrial processing peptidase. Int J Biochem Cell Biol 29: 1043-1045.

[32] Horwich A (1990) Protein import into mitochondria and peroxisomes. Curr Opin Cell Biol 2: 625-633.

[33] Saada A, Edvardson S, Rapoport M, Shaag A, Amry K, et al. (2008) C6ORF66 is an assembly factor of mitochondrial complex I. Am J Hum Genet 82: 32-38.

[34] Cheng TL, Liao CC, Tsai WH, Lin CC, Yeh CW, et al. (2009) Identification and characterization of the mitochondrial targeting sequence and mechanism in human citrate synthase. J Cell Biochem 107: 1002-1015.

[35] Santos R, Lefevre S, Sliwa D, Seguin A, Camadro JM, et al. (2010) Friedreich ataxia: molecular mechanisms, redox considerations, and therapeutic opportunities. Antioxid Redox Signal 13: 651-690.

[36] Bulteau AL, O'Neill HA, Kennedy MC, Ikeda-Saito M, Isaya G, et al. (2004) Frataxin acts as an iron chaperone protein to modulate mitochondrial aconitase activity. Science 305: 242-245.

[37] Richardson TE, Yu AE, Wen Y, Yang SH, Simpkins JW (2012) Estrogen prevents oxidative damage to the mitochondria in Friedreich's ataxia skin fibroblasts. PLoS One 7: e34600.

[38] WO 2009/098682.

[39] http://www.curefa.org/pipeline.html.

[40] Tang N, et al. (2012) Stable Overexpression of Arginase I and Ornithine Transcarbamylase in HepG2 Cells Improves Its Ammonia Detoxification. Journal of Cellular Biochemistry 113: 518-527.

[41] Cunningham, S. C. et al. (2011) Induction and Prevention of Severe Hyperammonemia in the Spf$^{ash}$ Mouse Model of Ornithine Transcarbamylase Deficiency Using snRNA and rAAV-mediated Gene Delivery. Molecular Therapy 19(5):854-9.

Acknowledgement of the above references herein is not to be inferred as meaning that these are in any way relevant to the patentability of the presently disclosed subject matter.

BACKGROUND

Mitochondria play a major and critical role in cellular homeostasis—they participate in intracellular signaling and apoptosis, and perform numerous biochemical tasks, such as in pyruvate oxidation, in the citric acid cycle (also referred to as the Krebs cycle), and in metabolism of amino acids, fatty acids, nucleotides and steroids. However, the most crucial task of mitochondria is their role in cellular energy metabolism. This includes β-oxidation of fatty acids and production of ATP by means of the electron-transport chain and the oxidative-phosphorylation system [1, 2].

Most of the approximately 900 gene products in the mitochondria are encoded by nuclear DNA (nDNA) while mitochondrial DNA (mtDNA) only contains 13 protein encoding genes. Most of the polypeptides encoded by nDNA genes are synthesized with a mitochondrial targeting sequence (MTS), allowing their import from the cytoplasm into mitochondria through the translocation machinery (TOM/TIM). Upon entering the mitochondria, the MTS is recognized and cleaved off, allowing for proper processing and, if necessary, assembly into mitochondrial enzymatic complexes [3].

Currently, there is no cure for genetic mitochondrial metabolic disorders and treatment is mostly palliative.

Enzyme or Protein Replacement Therapy (E/PRT) is a therapeutic approach for metabolic disorders, whereby the deficient or absent protein/enzyme is artificially manufactured, purified and administered intravenously to the patient in need thereof on a regular basis.

After many years of extensive research, E/PRT has been successfully accepted as the treatment of choice for metabolic lysosomal storage diseases, including Gaucher disease, Fabry disease and attenuated variants of mucopolysaccharidoses type 1 (MPS 1). However, the inability of the intravenously administered enzymes to penetrate the blood-brain barrier severely limits the application of this approach for the treatment of other metabolic disorders that involve the central nervous system (CNS) [4, 5].

One approach for delivering proteins into cells is their fusion with protein transduction domains (PTDs), a group of short peptides that serve as delivery vectors for large molecules. Generally, PTDs are defined as short, water-soluble and partly hydrophobic, and/or polybasic peptides (at most 30-35 amino acids residues) with a net positive charge at physiological pH [6, 7]. The main feature of PTDs is that they are able to penetrate the cell membrane at low micromolar concentrations both in vitro and in vivo without using any chiral receptors and without causing significant membrane damage.

Furthermore, and even more importantly, these peptides are capable of internalizing electrostatically or covalently bound biologically active cargoes (such as drugs) with high efficiency and with low toxicity. The mechanism(s) by which PTDs enter the cells has not been completely understood. One of the well-characterized PTDs is the transactivator of transcription (TAT) peptide originating from the HIV-1 virus. TAT is an 11-amino-acid (residues 47-57) arginine- and lysine-rich portion of the Tat protein encoded by HIV-1 virus [8, 9]. TAT-fusion proteins have been previously shown to be rapidly and efficiently introduced into cultured cells, intact tissue and live tissues when injected into mice [10-12]. It has also been demonstrated that TAT fusion proteins traverse mitochondrial membranes [13, 38].

There has been great progress in the use of PTD-fusion proteins for the delivery of different macromolecules into cells both in vitro and in vivo. This system can be used even for the delivery of cargoes into the brain across the blood-brain barrier. In addition, the ability to target specific intracellular sub-localizations, such as the nuclei, the mitochondria and lysosomes, further expands the possibilities of this delivery system to the development of sub-cellular organelle-targeted therapy. The therapeutic applications seem almost unlimited, and the use of the TAT-based delivery system has extended from proteins to a large variety of cargoes such as oligonucleotides, imaging agents, low molecular mass drugs, nanoparticles, micelles and liposomes. As will be shown, this PTD system is used for developing fusion constructs of functional mitochondrial proteins, for treatment of mitochondrial disorders, for example Friedreich ataxia.

Friedreich ataxia is an autosomal recessive degenerative disorder characterized by ataxia, areflexia, sensory loss, weakness, scoliosis, and cardiomyopathy. Diabetes mellitus, optic neuropathy, and hearing loss are also seen in patients suffering from this disease [14, 15]. Most patients with Friedreich ataxia (97%) have expansions of a GAA repeat in the first intron on both alleles of the gene encoding the mitochondrial protein frataxin [15, 16] whose expression is reduced in Friedreich ataxia [17]. The size of the GAA repeat expansion inversely correlates with frataxin expression and with the age of disease onset [16]. A deficiency of frataxin in cells leads to decreased activities of mitochondrial iron-sulfur cluster-containing enzymes, to an accumulation of iron in the mitochondrial matrix, increased sensitivity to oxidative stress, as well as to impaired adenosine triphosphate (ATP) production [18-20].

Current targets for disease-modifying drug development include agents targeting the mitochondria, aimed to (1) reduce oxidative stress and free-radical generation; (2) improve ATP production; (3) reduce iron accumulation; and (4) increase frataxin production and the assembly of iron-sulfur clusters [21]. There are presently 21 agents or classes of therapeutic agents enrolled in the research pipeline of Friedreich ataxia disease [39]. Millions of dollars from public, private, and industry-based initiatives have been dedicated to research of Friedreich ataxia therapeutics. Despite this vigorous international effort, there is as yet no proven disease-modifying therapy for Friedreich ataxia [22].

Development of E/PRT using the TAT delivery system in mitochondria disorders was previously reported for lipoamide dehydrogenase (LAD) mitochondrial deficiency [23, 38]. LAD is the E3 subunit of the three α-ketoacid dehydrogenase complexes in the mitochondrial matrix, which are crucial for the metabolism of carbohydrates and amino acids. These complexes are the pyruvate dehydrogenase complex (PDHC), the α-ketoglutarate dehydrogenase complex (KGDHC) and the branched chain ketoacid dehydrogenase complex (BCKDHC). This previously reported TAT delivery system was based on a TAT-LAD fusion protein comprising the natural precursor sequence of the human LAD containing the N-terminal 35 amino acid mitochondria targeting sequence (MTS). The natural MTS of LAD was used to facilitate processing of the TAT-LAD construct upon delivery into the mitochondria, thus allowing the incorporation of the delivered LAD into the α-ketoacid dehydrogenase complexes. This TAT-LAD construct was demonstrated to enter patients' cells rapidly, and efficiently reaching the mitochondria. Inside the mitochondria, TAT-LAD was shown to be processed and to restore LAD activity [23]. Moreover, delivery of TAT-LAD into E3-deficient mice tissues was also demonstrated [24]. In mice tissues, a single administration of TAT-LAD resulted in a significant increase in the enzymatic activity of the mitochondrial multienzyme complex pyruvate-dehydrogenase complex within the liver, heart and, most importantly, brain of TAT-LAD-treated E3-deficient mice [24].

Notably, TAT-LAD was shown to be able to restore the activity of the pyruvate dehydrogenase complex (PDHC) within treated patients' cells almost back to its normal levels. PDHC is a $9.5 \times 10^6$ Da macromolecular machine whose multipart structure assembly process involves numerous different subunits: a pentagonal core of 60 units of the E2 component (dihydrolipoamide), attached to 30 tetramers of the E1 component (α2β2) (pyruvate decarboxylase), 12 dimers of the E3 (LAD, dihydrolipoamide) component and 12 units of the E3 binding protein. The structure of all α-ketoacid dehydrogenase complexes is similar to that of PDHC. The complexity of this structure emphasizes the significance in showing that TAT-mediated replacement of one mutated component restores the activity of an essential mitochondrial multi-component enzymatic complex in cells of enzyme-deficient patients.

Previous studies of mitochondria delivery system primarily used the native MTS of mitochondrial proteins (e.g. LAD) and showed that the native MTS was necessary for maximal restoration of LAD enzymatic function. Deleting the MTS restored a significantly smaller amount of LAD activity within the mitochondria. Since TAT can move both ways across a membrane and thus pull the therapeutic cargo out of the mitochondria, when MTS is included, the matrix processing peptidases recognizes the sequence and clips it, and the cargo (e.g. mature LAD) is left in the mitochondrial matrix while the TAT peptide can transduce out of the mitochondrion. Repeated dosing should therefore result in accumulating amounts of cargo in the mitochondria over time.

A TAT-FRATAXIN (TAT-FRA, also referred to as TAT-FXN) fusion protein for putative treatment of Friedreich's ataxia was recently reported [25]. This TAT-FXN fusion protein was shown to bind iron in vitro, transduce into the mitochondria of Friedreich ataxia deficient fibroblasts and also reduce caspase-3 activation in response to an exogenous iron-oxidant stress. In this TAT-FXN fusion protein, the authors used the native MTS of frataxin that consists of 80 amino acid residues (aa) for preparing their TAT-FXN fusion protein [26].

It is known that FXN mRNA is translated to a precursor polypeptide that is transported to the mitochondrial matrix and processed to at least two forms, namely FXN42-210 and FXN81-210. FXN42-210 is a transient processing intermediate, whereas FXN81-210 represents the mature protein [27, 28]. However, it was found that both FXN42-210 and FXN81-210 are present in control cell lines and tissues at steady-state, and that FXN42-210 is consistently more depleted than FXN81-210 in samples from Friedreich's ataxia patients [29].

Most nuclear-encoded mitochondrial proteins contain a cleavable N-terminal MTS that directs mitochondrial targeting of the protein; as detailed above, the N-terminal MTS is cleaved off by matrix processing proteases at a well-conserved RXY ↓ (S/A) motif, which is a three amino acid (aa) motif, where X can be any aa, followed by serine or alanine and cleavage is performed after the three first amino acids [26, 30-31]. These N-terminal MTSs are typically 15-30 amino acids in length including 3-5 nonconsecutive basic amino acid (arginine/lysine) residues, often with several serine/threonine residues but without acidic amino acid (asparate/glutamate) residues. In their molecular structure, these MTSs are able to form strong basic amphipathic α-helices that are essential for efficient mitochondrial transportation [32]. Thus, by way of example, the long 80-aa native MTS of frataxin as well as its two-step processing can reduce its efficiency in the delivery of cargos into the matrix of the mitochondria.

SUMMARY OF THE INVENTION

Provided is a fusion protein comprising a HIV-1 transactivator of transcription (TAT) domain, a functional human mitochondrial protein and a human mitochondria targeting sequence (MTS) situated between said TAT domain and said functional human mitochondrial protein and wherein said human MTS is heterologous to said functional human mitochondrial protein.

In the disclosed fusion protein said functional human mitochondrial protein can be situated C-terminal to said human MTS.

In the disclosed fusion protein said human mitochondrial protein can be a functional human mitochondrial protein per se and/or a component of a mitochondrial multi-component complex, for example human frataxin and ornithine transcarbamoylase (OTC).

In the disclosed fusion protein, said MTS can comprise from about 15 to about 40 amino acid residues, including from about 3 to about 5 nonconsecutive basic amino acid residues, and optionally from about 1 to about 3 or 4 or 5 serine/threonine residues.

Non-limiting examples of the MTS comprised in the disclosed fusion protein are any one of human mitochondrial citrate synthase MTS (the amino acid and the nucleic acid sequence encoding therefor are denoted by SEQ ID NO. 23 and SEQ ID NO. 3, respectively), the human lipoamide dehydrogenase MTS (the amino acid and the nucleic acid sequence encoding therefor are denoted by SEQ ID NO. 24 and SEQ ID NO. 5, respectively), the MTS of the human C6ORF66 gene product (the amino acid and the nucleic acid sequence encoding therefor are denoted by SEQ ID NO. 25 and SEQ ID NO. 4, respectively) and the MTS of human mitochondrial GLUD2 (encoded by the nucleic acid sequence denoted by SEQ ID NO. 16).

Further provided is a fusion protein comprising a HIV-1 transactivator of transcription (TAT) domain fused to a functional human mitochondrial protein and a human mitochondria targeting sequence (MTS) of a human mitochondrial protein selected from citrate synthase (CS) and lipoamide dehydrogenase (LAD) situated between said TAT domain and said functional human mitochondrial protein, wherein said functional human mitochondrial protein is C-terminal to said MTS of human lipoamide dehydrogenase or human citrate synthase.

The disclosed fusion protein as herein defined may further comprise a linker covalently linking said TAT domain to said MTS sequence.

In the disclosed fusion protein, the fusion protein may have the amino acid sequence denoted by SEQ ID NO. 30, comprising a HIV-1 transactivator of transcription (TAT) domain having the amino acid sequence denoted by SEQ ID NO. 27 fused to human frataxin having the amino acid sequence denoted by SEQ ID NO. 26 and a mitochondria targeting sequence (MTS) of human lipoamide dehydrogenase having the amino acid sequence denoted by SEQ ID NO. 24, said MTS situated between said TAT domain and said frataxin, and is linked to said TAT domain via a linker having the amino acid sequence denoted by SEQ ID NO. 32, and wherein said frataxin is C-terminal to said MTS of human lipoamide dehydrogenase.

In further embodiments of the disclosed fusion protein, the fusion protein may have the amino acid sequence denoted by SEQ ID NO. 28, comprising a HIV-1 transactivator of transcription (TAT) domain having the amino acid sequence denoted by SEQ ID NO. 27 fused to human frataxin having the amino acid sequence denoted by SEQ ID NO. 26 and a mitochondria targeting sequence (MTS) of human citrate synthase having the amino acid sequence denoted by SEQ ID NO. 23, said MTS situated between said TAT domain and said frataxin, and is linked to said TAT domain via a linker having the amino acid sequence denoted by SEQ ID NO. 32, and wherein said frataxin is C-terminal to said MTS of human citrate synthase.

Further disclosed is a composition comprising a physiologically acceptable carrier and as an active ingredient a fusion protein as disclosed herein, and a pharmaceutical composition comprising a physiologically or a pharmaceutically acceptable carrier and as an active ingredient a fusion protein as disclosed herein.

Further disclosed is a pharmaceutical composition for restoring, at least in part, activity of a defective or deficient or unfunctional human mitochondrial protein in a subject in need. The said human mitochondrial protein can be active per se, or can be a member of a functional mitochondrial protein complex.

Further disclosed is a composition comprising a physiologically acceptable carrier and as an active ingredient a fusion protein comprising a HIV-1 transactivator of transcription (TAT) domain fused to human frataxin and a human mitochondria targeting sequence (MTS) of a human mitochondrial protein selected from citrate synthase (CS) and lipoamide dehydrogenase (LAD) situated between said TAT domain and said frataxin, wherein said frataxin is C-terminal to said MTS of human lipoamide dehydrogenase or human citrate synthase, as disclosed herein.

The present disclosure further provides a composition comprising as an active ingredient a fusion protein having the amino acid sequence denoted by SEQ ID NO. 30 or a fusion protein having the amino acid sequence denoted by SEQ ID NO. 28 and a physiologically acceptable carrier.

The pharmaceutical composition disclosed herein can be intended for treating or alleviating a mitochondrial disorder, such as but not limited to Friedreich's ataxia or any other disorder associated with deficiency of frataxin or defective frataxin or a disorder associated with a deficiency of OTC or with defective OTC.

Further disclosed is a pharmaceutical composition for the treatment of Friedreich's Ataxia by intravenous administration to a subject in need thereof, said composition comprising a therapeutically effective amount of a fusion protein having the amino acid sequence denoted by SEQ ID NO. 30 or a fusion protein having the amino acid sequence denoted by SEQ ID NO. 28 and at least one of pharmaceutically acceptable carrier, diluent, additive and excipient.

A non-limiting example of a pharmaceutical composition as herein defined is wherein the therapeutically effective amount administered is from about 0.5 mg/Kg to about 2 mg/Kg body weight of the subject.

Thus, the disclosed fusion protein can be used in a method for the treatment of a mitochondrial disorder, such as but not limited to Friedreich's ataxia or any other disorder associated with deficiency of frataxin or defective frataxin or, respectively a disorder associated with a deficiency of OTC or with defective OTC.

Further provided is a method for treating or alleviating a mitochondrial disorder, said method comprising the step of administering to a subject in need of such treatment a therapeutically effective amount of the fusion protein disclosed herein, thereby treating a mitochondria disorder.

In some embodiments of the disclosed method, the functional protein is frataxin, respectively OTC, and the mitochondrial disorder is Friedreich's ataxia or any other disorder associated with deficiency of frataxin or defective frataxin or, respectively, a disorder associated with a deficiency of OTC or with defective OTC.

The disclosed method for treating or alleviating a mitochondrial disorder can further comprises administering an additional therapeutic agent.

Further provided is a method for introducing a functional mitochondrial protein into mitochondria of a subject, said method comprising the step of administering to a subject in need of such treatment a therapeutically effective amount of the fusion protein as disclosed herein, thereby introducing a functional human mitochondrial protein into the mitochondria of a subject in need thereof.

In the disclosed method for introducing a functional mitochondrial protein into mitochondria of a subject, said introduced functional human mitochondrial protein may restore at least partial activity of a wild type human mitochondrial protein, at least 5%, at least 10%, at least 20%, at least 30%, at least 40%, at least 50%, at least 60%, at least 70%, at least 80%, at least 90% or up to 100% of the activity of a wild type human mitochondrial protein.

Further disclosed is a method for restoring, at least in part, activity of a defective or deficient or un-functional human mitochondrial protein in a subject in need, by administering to said subject a therapeutically effective amount of a fusion protein according to the present disclosure. The said human mitochondrial protein can be active per se, or can be a member of a functional mitochondrial protein complex.

Still further, provided is a method for alleviating oxidative stress in a subject in need thereof, said method comprising the step of administering to a subject in need of such treatment a therapeutically effective amount of the fusion protein as disclosed herein, thereby alleviating oxidative stress in said subject.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A-1D: Schematic structures of the various TAT-MTS-FRA fusion proteins and the expected molecular weights thereof Abbreviations: H, His tag; TAT, transactivator of transcription; FRA (or fra), Frataxin; MTS, mitochondrial translocation sequence; cs, Citrate synthase; orf, C6ORF66; lad, LAD and kDa, kilo Dalton.

FIG. 2A-2D: Expression and sub-cellular localization of TAT-MTSfra-FRA and of TAT-MTSorf-FRA fusion proteins FIG. 2 presents an image of SDS-PAGE analysis of bacterial sub-fractions expressing the TAT-MTSfra-FRA fusion protein (FIG. 2A) and an immunoblot of Western blot analysis thereof (FIG. 2B) using anti-His antibody; an image of SDS-PAGE analysis of bacterial sub-fractions expressing TAT-MTSorf-FRA fusion protein (FIG. 2C) and an immunoblot of Western blot analysis thereof using anti-His antibody is presented in FIG. 2D.

Abbreviations (for FIGS. 2A-2D): 1, whole cell extract; 2, soluble fraction; 3, insoluble fraction; kDa, kilo Dalton; and M=marker. Arrow heads indicate the fusion proteins.

FIG. 3A-3D: Expression and sub-cellular localization of TAT-MTSlad-FRA and TAT-MTScs-FRA fusion proteins FIG. 3 presents an image of SDS-PAGE analysis of bacterial sub-fractions expressing the TAT-MTSlad-FRA fusion protein (FIG. 3A) and an immunoblot of Western blot analysis thereof (FIG. 3B) using anti-His antibody; an image of SDS-PAGE analysis of bacterial sub-fractions expressing TAT-MTScs-FRA fusion protein (FIG. 3C) and an immunoblot of Western blot analysis thereof using anti-His antibody is presented in FIG. 3D.

Abbreviations (for FIG. 3A-3D): 1, whole cell extract; 2, soluble fraction; 3, insoluble fraction; KDa, kilo Dalton; and M=marker. Arrow heads indicate the fusion proteins.

FIG. 4A-4D: Purification of TAT-MTSfra-FRA and of TAT-MTSorf-FRA fusion proteins FIG. 4 presents an image of an affinity chromatography purification profile of the fusion protein TAT-MTSfra-FRA (FIG. 4A) and an image of SDS-PAGE analysis of the purification steps obtained for TAT-MTSfra-FRA is presented in FIG. 4B. An image of an affinity chromatography purification profile of the fusion protein TAT-MTSorf-FRA is presented in FIG. 4C and an image of SDS-PAGE analysis of the purification steps obtained for TAT-MTSorf-FRA is presented in FIG. 4D.

Abbreviations: M, marker; 1, whole cell extract; 2, pre-run fraction (the soluble sub-fraction of bacterial cells expressing the fusion protein); 3, flow through; 4, elution with 100 mM imidazole; and 5-9, elution with 250 mM imidazole.

FIG. 5A-5D: Purification of TAT-MTSlad-FRA and of TAT-MTScs-FRA fusion proteins

Figure 5A:
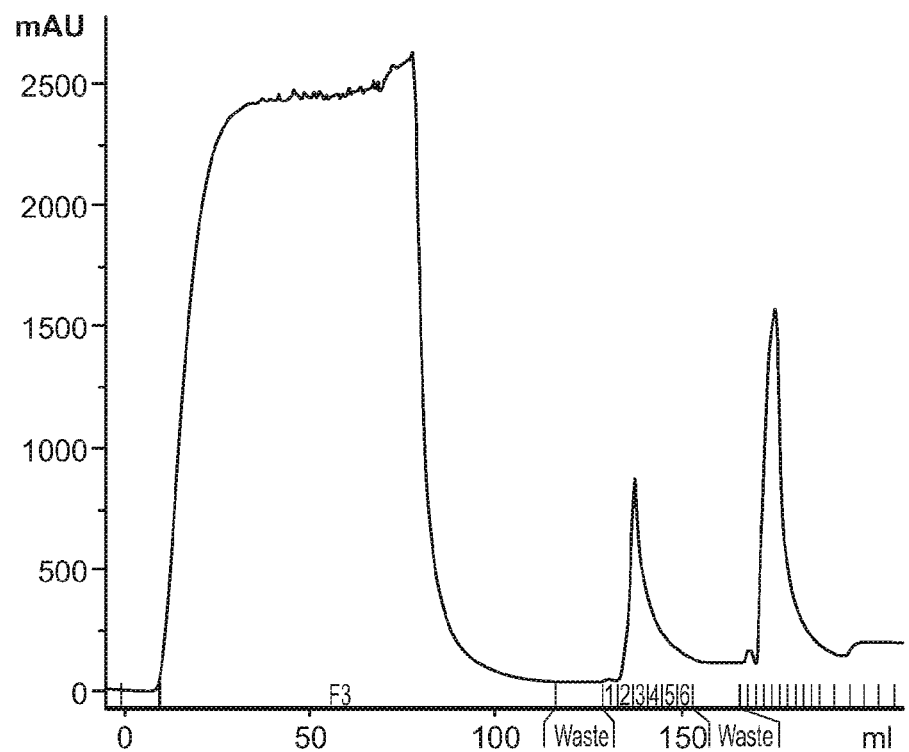
Figure 5B:
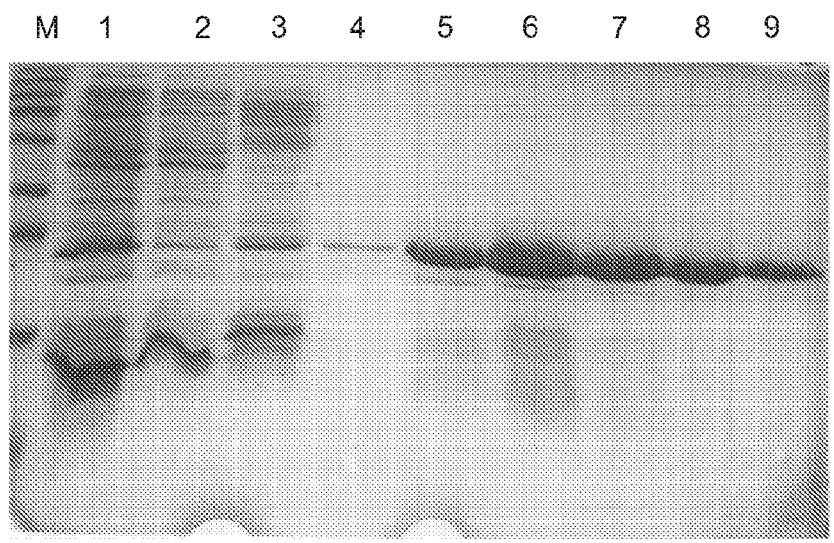

FIG. 5 presents an image of an affinity chromatography purification profile of the fusion protein TAT-MTSlad-FRA (FIG. 5A) and an image of SDS-PAGE analysis of the purification steps obtained for TAT-MTSlad-FRA is presented in FIG. 5B. An image of an affinity chromatography purification profile of the fusion protein TAT-MTScs-FRA is presented in FIG. 5C and an image of SDS-PAGE analysis of the purification steps obtained for TAT-MTScs-FRA is presented in FIG. 5D.

Abbreviations: M, marker; 1, whole cell extract; 2, pre-run fraction (the soluble sub-fraction of bacterial cells expressing the fusion protein); 3, flow through; 4, elution with 100 mM imidazole; and 5-9, elution with 250 mM imidazole.

Figure 6A:
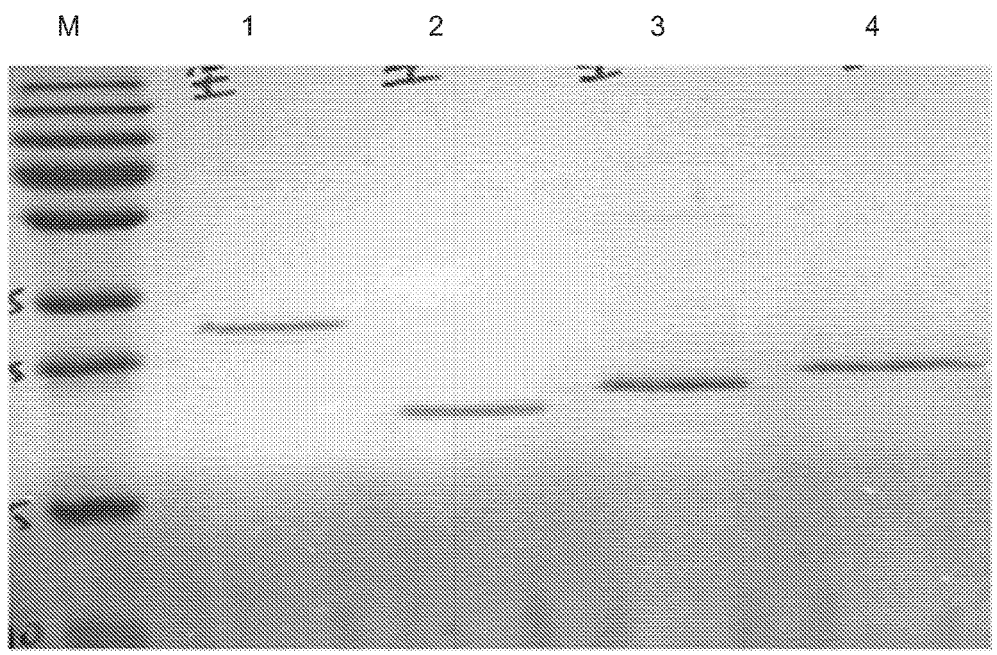
Figure 6C:
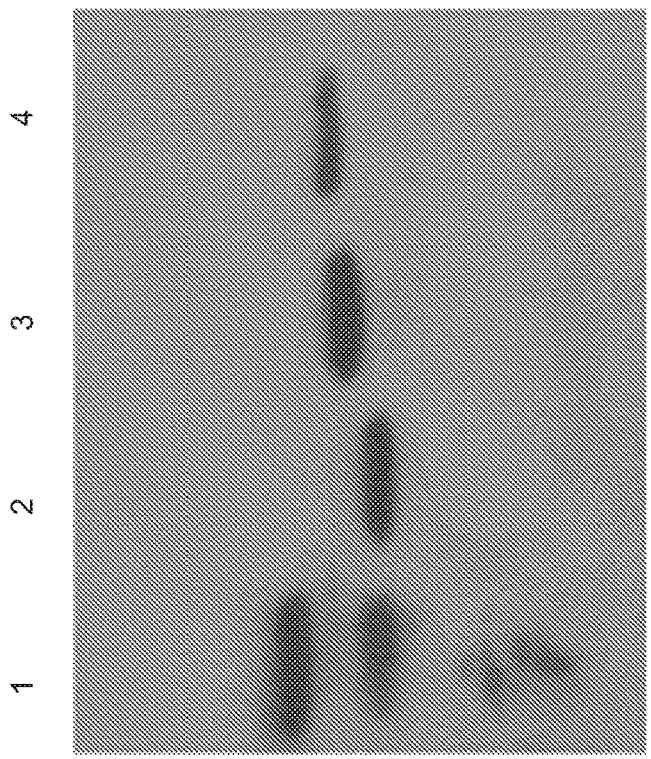
Figure 6B:
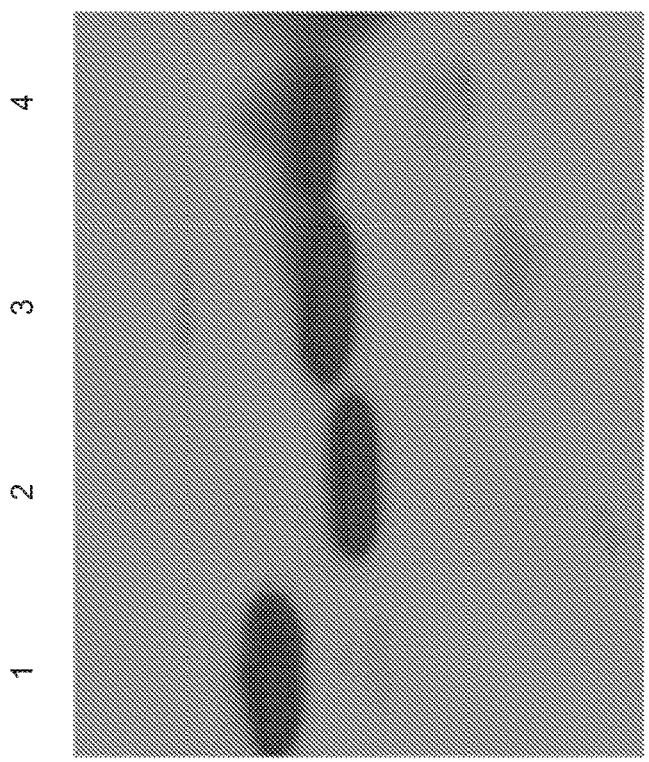

FIG. 6A-6C: Characterization of TAT-MTS-FRA highly purified fusion proteins

The four highly purified TAT-MTS-FRA fusion proteins were characterized by a SDS-PAGE gel (FIG. 6A) and by Western blot analyses using anti-His (FIG. 6B) or anti-frataxin (FIG. 6C) antibodies.

Abbreviations: 1, TAT-MTSfra-FRA; 2, TAT-MTScs-FRA; 3, TAT-TSlad-FRA; 4, TAT-MTSorf-FRA; and M, Marker.

Figure 7A:
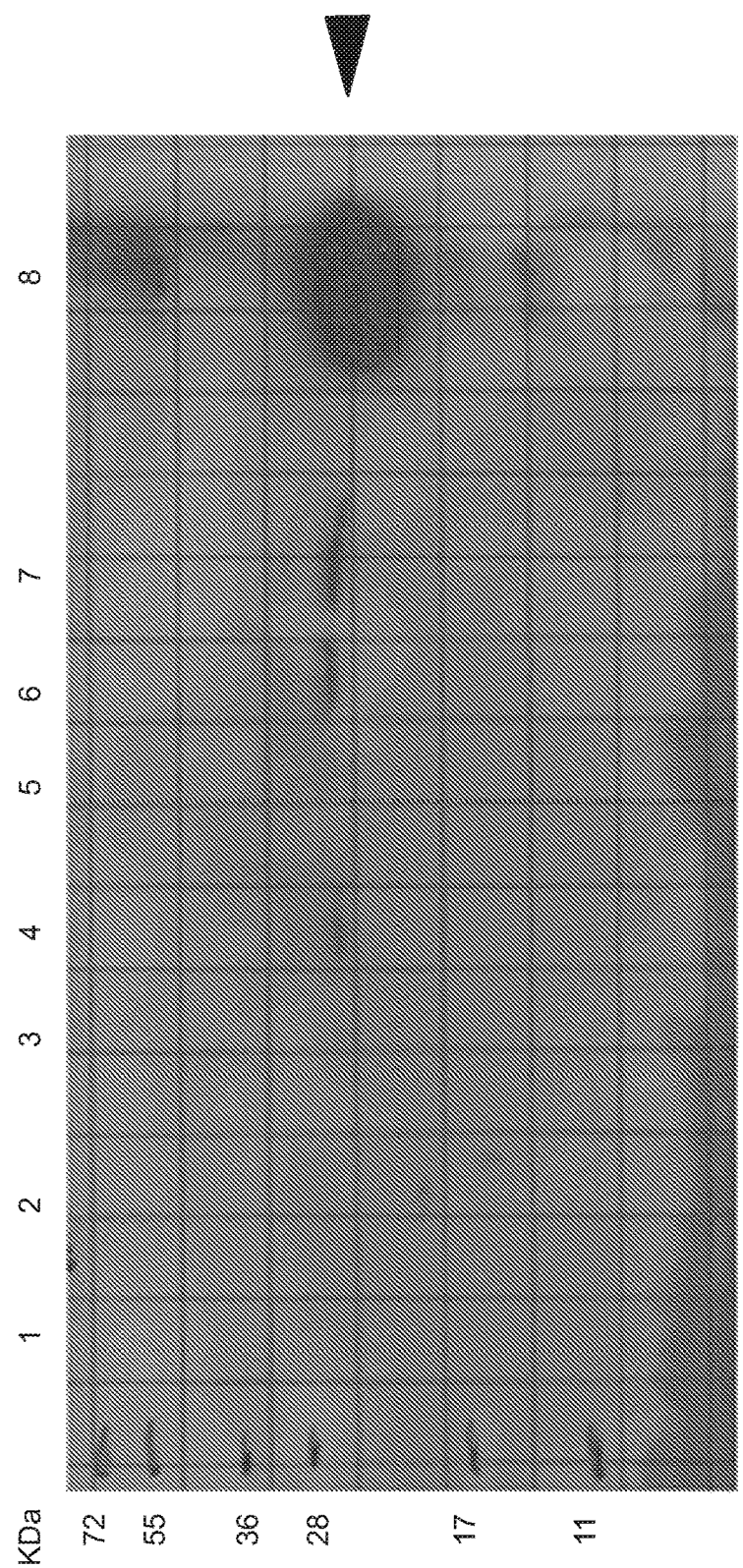
Figure 7B:
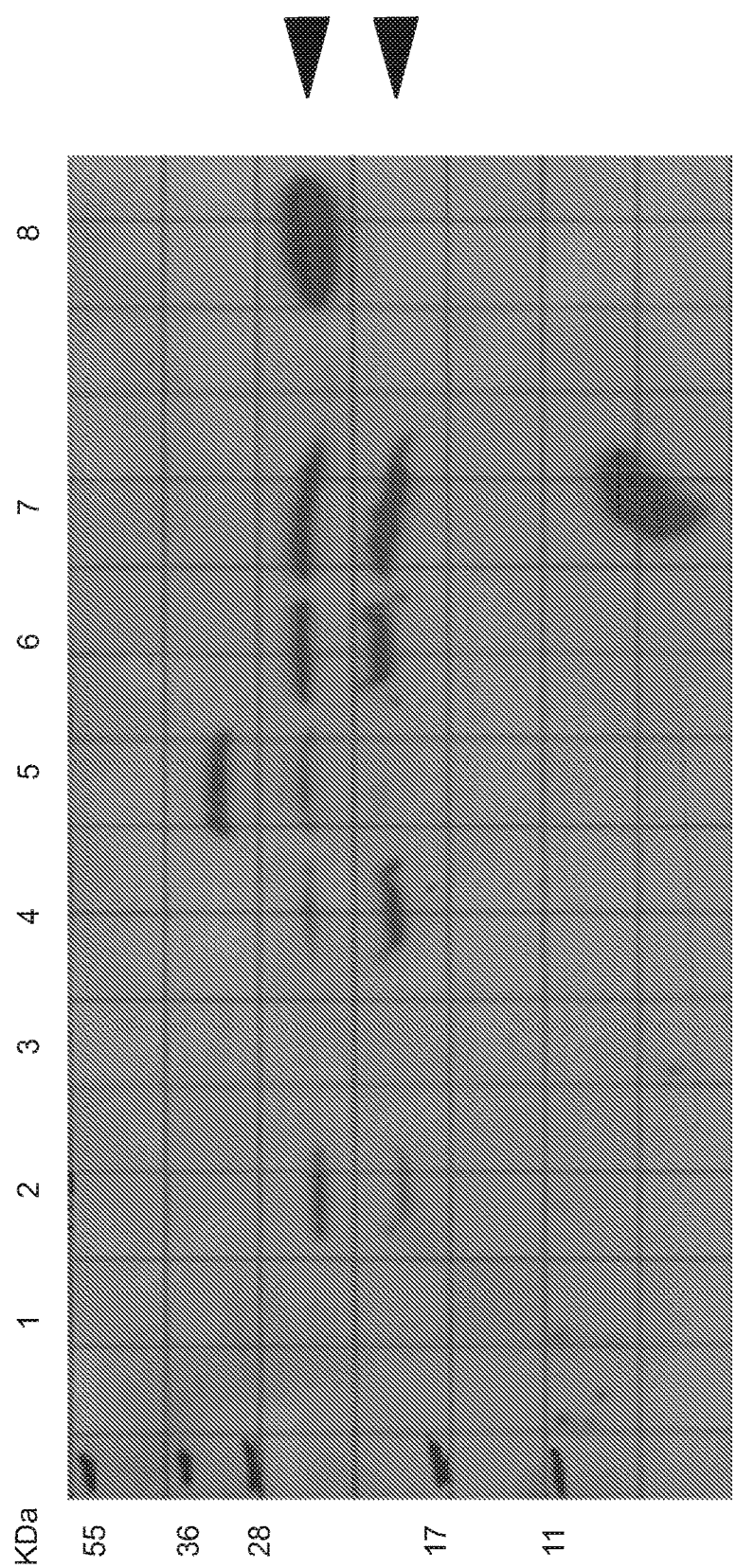

FIG. 7A-7B: Internalization of TAT-MTSlad-FRA into cells and their mitochondria

FIG. 7A presents an immunoblot of a Western blot analysis using anti-His antibodies and FIG. 7B presents an immunoblot of a Western blot analysis using anti frataxin antibodies performed with BJAB cells incubated in the absence (lanes 1 & 2) or in the presence of TAT-MTSlad-FRA (lanes 3-7). At the end of the incubation period, sub-fractionation was performed, obtaining the cytoplasmic and mitochondrial fractions. Fractions were separated by SDS-PAGE and subjected to Western blot analysis. Abbreviations: control, untreated cells: cytoplasm (1), mitochondria (2); cells treated for 1 hr with the fusion protein: cytoplasm (3), mitochondria (4); cells treated for 5 hr: cytoplasm (5), mitochondria (6, 7; from two separate experiments); highly purified TAT-MTSlad-FRA fusion protein as a positive control is shown in (8). Arrow-heads indicate the fusion protein (or its processing products, indicated by the lower arrow-head in FIG. 7B).

Figure 8A:
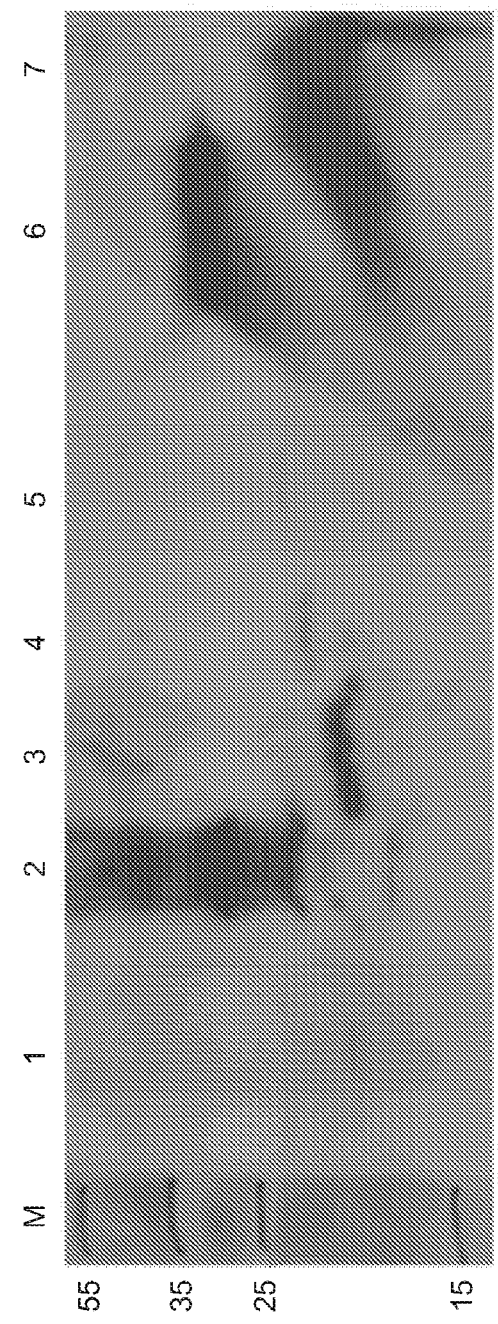
Figure 8B:
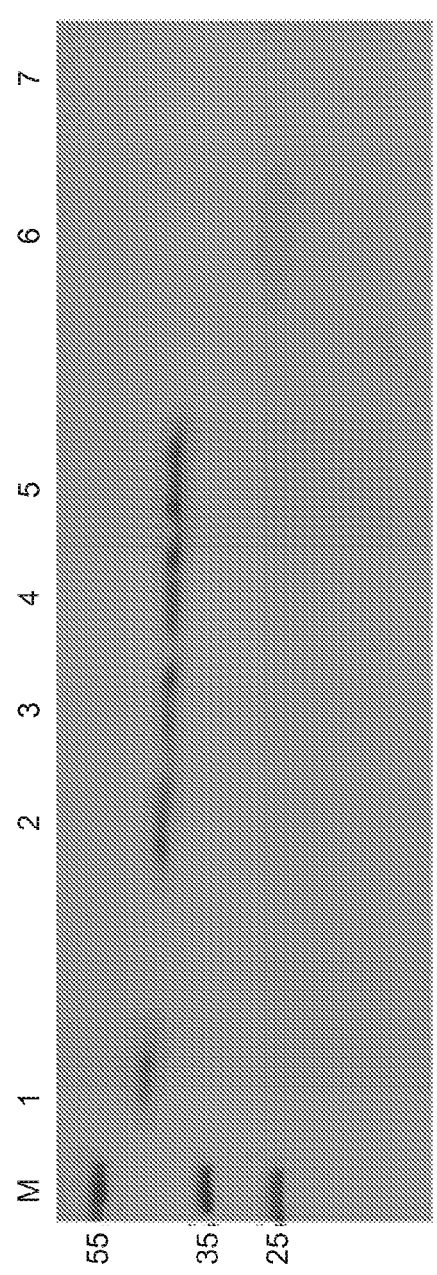

FIG. 8A-8B: Internalization of TAT-MTS-FRA fusion proteins into mitochondria of cells FIG. 8A presents a Western blot analysis using anti-frataxin antibodies of cells incubated for 3 hours with TAT-MTS-FRA fusion proteins, each fusion protein at a final concentration of 0.02 µg/µl. The cells were washed and their mitochondria were isolated.

FIG. 8B presents a Western blot analysis using anti-E1α antibodies of cells as detailed above.

Abbreviations: M, marker; mitochondria isolated from control cells without any treatment (1), cells incubated with TAT-MTSfra-FRA (2), cells incubated with TAT-MTScs- FRA (3), cells incubated with TAT-MTSlad-FRA (4), cells incubated with TAT-MTSorf-FRA (5), purified TAT-MTS-fra-FRA fusion protein (6), and purified TAT-MTScs-FRA fusion protein (7).

Figure 9:
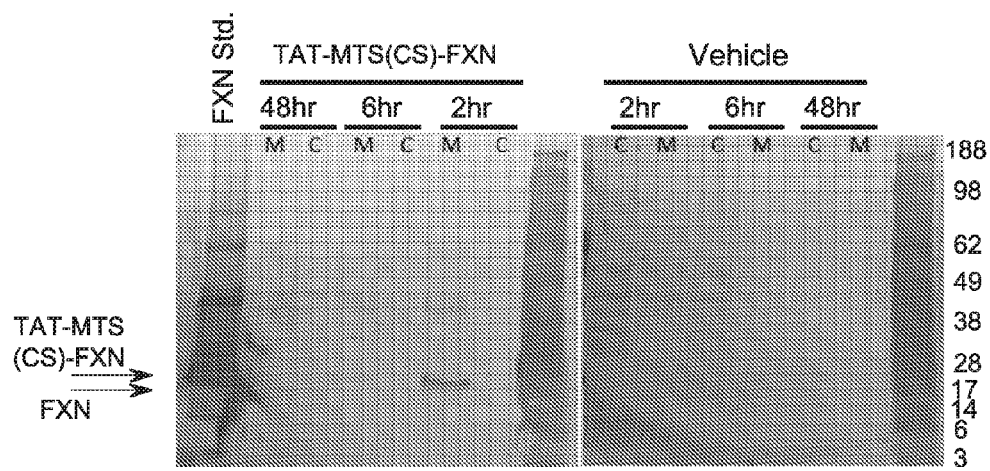

FIG. 9: Internalization of TAT-MTScs-FRA to fibroblasts of FRA patients

An immunoblot of a Western blot analysis using an anti-Frataxin antibody performed for mitochondrial (M) and cytosolic (C) fractions of fibroblasts (F816) obtained from Friedreich's ataxia patients that were incubated in the presence of 20 µg/ml TAT-MTScs-FRA (or vehicle) for 2, 6 and 48 hours, with fresh addition of TAT-MTScs-FRA (at 20 µg/ml) after 24 hours. TAT-MTScs-FRA and processed Frataxin are marked with arrows. Abbreviations: kDa, kilodalton; TAT, transactivator of transcription; MTS, mitochondria targeting sequence; CS, citrate synthase; FXN, frataxin; Std, standard.

Figure 10:
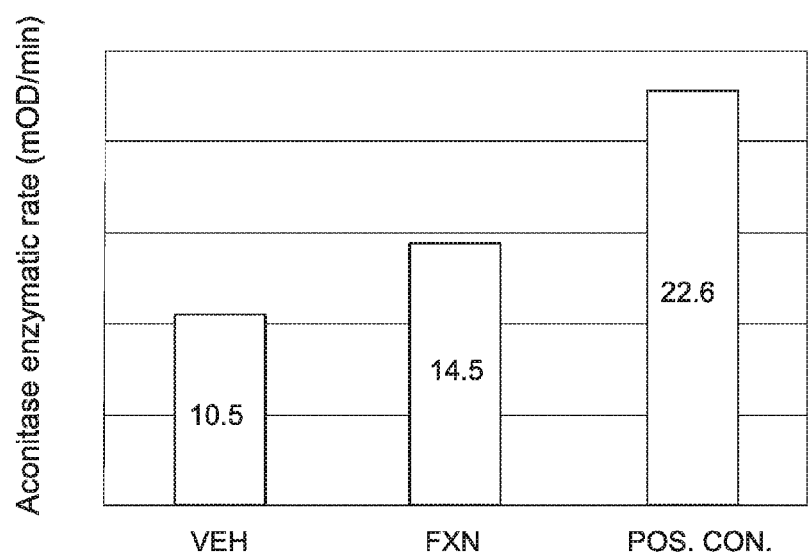

FIG. 10: Aconitase activity in fibroblasts obtained from Friedreich's ataxia patients following 48 hours incubation with TAT-MTScs-FRA A bar graph showing aconitase activity (mOD/min) of mitochondrial fractions obtained from Friedreich's ataxia patients' fibroblasts (F816) incubated for 48 hours with either 20 µg/ml TAT-MTScs-FRA protein or vehicle (FXN or VEH, respectively). HepG2 whole cells homogenate served as positive control (POS.CON). Abbreviations: kDa, kilodalton; TAT, transactivator of transcription; MTS, mitochondria targeting sequence; CS, citrate synthase; FXN, frataxin; Std, standard; VEH, vehicle, POS. CON., positive control.

Figure 11A:
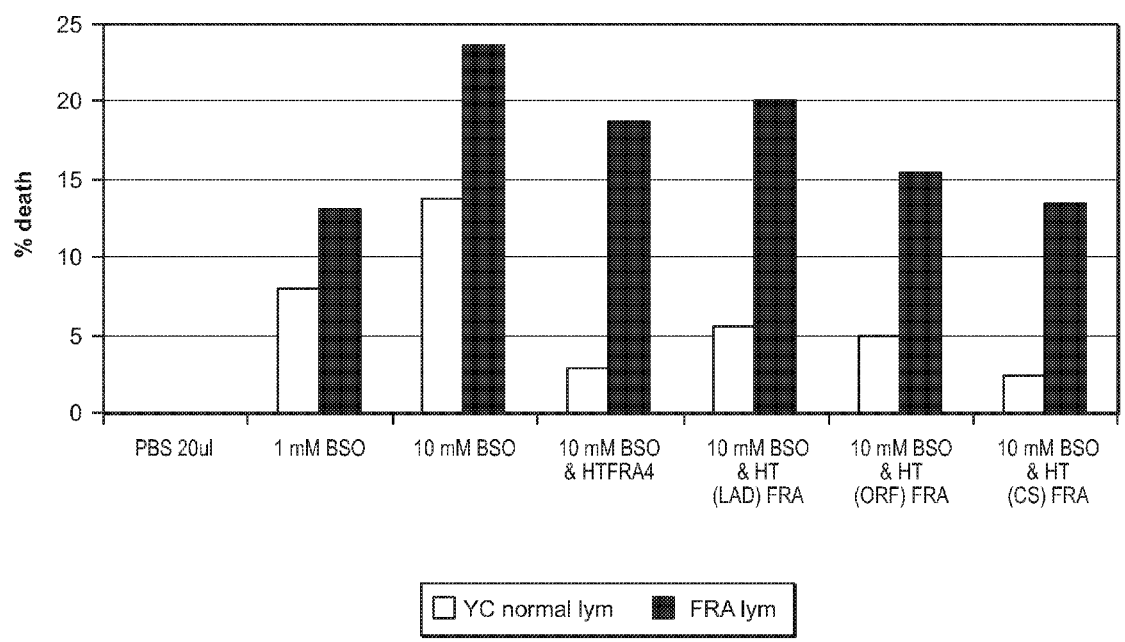
Figure 11B:
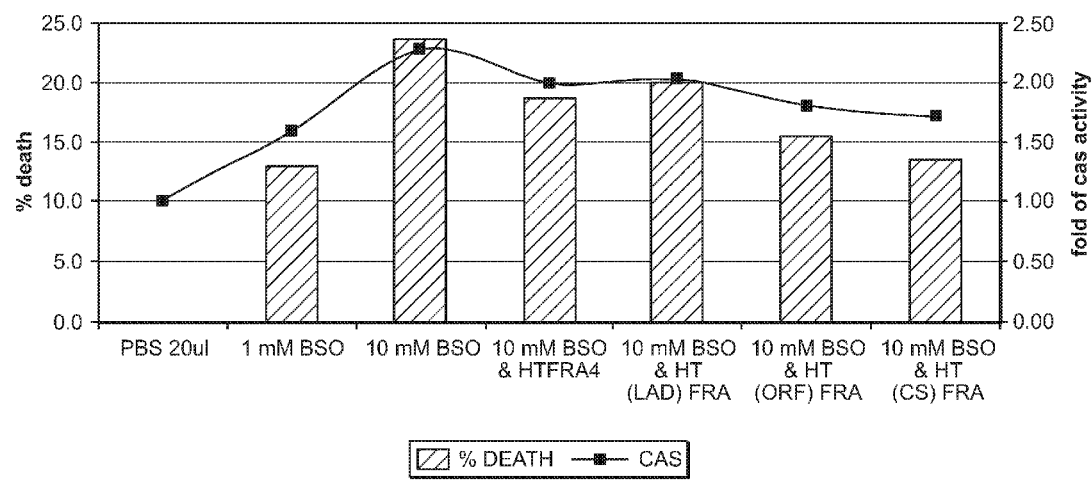

FIG. 11A-11B: TAT-MTS-FRA fusion proteins partially rescue cells from BSO-induced oxidative stress FIG. 11A presents a bar diagram showing percentage of cell death induced by L-Buthionine-sulfoximine (BSO). Normal lymphocytes or lymphocytes obtained from Friedreich's ataxia (FRDA) patients (Lym 43) were seeded, incubated for 5 hr with the various TAT-MTS-FRA fusion proteins, after which BSO at different concentrations was added for additional 48 hr. At the end of the incubation time, cell cultures were subjected to cell proliferation assays.

FIG. 11B presents a bar diagram showing percentage of cell death of Lym 43 induced by L-Buthionine-sulfoximine (BSO) correlated with caspase 3 activity within the cells, assessed using the Apo-ONE Homogeneous Caspase 3/7 Assay Kit (Promega). Experiments were carried in parallel with cell viability assays.

Abbreviations: %, percent; YC, normal lymphocytes; FRA lym, lymphocytes obtained from Friedreich's ataxia patients; HTFRA=TAT-MTSfra-FRA, HT(LAD)FRA=TAT-MTSlad-FRA, HT(ORF)FRA=TAT-MTSorf-FRA, HT(CS)FRA=TAT-MTScs-FRA; BSO, L-Buthionine-sulfoximine; and PBS, Phosphate buffered saline.

FIG. 12A-12D: TAT-MTS-FRA fusion proteins partially rescue fibroblasts obtained from patients from BSO-induced oxidative stress, a comparison FIG. 12A to FIG. 12D present bar diagrams of percentage of cell death induced by BSO in fibroblasts obtained from FRDA patients (Fib. 78). Cells were seeded, incubated for 24 hr with the TAT-MTSfra-FRA (FIG. 12A), TAT-MTScs-FRA (FIG. 12B), TAT-MTSlad-FRA (FIG. 12C) and with the TAT-MTSorf-FRA (FIG. 12D) fusion protein, after which BSO at different concentrations was added for additional 48 hr. At the end of the incubation time, cell cultures were subjected to cell proliferation assays.

Abbreviations: %, percent; PBS, Phosphate buffered saline; BSO, L-Buthionine-sulfoximine; HTF, TAT-MTSfra-FRA; MTS (cs), TAT-MTScs-FRA; MTS (LAD), TAT-MTSlad-FRA; MTS (ORF), TAT-MTSorf-FRA.

Figure 13A:
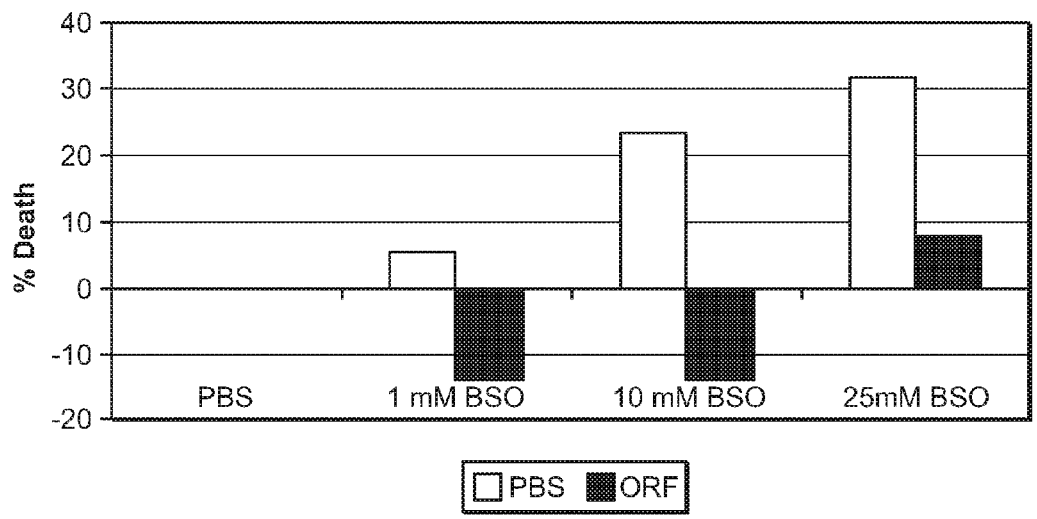
Figure 13B:
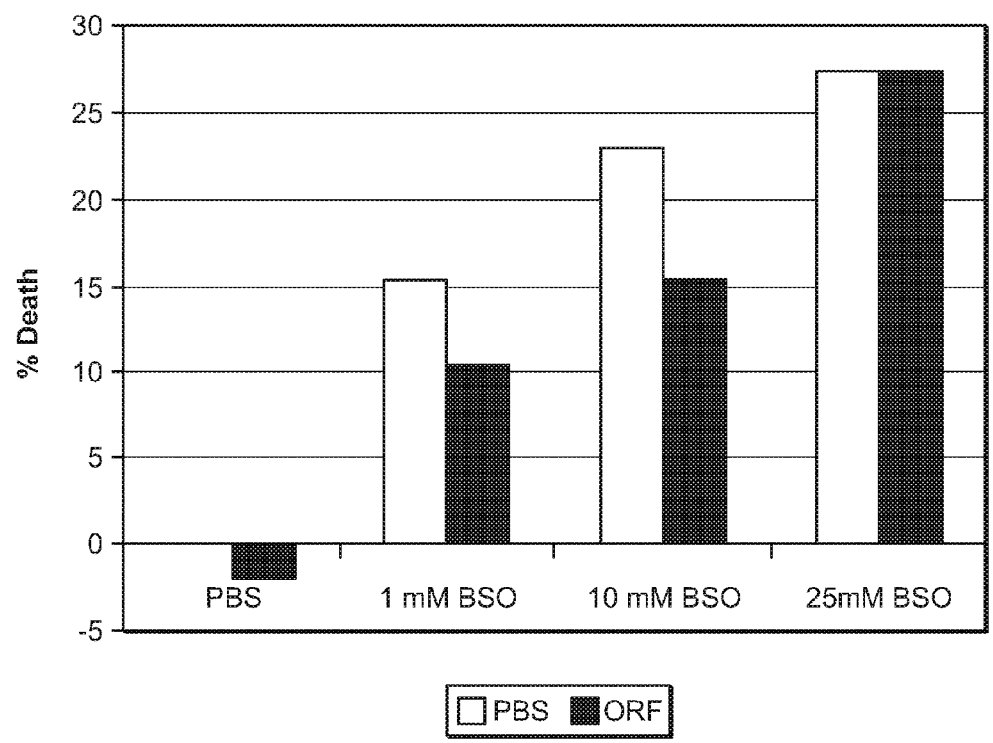

FIG. 13A-13B: TAT-MTSorf-FRA rescues lymphocytes and fibroblasts obtained from Friedreich's ataxia patients from BSO-induced oxidative stress FIG. 13A presents a bar diagram of percentage of cell death induced by BSO in fibroblasts obtained from FRDA patients (Fib. 78) and FIG. 13B presents a bar diagram of percentage of cell death induced by BSO in lymphocytes obtained from patients (Lym 43). Cells were seeded, incubated for 24 hr with the TAT-MTSorf-FRA fusion protein, after which BSO at different concentrations was added for additional 48 hr. At the of the incubation time, cell cultures were subjected to cell proliferation assays.

Abbreviations: PBS, Phosphate buffered saline; %, percent; BSO, L-Buthionine-sulfoximine; and ORF, C6ORF66.

Figure 14A:
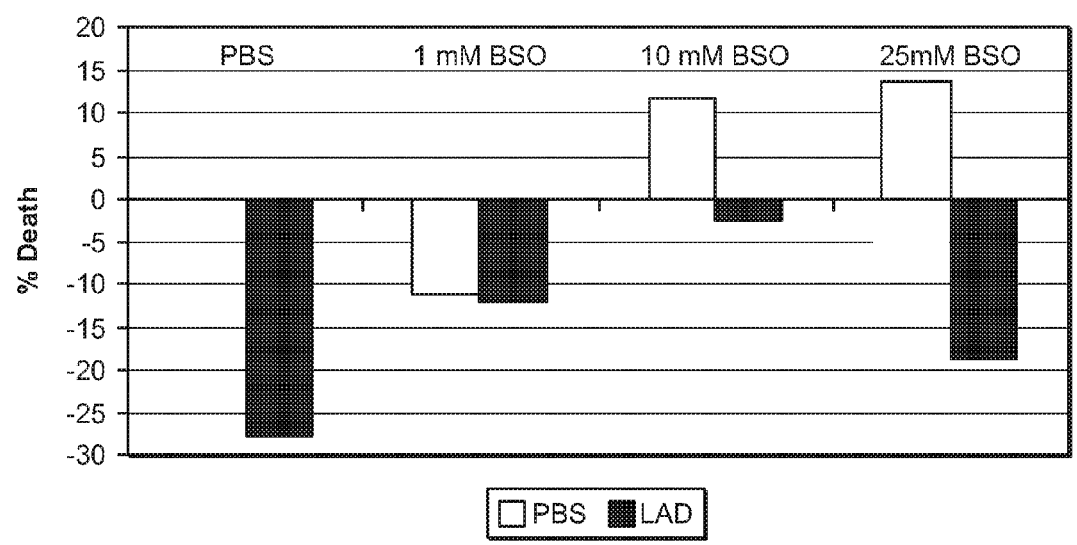
Figure 14B:
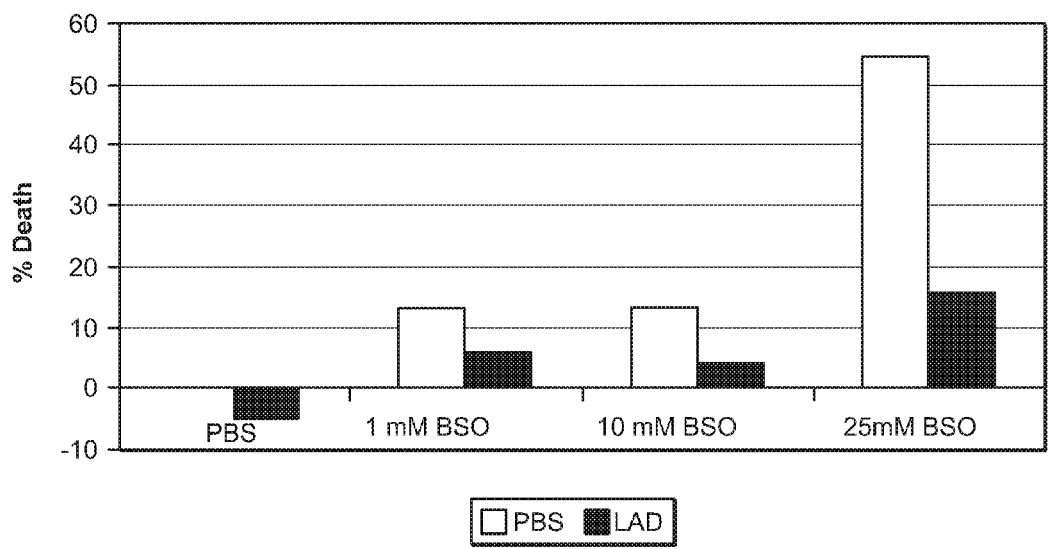
Figure 16A:
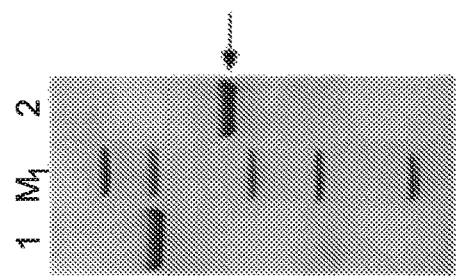
Figure 16B:
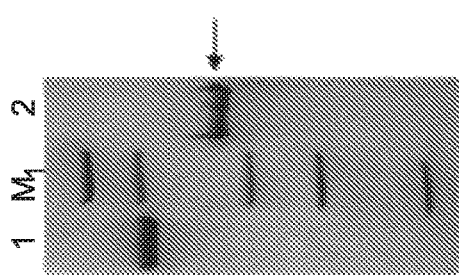
Figure 16C:
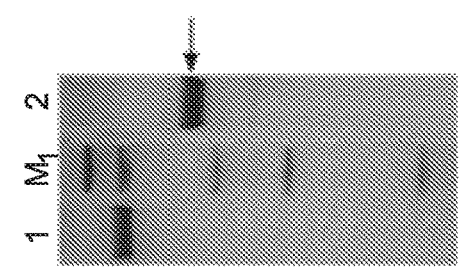
Figure 16D:
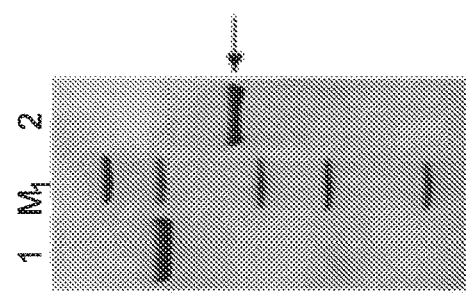
Figure 16E:
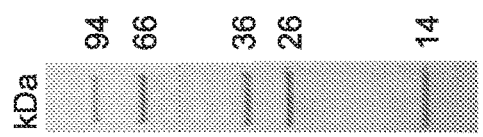

FIG. 14A-14B: TAT-MTSlad-FRA rescues fibroblasts obtained from patients from BSO-induced oxidative stress FIG. 14A and FIG. 14B present bar diagrams of percentage of cell death induced by BSO in fibroblasts obtained from FRDA patients (Fib. 78) of two representative experiments. Cells were seeded, incubated for 24 hr with the TAT-MTSlad-FRA fusion protein, after which BSO at different concentrations was added for additional 48 hr. At the of the incubation time, cell cultures were subjected to cell proliferation assays. Abbreviations: %, percent; PBS, Phosphate buffered saline; BSO, L-Buthionine-sulfoximine; LAD, lipoamide dehydrogenase.

FIG. 15A-15D: TAT-MTS-FRA fusion proteins constructs

FIG. 15A to FIG. 15D are schematic presentations of TAT-MTS-FRA fusion protein constructs comprising a HIV-1 transactivator of transcription (TAT) domain (boxed) fused to a GSDP linker (colored in grey) fused to a human mitochondria targeting sequence (MTS) of a human mitochondrial protein (double-underlined) selected from frataxin (MTSfra, FIG. 15A), citrate synthase (MTScs, FIG. 15B), lipoamide dehydrogenase (MTSlad, FIG. 15C) and C6ORF66 (MTSorf, FIG. 15D) fused to human frataxin (underlined).

FIG. 16A-16E: Expression and purification of TAT-MTS-OTC protein constructs

FIG. 16A to FIG. 16D are images of sodium dodecyl sulfate polyacrylamide gel electrophoresis (SDS PAGE) analysis of bacterially expressed TAT-MTS-OTC fusion protein constructs comprising ornithine transcarbamoylase (OTC, FIG. 16A), citrate synthase (CS, FIG. 16B), C6ORF66 (ORF, FIG. 16C) or lipoamide dehydrogenase (LAD FIG. 16D) as their MTS. The fusion protein construct is indicated with arrows. About 2 µg of each protein and BSA were analyzed on 4-20% gels, followed by Coomassie blue staining. Marker sizes are presented in FIG. 16E. Abbreviations: Ml, protein marker; kDa, kilodalton.

Figures 17A, 17B:
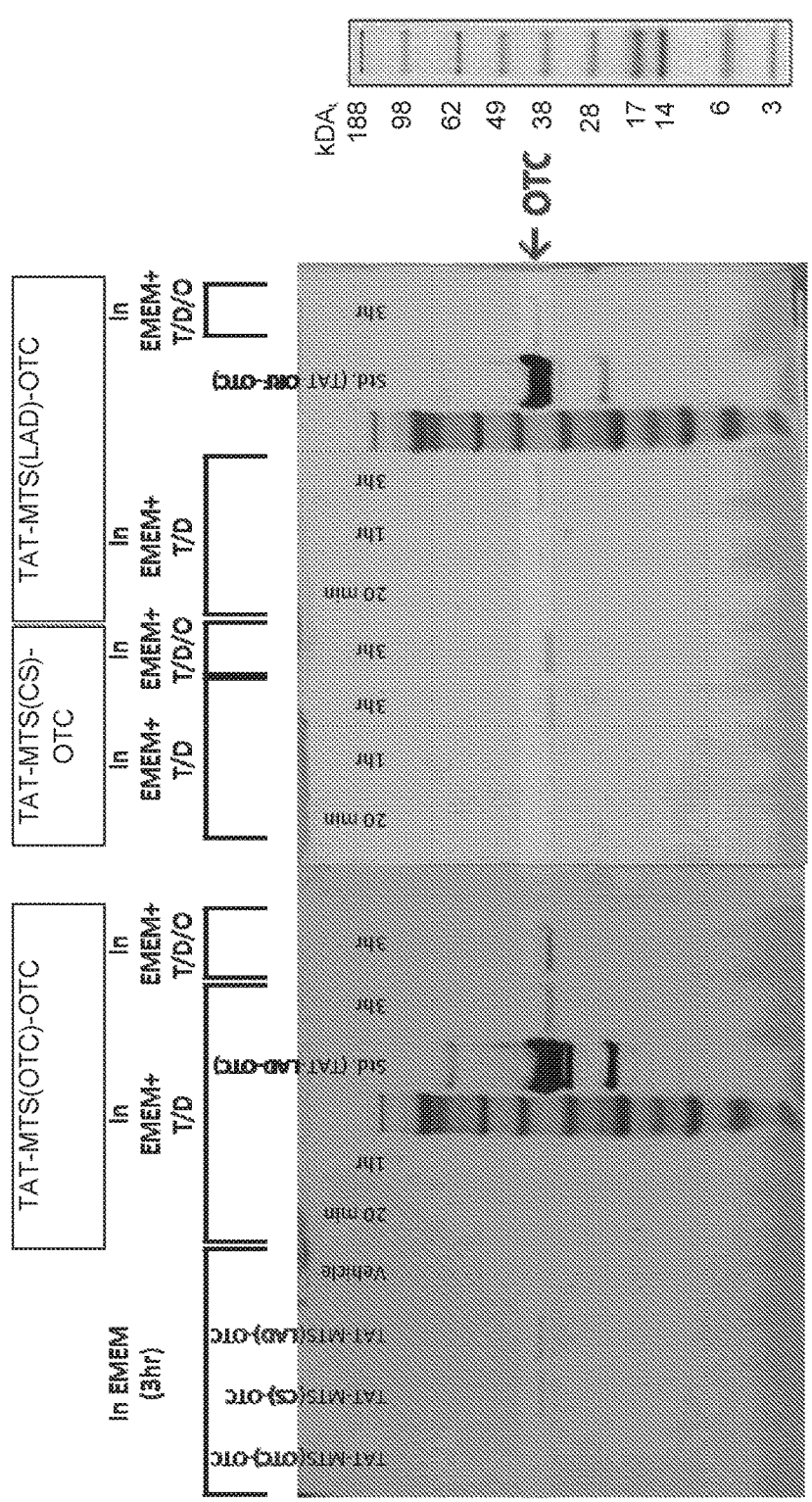

FIG. 17A-17B: Internalization of TAT-MTS-OTC protein constructs into mitochondria FIG. 17A is an image of a Western blot analysis performed for mitochondrial fractions of HepG2 cells incubated with 12 µg/ml of the TAT-MTS-OTC fusion protein TAT-MTSotc-OTC, TAT-MTScs-OTC, TAT-MTSlad-OTC or vehicle for 20 min, 1 and 3 hours in either Eagle's Minimum Essential Medium (EMEM) alone or EMEM supplemented with DMSO (D), Trehalose (T), or Ornithine (O), as indicated. The protein standards TAT-MTSlad-OTC or TAT-MTSorf-OTC (Std.) were run in parallel, sizes of the protein markers (M) are presented in FIG. 17B. Migration of the OTC fusion protein is marked by an arrow. Abbreviations: EMEM, Eagle's Minimum Essential Medium; TAT, transactivator of transcription; MTS, mitochondria targeting sequence; OTC, ornithine transcarbamoylase; CS, citrate synthase; LAD, lipoamide dehydrogenase; Std., standard; T/D, Trehalose/DMSO; T/D/O, Trehalose/DMSO/Ornithine; M, marker.

Figure 18A:
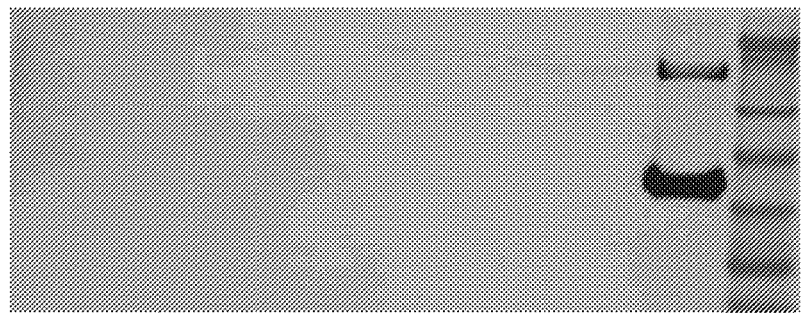
Figure 18B:
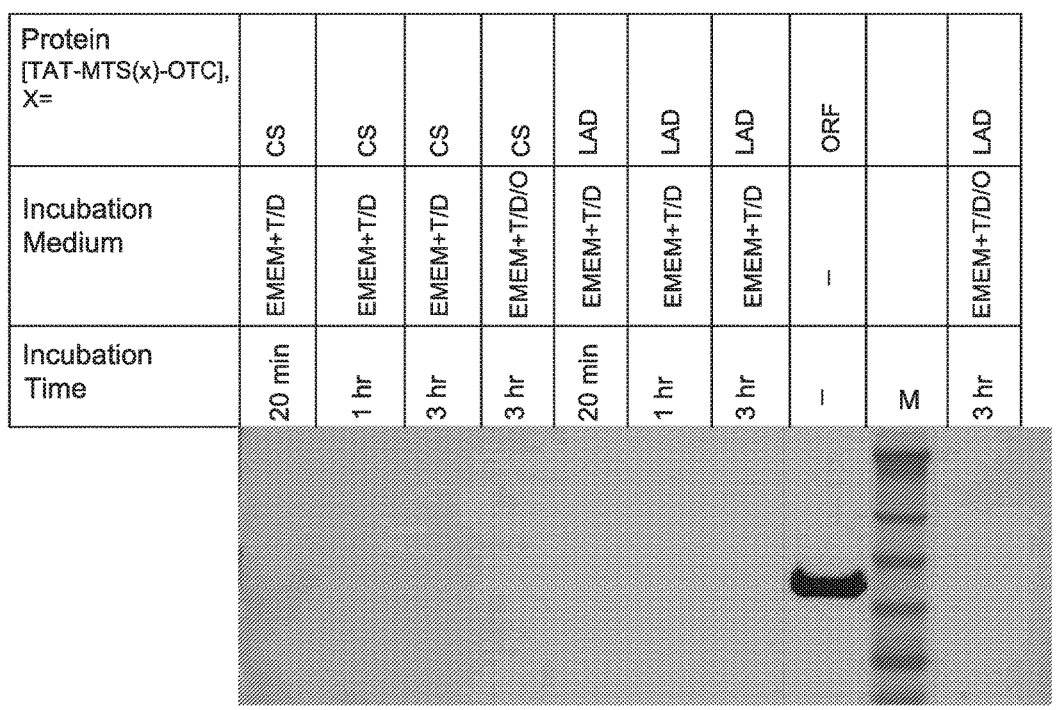

FIG. 18A-18B: Western blot analysis of cytosolic fractions of HepG2 cells incubated with TAT-MTS-OTC protein constructs FIG. 18A and FIG. 18B are images of Western blot analyses performed for cytosolic fractions of HepG2 cells incubated with 12 μg/ml of the TAT-MTS-OTC fusion protein TAT-MTSotc-OTC, TAT-MTScs-OTC, TAT-MTSlad-OTC or vehicle for 20 min, 1 and 3 hours in either EMEM alone or EMEM supplemented with DMSO (D), Trehalose (T), or Ornithine (O), as indicated. The protein standards TAT-MTScs-OTC or TAT-MTSorf-OTC (Std.) were run in parallel. Abbreviations: OTC, ornithine transcarbamoylase; CS, citrate synthase; LAD, lipoamide dehydrogenase; ORF, C6ORF66; EMEM, Eagle's Minimum Essential Medium; T/D, Trehalose/DMSO; T/D/O, Trehalose/DMSO/Ornithine; M, marker.

Figure 19:
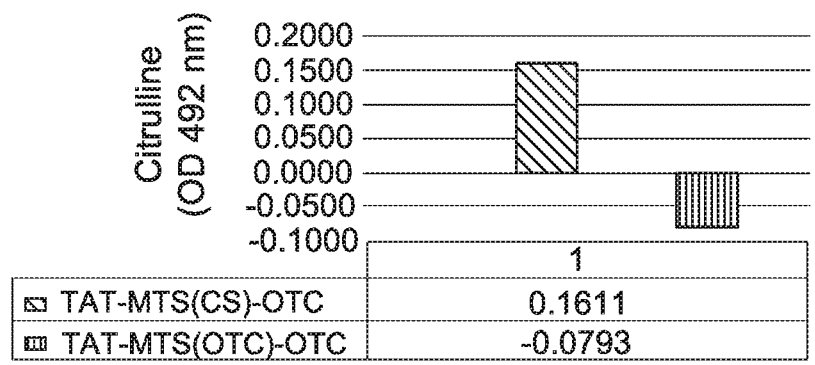

FIG. 19: In vitro enzymatic activity of OTC

A bar graph showing the level of in vitro enzymatic activities of the OTC protein constructs TAT-MTScs-OTC and TAT-MTSotc-OTC measured by detecting the net absorbance of citrulline at an optical density (O.D.) of 492 nm compared to a control.

Abbreviations: TAT, transactivator of transcription; MTS, mitochondria targeting sequence; OTC, ornithine transcarbamoylase; CS, citrate synthase.

Figure 20:
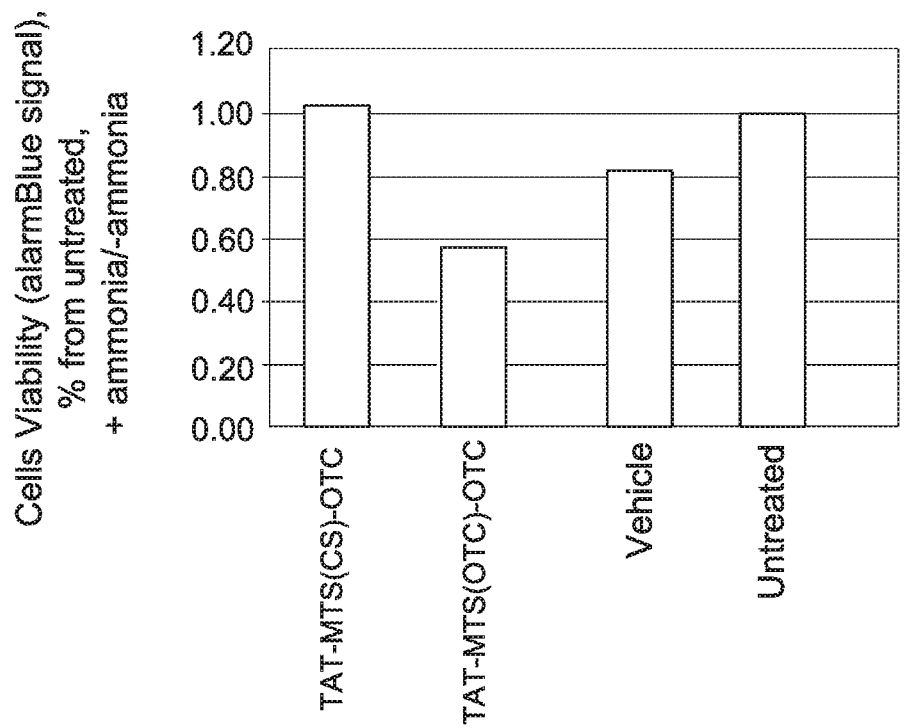

FIG. 20: Rescue from ammonia stress by OTC fusion proteins

A bar graph showing cell viability of HepG2 cells suffering from ammonia stress in the presence of 14 μg/ml of the OTC protein constructs TAT-MTScs-OTC, and TAT-MTSotc-OTC, compared to vehicle-treated and untreated cells. Florescence signal was calculated as the ratio between Ammonium chloride treated and non-treated cells.

Abbreviations: TAT, transactivator of transcription; MTS, mitochondria targeting sequence; CS, citrate synthase; OTC, ornithine transcarbamoylase.

DETAILED DESCRIPTION OF EMBODIMENTS

The presently disclosed subject matter relates to the preparation of various plasmid constructs encoding TAT-MTS-Frataxin fusion proteins, providing a basis of a wide-range therapeutic tool for delivering mitochondrial proteins into mitochondria.

The protein constructs described herein, comprising a mitochondrial protein as well as TAT and a specific mitochondrial targeting sequence (MTS), enabling the mitochondrial protein to cross both cellular and mitochondrial membranes, were expressed and purified and their biological activity was verified. Remarkably, the protein yield obtained for fusion protein constructs comprising an MTS which was other than the native MTS of the mitochondrial protein present in the fusion construct (e.g., a frataxin fusion protein construct with MTS heterologous to frataxin), was superior to the yield obtained for a frataxin fusion protein construct comprising the native MTS of frataxin.

As demonstrated below, the inventors show that various fusion proteins are able to enter the mitochondria within intact cells. In addition, the inventors show that the fusion proteins exhibit biological activity. For example, the various TAT-MTS-FRA fusion proteins were shown to rescue cells obtained from Friedreich ataxia patients as well as normal cells from oxidative stress, as demonstrated in the Examples below. Surprisingly, a superior protective effect was observed for fusion proteins carrying an MTS, which was other than the native MTS of the functional mitochondrial protein present in the fusion construct (i.e. a heterologous MTS) as compared to the effect demonstrated by the fusion protein constructs carrying the native MTS.

The presently disclosed subject matter provides fusion protein constructs comprising heterologous MTSs of human nuclear-encoded mitochondrial proteins that are classical MTS sequences, which are known to be removed upon entry to the mitochondria. By a non-limiting example, a delivery system as herein described comprising frataxin may be used for the treatment or alleviation of Friedreich's ataxia or any other disorder associated with a deficiency of frataxin or defective frataxin.

Thus, the presently disclosed subject matter provides a fusion protein comprising a HIV-1 transactivator of transcription (TAT) domain, a functional human mitochondrial protein and a human mitochondria targeting sequence (MTS) situated between said TAT domain and said functional human mitochondrial protein and wherein said human MTS is heterologous to said functional human mitochondrial protein.

The term "functional human mitochondrial protein" as used herein refers to any protein which is essential for a biological activity of mitochondria. A functional human mitochondrial protein may be a protein, which is active when present in the mitochondria by itself (per se) or a protein that when present in the mitochondria functions as a component of a mitochondrial multi-component complex (i.e. with other enzymes, co-factors, or proteins). Typically, a functional human mitochondrial protein is a protein, which, when absent, deficient or mutated, causes a mitochondrial disorder or is associated with a mitochondrial disorder.

In some specific embodiments, the functional mitochondrial protein refers to the full-length amino acid sequence of the protein. In other embodiments, the functional mitochondrial protein is a fragment of the full-length amino acid sequence, sufficient to provide the mitochondrial protein activity, either alone or as part of a multi-component complex, as appropriate.

In further embodiments, the functional human mitochondrial protein is a mutated derivative of said protein, wherein one or more of the native amino acid residues has been deleted, replaced or modified while still maintaining the mitochondrial functionally of the protein (alone or as part of a multi-component complex).

In the above and other embodiments, the functional human mitochondrial protein (also denoted "mature" protein) refers to a protein devoid of its mitochondrial targeting sequence (MTS). In other words, the fusion protein construct herein provided comprises a functional mitochondrial protein, which, upon entry to the mitochondria is cleaved off from the fusion protein construct in its mature, active (functional) state.

By way of non-limiting example, in the above and other embodiments of the disclosed subject matter, the functional human mitochondrial protein whose activity is supplied by a fusion protein of the present invention may be any one of human frataxin (the mature protein having the amino acid sequence denoted by SEQ ID NO. 26 and encoded by the nucleic acid sequence denoted by SEQ ID NO. 6), ornithine transcarbamoylase (OTC, the mature protein having the amino acid sequence denoted by SEQ ID NO. 39 and encoded by the nucleic acid sequence denoted by SEQ ID NO. 15), human Lipoamide Dehydrogenase (LAD), 2-oxoisovalerate dehydrogenase alpha subunit (Branched-Chain Keto Acid Dehydrogenase E1α) (NCBI Protein Database Accession No. P12694; OMIM:248600), 2-oxoisovalerate dehydrogenase beta subunit (Branched-Chain Keto Acid Dehydrogenase E1β; P21953), Acyl-CoA dehydrogenase, medium-chain specific (P1 1310; OMIM:201450), Acyl-CoA dehydrogenase, very-long-chain specific (P49748; OMIM:201475), Trifunctional enzyme alpha subunit (Long-chain 3 hydroxyacyl CoA Dehydrogenase or LCHAD) (P40939; OMIM:609015) (HADHA), Trifunctional enzyme beta subunit (Hydroxyacyl-CoA Dehydrogenase/3-Ketoacyl-CoA Thiolase/Enoyl-CoA Hydratase (P55084) (HADHB)), Pyruvate dehydrogenase E1 component beta subunit (P1 1177; OMIM:208800), and Pyruvate dehydrogenase E1 component alpha subunit (P08559; OMIM: 312170).

In some embodiments, the human mitochondrial protein is a functional mitochondrial protein per se and/or is a component of a mitochondrial multi-component complex.

As indicated above, the functional human mitochondrial protein of the disclosed subject matter may be a protein which is active when present in the mitochondria by itself (i.e. the protein per se is active) or a protein that when present in the mitochondria functions as a component of a mitochondrial multi-component complex (i.e. with other enzymes, co-factors, or proteins). The term "mitochondrial multi-component complex" as used herein refers to an enzyme that forms a complex with other enzymes or proteins that is essential for a biological activity of mitochondria.

As shown in the Examples below (FIG. 7), the fusion protein comprising a TAT and MTS sequences is cleaved upon entry into the mitochondria, and a mature active protein is obtained. The protein constructs provided by the presently disclosed subject matter thus allow a human mitochondrial protein, which is first covalently attached to TAT and MTS domains, to cross both cellular and mitochondrial membranes, and once inside the mitochondria, be processed by mitochondrial peptidases while retaining their biological activity and proper conformation. The delivery system described herein thus enables a human mitochondrial protein to retain its mitochondrial function per se or the integration thereof in a mitochondrial multi-component complex.

The mitochondrial multi-component complex encompassed by the present disclosure refers to a group of at least two different proteins assembled together in a specific ratio that functions in a coordinated fashion to catalyze a series of reactions. The function of a mitochondrial multi-component complex is dependent on its structure; thus, the proteins that compose the complex must properly fold and physically fit together in the proper configuration in order to efficiently catalyze the series of reactions.

In all embodiments, the functional human mitochondrial protein according to presently disclosed subject matter is cleaved off from the fusion protein construct upon entry to the mitochondria and resides therein at its mature, properly-folded active state. In some embodiments, the functional human mitochondrial protein may readily then integrate into a conformationally-sensitive mitochondrial multi-component complex.

By way of non-limiting example, the presently disclosed subject matter encompasses a mitochondrial multi-component complex which is any one of pyruvate dehydrogenase complex (PDHC), α-ketoglutarate dehydrogenase complex (KGDHC), and branched-chain keto-acid dehydrogenase complex (BCKDHC), the complexes of the respiratory chain, and those involved in fatty acid β-oxidation and the urea cycle. The complexes of the respiratory chain are complex I (NADH-ubiquinone oxidoreductase), complex II (succinate-ubiquinone oxidoreductase), complex III (ubiquinol-ferricytochrome C oxidoreductase), complex IV (Cytochrome C oxidoreductase), and complex V (FIFO ATPase) where each mitochondrial multicomponent complex represents a separate embodiment of the present invention.

As shown in Examples 1-3 below, the inventors have cloned, expressed and purified fusion protein constructs comprising the protein frataxin.

The mitochondrial protein human frataxin (FXN) is an essential and highly conserved protein expressed in most eukaryotic organisms that appears to function in mitochondrial iron homeostasis, notably the de novo biosynthesis of iron-sulfur (Fe—S) cluster proteins and heme biosynthesis. The exact function of FXN has not been defined but recent studies suggest that FXN functions as an allosteric activator with $Fe^{2+}$ for Fe—S cluster biosynthesis. The absence of FXN is associated with a loss of activity in Fe—S-containing proteins, such as aconitase as well as with the disease Friedreich ataxia.

Precursor FXN protein (23.1 kDa, 210 amino acids) comprises an 80 amino acid mitochondrial targeting sequence (MTS) at its amino (N) terminus. Within mitochondria, the precursor FXN protein is processed in two steps by the mitochondrial matrix processing peptidase (MPP). It has been shown that the intermediate form of FXN is formed by cleavage at residue 42 by the MPP, and the resulting form of FXN (FXN42-210) has been shown to be cleaved at amino acid 81, yielding a mature, 130 amino acid protein, with a predicted molecular weight of 14.2 kDa.

As described above, Friedreich ataxia is an autosomal recessive degenerative disorder characterized by ataxia, areflexia, sensory loss, weakness, scoliosis, and cardiomyopathy. A deficiency of frataxin in cells leads to decreased activities of mitochondrial iron-sulfur cluster-containing enzymes, to an accumulation of iron in the mitochondrial matrix, increased sensitivity to oxidative stress, as well as to impaired adenosine triphosphate (ATP) production.

In the above and other embodiments of the presently disclosed subject matter, frataxin refers to human frataxin and any biologically active fragments and derivatives thereof, which is devoid of its natural (native) MTS sequence. Non limiting examples for mature human frataxin are given by the accession number Q16595[81-210] and as indicated in Table 1 below, where the amino acid sequence of mature human frataxin is as set forth in SEQ ID NO. 26 and the nucleic acid sequence encoding therefor is as set forth in SEQ ID NO. 6.

Notably, as shown in Example 4 below, a TAT-MTS-frataxin fusion protein was demonstrated by the inventors to enter mitochondria of human intact BJAB cells. Analysis of sub-cellular fractions of these cells, in order to separate the mitochondria from the cytosol, verified that the various frataxin fusion protein constructs (i.e. TAT-MTSlad-FRA, TAT-MTSfra-FRA, TAT-MTScs-FRA, and TAT-MTSorf-FRA) were indeed successfully delivered into the mitochondria. Surprisingly, among the fusion proteins carrying a heterologous MTS, the MTS of citrate synthase (MTScs) was shown by the inventors to be delivered into the mitochondria in the most efficient manner.

Delivery of fusion proteins comprising a mitochondrial protein into the mitochondria has far-reaching therapeutic beneficial implications for treatment of mitochondrial disorders in general, and delivery of frataxin into mitochondria has specific therapeutic benefit for treatment of Friedreich's ataxia in particular.

As noted above, ornithine transcarbamoylase (OTC, also called ornithine carbamoyltransferase) is also encompassed by the presently disclosed subject matter. OTC is a protein having enzymatic activity that catalyzes the reaction between carbamoyl phosphate (CP) and ornithine (Orn) to form citrulline (Cit) and phosphate ($P_i$). In mammals OTC is located in the mitochondria and is part of the urea cycle.

OTC is a trimer, and the active sites thereof are located at the interface between the protein monomers, emphasizing the importance of proper folding to the mitochondrial activity of the protein. Deficiency in OTC results in an increase in ammonia level, leading to neurological problems.

As demonstrated in the appended Examples, fusion protein constructs according to the invention comprising OTC and its native MTS as well as fusion protein constructs comprising OTC and a heterologous MTS were able to internalize into the mitochondria in HepG2 cells (Example 9). Interestingly, the internalization ability of the fusion protein constructs comprising an MTS that is heterologous to OTC was slightly higher than the internalization ability of the fusion protein construct comprising the native MTS of OTC. Fusion protein constructs comprising the protein OTC were also shown to be active. As shown in FIG. 20, the level of cell viability in the presence of fusion protein constructs comprising OTC and citrate synthase as the MTS was similar to the level of cell viability for cells which were not exposed to ammonium chloride (which served as a model for ammonia stress conferred by defective or missing OTC).

Furthermore, the level of cell viability in the presence of a fusion protein construct comprising OTC and citrate synthase as the MTS was higher from the level of cell viability in cells treated with the fusion protein construct comprising the native MTS of OTC.

Thus, in the above and other embodiments of the disclosed subject matter, the functional human mitochondrial protein is specifically any one of frataxin and ornithine transcarbamoylase (OTC). In some embodiments, the nucleic acid encoding the mature OTC protein is denoted by SEQ ID NO. 15. In other embodiments the OTC mature protein of the present disclosure has the amino acid sequence denoted by SEQ ID NO. 39.

As indicated above, the presently disclosed subject matter provides a fusion protein comprising a HIV-1 transactivator of transcription (TAT) domain, a functional human mitochondrial protein and a human mitochondria targeting sequence (MTS) situated between said TAT domain and said functional mitochondrial protein and wherein said human MTS is heterologous to said functional protein.

Most of the proteins directed to the mitochondria are synthesized with a mitochondrial targeting (or translocation) sequence (MTS), which allows their import from the cytoplasm into mitochondria through the translocation machinery. Once entering the mitochondria, the MTS is recognized and cleaved off, allowing for proper processing and, if necessary, assembly into mitochondrial enzymatic complexes.

Thus, as used herein, the term "mitochondria targeting sequence", MTS or "mitochondria translocation sequence" refers to an amino acid sequence capable of causing the transport into the mitochondria of a protein, peptide, amino acid sequence, or compound attached thereto, and any biologically active fragments thereof. MTSs used in the fusion protein constructs in accordance with the presently disclosed subject matter, which are situated N-terminal to the functional mitochondrial protein, are typically from about 15 to about 40 amino acids in length, including from about 3 to about 5 nonconsecutive basic amino acid (arginine/lysine) residues, often with several serine/threonine residues but without acidic amino acid (asparate/glutamate) residues. In their molecular structure, these MTSs are able to form strong basic amphipathic α-helices that are essential for efficient mitochondrial transportation.

In other words, presently disclosed is a fusion protein as herein defined, wherein said functional human mitochondrial protein is C-terminal to said human mitochondria targeting sequence (MTS).

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

In the above and other embodiments, the MTS is human MTS, namely MTS of a human mitochondrial protein.

In the above and other embodiments of the presently disclosed subject matter the MTS comprises from about 15 to about 40 amino acid residues, including from about 3 to about 5 nonconsecutive (i.e. which are not covalently linked one to the other in a sequential manner) basic amino acid residues, and optionally from about 1 to about 3 or 4 or 5 serine/threonine residues.

The term "amino acid residues" as used herein refers to naturally occurring and synthetic amino acids, as well as amino acid analogs and amino acid mimetics that can function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "amino acid analogs and amino acid mimetics" refers to compounds that have the same fundamental chemical structure as a naturally occurring amino acid. Such analogs have modified R groups or modified peptide backbones, but retain the same basic chemical structure as a naturally occurring amino acid. Amino acids may be referred to herein by either their commonly known three letter symbols or by the one-letter symbols recommended by the IUPAC-IUB Biochemical Nomenclature Commission.

It is well known in the art that amino acid residues may be divided according to their chemical properties to various groups, inter alia, on the basis of similarity in polarity, charge, solubility, hydrophobicity, hydrophilicity, and/or the amphipathic nature of the residues involved.

For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q). "Basic" amino acids are selected from the group consisting of Histidine (H), lysine (K) and Arginine (R), which are polar and positively charged at pH values below their pKa's, and are very hydrophilic.

As indicated above, the presently disclosed subject matter encompasses human mature frataxin and any biologically active fragments and derivatives thereof, which is devoid of its natural (native) MTS sequence. By the term "biologically active fragments and derivatives" it is meant any variations, including deletion, substitution and/or insertion of one or more amino acid residues in the amino acid sequences of mature frataxin (or in the nucleic acid encoding therefor), for example 1, 2, 3, 4, 5 or more amino acid residues, in accordance with the presently disclosed subject matter which would not alter the biological activity of frataxin.

The invention further relates to DNA constructs comprising the nucleic acid sequence of the presently disclosed subject matter or biologically functional fragments and derivatives thereof. The constructs of the presently disclosed subject matter may further comprise additional elements such as promoters, regulatory and control elements, translation, expression and other signals, operably linked to the nucleic acid sequence of the invention.

It is known that each mitochondrial enzyme produced in the cytoplasm and transported into the mitochondria is produced as a precursor protein, carrying its natural MTS. Thus, the precursor mitochondrial protein already has its native MTS. However, this naturally occurring sequence in the precursor protein may be exchanged with any other known MTS.

As exemplified herein, the fusion protein constructs comprising frataxin or ornithine transcarbamoylase prepared by the inventors further comprised the MTS of lipoamide dehydrogenase (MTSlad, of the amino acid sequence denoted by SEQ ID NO. 24 and encoded by the nucleic acid sequence denoted by SEQ ID NO. 5), C6ORF66 (MTSorf, of the amino acid sequence denoted by SEQ ID NO. 25 and encoded by the nucleic acid sequence denoted by SEQ ID NO. 4), or of citrate synthase (MTScs, of the amino acid sequence denoted by SEQ ID NO. 23 and encoded by the nucleic acid sequence denoted by SEQ ID NO. 3).

Alternatively, fusion protein constructs comprising frataxin or ornithine transcarbamoylase prepared by the inventors comprised respectively the native MTS of frataxin (MTSfra, of the amino acid sequence denoted by SEQ ID NO. 22 and encoded by the nucleic acid sequence denoted by SEQ ID NO. 2) or the native MTS of ornithine transcarbamoylase (MTSotc, of the amino acid sequence denoted by SEQ ID NO. 38 and encoded by the nucleic acid sequence denoted by SEQ ID NO. 37).

In addition, the inventors showed that fusion protein constructs comprising frataxin and a MTS sequence that is not the native MTS of frataxin (i.e. heterologous MTS) were superior to the frataxin fusion protein construct comprising the native MTS, based on the higher yield obtained for fusion protein constructs comprising heterologous MTS during the expression and purification stages.

Surprisingly, fusion protein constructs comprising frataxin and a heterologous MTS were also demonstrated by the inventors to have an enhanced biological activity as compared to the frataxin fusion protein construct comprising the native MTS (Example 5). In particular, a fusion protein construct comprising frataxin and citrate synthase MTS showed the highest effect in reducing toxicity of BSO (FIG. 11A and FIG. 11B). As shown in Example 4 below, the fusion protein construct comprising frataxin and citrate synthase MTS also showed the highest ability of being delivered into mitochondria among the exemplified constructs comprising heterologous MTS.

Figure 12A:
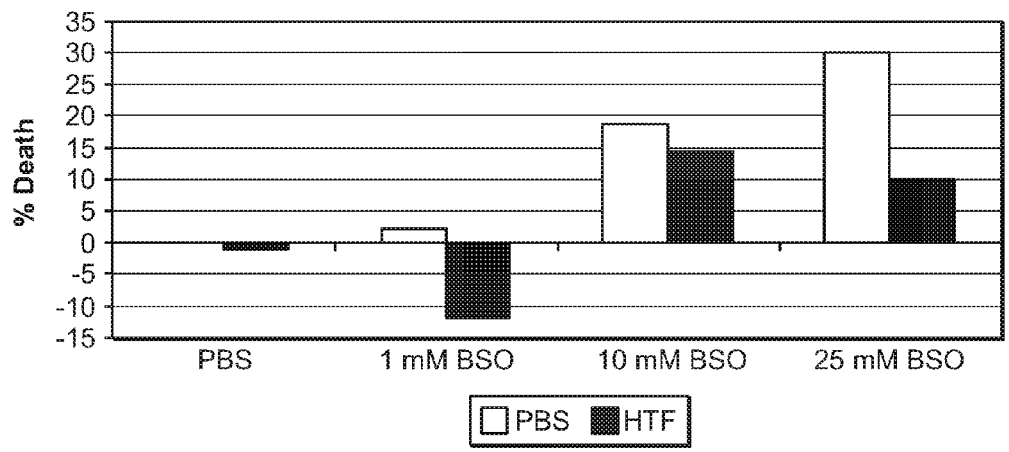
Figure 12B:
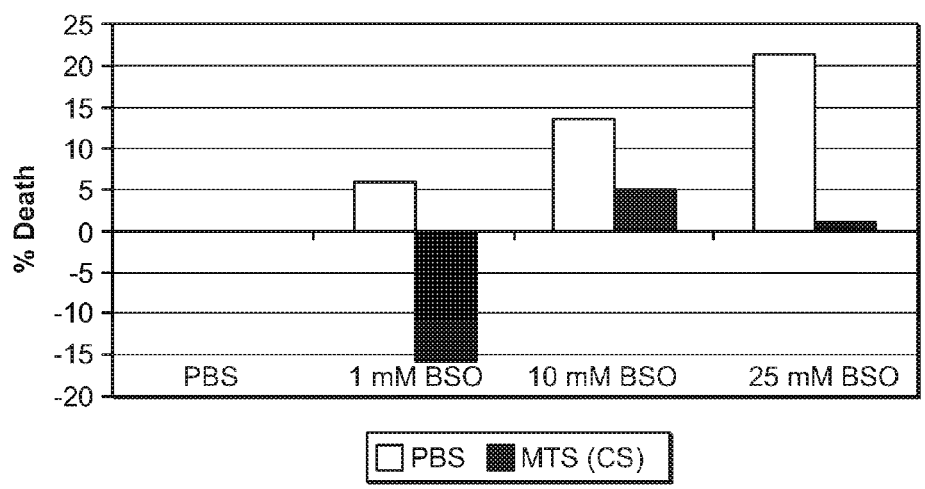
Figure 12C:
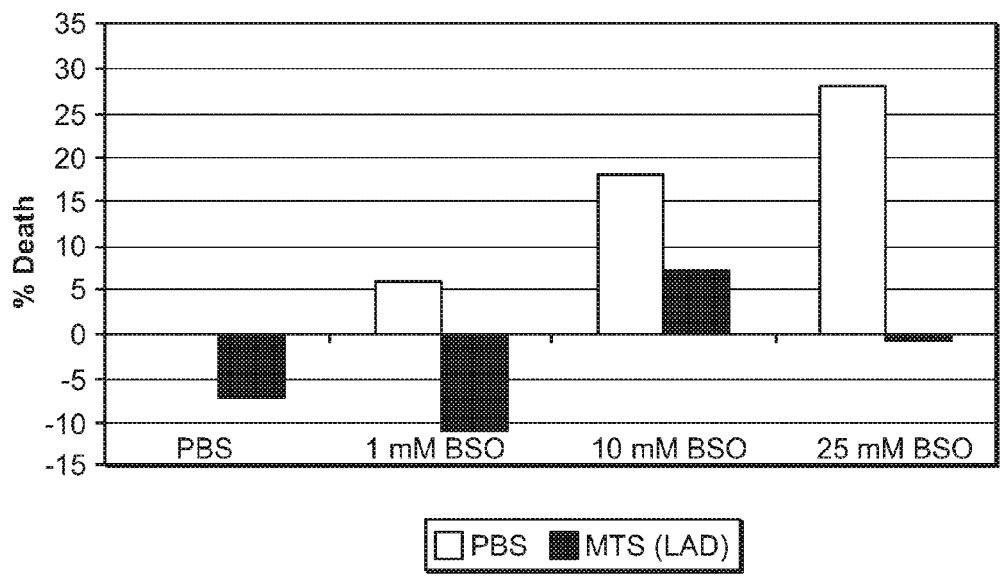
Figure 12D:
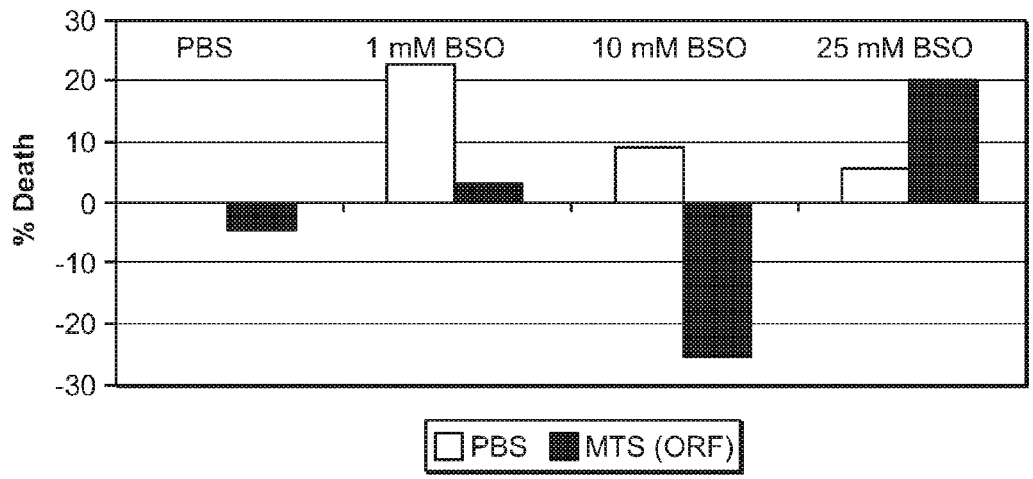

Consistent with the above results, a fusion protein construct comprising frataxin and another heterologous MTS, namely the MTS of lipoamide dehydrogenase (LAD), was also demonstrated by the inventors to have an enhanced biological activity as compared to the frataxin fusion protein construct comprising the frataxin native MTS, as demonstrated in FIG. 12C. As evident from FIG. 12, the biological activity of this fusion protein construct was comparable to the biological activity of the fusion protein construct comprising the citrate synthase MTS.

As detailed above, it is known that FXN mRNA is translated into a precursor polypeptide that is transported to the mitochondrial matrix and processed to at least two forms, namely FXN42-210 and FXN81-210, where FXN42-210 is the transient processing intermediate and FXN81-210 represents the mature protein. In other words, the transient frataxin polypeptide FXN42-210 includes a portion of the native frataxin MTS, whereas the FXN81-210 is the mature protein per se, devoid of its native MTS. Without wishing to be bound by theory, by using a heterologous MTS in fusion protein constructs comprising frataxin, mature frataxin is expected to be released from the fusion protein at a single step, thereby raising the biological availability of this protein in the mitochondria compared to fusion protein constructs comprising frataxin and its native MTS.

Thus, the MTS encompassed by the presently disclosed subject matter is any human MTS that is encoded by the nuclear DNA, translated (produced) in the cytoplasm and transported into the mitochondria and which is not the native N-terminal MTS sequence of the functional protein present in the fusion protein construct according to the invention. In other words, the MTS sequence is other than the native N-terminal MTS sequence of the functional protein, i.e. is heterologous thereto. The various MTS may be exchangeable for each mitochondrial enzyme among themselves. Each possibility represents a separate embodiment of the present invention.

As used herein, the term "heterologous" when referring to MTS fused to the functional human mitochondrial protein according to the present disclosure, is to be taken to mean MTS obtained from another (distinct) mitochondrial protein, i.e. MTS which is not the naturally occurring MTS of the said functional protein.

By way of a non-binding example, the heterologous MTS according to the present disclosure is a MTS which is heterologous to the mitochondrial protein frataxin, or to the mitochondrial protein ornithine transcarbamoylase (OTC) as exemplified herein, which may be, but is not limited to, the MTS of any human mitochondrial protein, e.g. lipoamide dehydrogenase (MTSlad, of the amino acid sequence denoted by SEQ ID NO. 24 and encoded by the nucleic acid sequence denoted by SEQ ID NO. 5), C6ORF66 (MTSorf, of the amino acid sequence denoted by SEQ ID NO. 25 and encoded by the nucleic acid sequence denoted by SEQ ID NO. 4), and of citrate synthase (MTScs, of the amino acid sequence denoted by SEQ ID NO. 23 and encoded by the nucleic acid sequence denoted by SEQ ID NO. 3), which are non-limiting examples.

Thus, in embodiments of the presently disclosed fusion protein constructs, the MTS can be any one of human mitochondrial citrate synthase MTS having the amino acid sequence denoted by SEQ ID NO. 23, the human lipoamide dehydrogenase MTS having the amino acid sequence denoted by SEQ ID NO. 24, the MTS of the human C6ORF66 gene product having the amino acid sequence denoted by SEQ ID NO. 25 and the MTS of human mitochondrial GLUD2 encoded by the nucleic acid sequence denoted by SEQ ID NO. 16.

In other embodiments of the presently disclosed fusion protein construct, the MTS is any one of human mitochondrial citrate synthase MTS having the amino acid sequence denoted by SEQ ID NO. 23 and the human lipoamide dehydrogenase MTS having the amino acid sequence denoted by SEQ ID NO. 24.

In some embodiments disclosed is a fusion protein comprising a HIV-1 transactivator of transcription (TAT) domain fused to human frataxin and a human mitochondria targeting sequence (MTS) of a human mitochondrial protein selected from lipoamide dehydrogenase (LAD) and citrate synthase (CS) situated between said TAT domain and said frataxin, wherein said frataxin is C-terminal to said MTS of human lipoamide dehydrogenase or human citrate synthase.

In other embodiments disclosed is a fusion protein comprising a HIV-1 transactivator of transcription (TAT) domain fused to human ornithine transcarbamoylase (OTC) and a human mitochondria targeting sequence (MTS) of a human mitochondrial protein selected from lipoamide dehydrogenase (LAD) and citrate synthase (CS) situated between said TAT domain and said OTC, wherein said OTC is C-terminal to said MTS of human lipoamide dehydrogenase or human citrate synthase.

As indicated above, the fusion protein according to the presently disclosed subject matter comprises a HIV-1 transactivator of transcription (TAT) domain, located at the N-terminus of the fusion protein, N-terminal to the MTS as defined above, which in turn is situated N-terminal to the functional human mitochondrial protein (see FIG. 1 for a schematic presentation).

As used herein, the term HIV-1 transactivator of transcription (TAT) domain refers to a protein transduction domain which is an 11-amino-acid (residues 47-57) arginine- and lysine-rich portion of the HIV-I Tat protein having the amino acid sequence YGRKKRRQRRR as set forth in SEQ ID NO. 21. TAT-fusion protein constructs are known in the art to be introduced into cultured cells, intact tissue, and live tissues and cross the blood-brain barrier (BBB). TAT fusion proteins are also known to traverse mitochondrial membranes [13].

The presently disclosed subject matter also encompasses any fragments of the above defined TAT domain. For example, a TAT domain according to the presently disclosed subject matter may comprise from about 3 to about 11 (e.g. 4-11, 5-11, 6-11, 7-11, 8-11, 9, 10 or 11) sequential amino acid residues of the HIV-I Tat protein having the amino acid sequence YGRKKRRQRRR (SEQ ID NO. 21).

In some embodiments, the fragment of the above defined TAT domain comprise 9 sequential amino acid residues of the HIV-I Tat protein, having the amino acid sequence of RKKRRQRRR, as set forth in SEQ ID NO. 27 and encoded by the nucleic acid sequence denoted by SEQ ID NO. 1, which was used in the preparation of the fusion protein constructs exemplified below.

Thus, in this and other embodiments of the presently disclosed subject matter, the fusion protein comprises a TAT domain at its N-terminus and a functional mitochondrial protein at its C-terminus, both covalently linked (fused) to an MTS that is situated between said TAT domain and said functional mitochondrial protein. In other words, the disclosure provides a protein construct comprising an N-terminal TAT fused to N-terminal of MTS fused to N-terminal of functional protein, as schematically presented in FIG. 1 for frataxin.

The fusion protein according to the presently disclosed subject matter may be prepared by any method known to a skilled artisan. By example, the fusion protein as herein defined may be prepared as exemplified below, by standard molecular biology and cloning techniques.

The term "fusion protein" in the context of the invention concerns a sequence of amino acids, predominantly (but not necessarily) connected to each other by peptidic bonds. The term "fused" in accordance with the fusion protein of the invention refers to the fact that the amino acid sequences of at least three different origins, namely, the TAT domain, the sequence of the heterologous mitochondrial targeting domain (MTS) and the functional mitochondrial protein, are linked to each other by covalent bonds either directly or via an amino acid linker joining (bridging, conjugating, covalently binding) the amino acid sequences. The fusion may be by chemical conjugation such as by using state of the art methodologies used for conjugating peptides.

The fusion protein in the context of the invention may also optionally comprise at least one linker covalently joining different domains of the fusion protein construct.

The term "linker" in the context of the invention concerns an amino acid sequence of from about 4 to about 20 amino acid residues positioned between the different fusion protein domains and covalently joining them together. For example, a linker in accordance with the invention may be 4, 5, 6, 7, 8, 9, 10, 11, 12, 13, 14, 15, 16, 17, 18, 19 or 20 amino acid long. Linkers are often composed of flexible amino acid residues, for example but not limited to glycine and serine so that the adjacent protein domains are free to move relative to one another. The term "linker" can be interchangeably used with "spacer".

The design of a linker that enables proper folding of the various domains of a protein is well known in the art. A non-binding example of a linker is the amino acid sequence GSDP (Gly-Ser-Asp-Pro) as denoted by SEQ ID NO. 32, which was used in the Examples below to construct the fusion proteins His TAT MTS(cs) 81-210 FRA (denoted by SEQ ID NO. 17), His TAT MTS(fra) 81-210 FRA (denoted by SEQ ID NO. 18), His TAT MTS(lad) 81-210 FRA (denoted by SEQ ID NO. 19) and His TAT MTS(orf) 81-210 FRA (denoted by SEQ ID NO. 20) as well as several of the fusion proteins comprising OTC.

Thus in some embodiments the present disclosure relates to a fusion protein as herein defined further comprising a linker covalently linking said TAT domain to said MTS sequence.

The fusion protein in the context of the invention may also optionally comprise at least one methionine (M) residue at its N-terminus, as in the case of the exemplified fusion proteins below. The methionine is positioned N-terminal to the TAT domain.

Fusion may also be achieved by recombinant techniques, i.e. by construction of a nucleic acid sequence coding for the entire the fusion protein (coding for all segments) so that essentially all the bonds are peptidic bonds.

In order to facilitate purification of the protein constructs described herein, fusion protein constructs in accordance with the invention may also comprise an N-terminal tag (e.g. His tag as exemplified below, Glutathione S-transferase (GST), Maltose-Binding Protein (MBP), FLAG octapeptide, to name but few), which may be removed or retained in the final fusion construct. Such tags are normally cleaved off from the fusion protein upon entry to the mitochondria, along with the TAT and MTS sequences.

In some embodiments, the amino acid sequence of a fusion protein according to the invention is as set forth in SEQ ID NO. 17, namely His TAT MTS(cs) FRA, SEQ ID NO. 19, namely His TAT MTS(lad) FRA, SEQ ID NO. 20, namely, His TAT MTS(orf) FRA, SEQ ID NO. 45, namely, His TAT MTS(cs) OTC, SEQ ID NO. 46, namely, His TAT MTS(orf) OTC as well as SEQ ID NO. 47, namely, His TAT MTS(lad) OTC.

Fusion protein constructs in accordance with the invention may also be prepared without an N-terminal tag. In some embodiments, the amino acid sequence of a fusion protein according to the invention is as set forth in SEQ ID NO. 28, namely TAT MTS(cs) FRA, SEQ ID NO. 30, namely TAT MTS(lad) FRA, SEQ ID NO. 31, namely, TAT MTS(orf) FRA, SEQ ID NO. 49, namely TAT MTS(cs) OTC, SEQ ID NO. 50, namely TAT MTS(orf) OTC, as well as in SEQ ID NO. 51, namely TAT MTS(lad) OTC.

Therefore the present disclosure further encompasses a fusion protein having the amino acid sequence denoted by SEQ ID NO. 30, comprising a HIV-1 transactivator of transcription (TAT) domain having the amino acid sequence denoted by SEQ ID NO. 27 fused to human frataxin having the amino acid sequence denoted by SEQ ID NO. 26 and a mitochondria targeting sequence (MTS) of human lipoamide dehydrogenase having the amino acid sequence denoted by SEQ ID NO. 24, said MTS situated between said TAT domain and said frataxin and is linked to said TAT domain via a linker having the amino acid sequence denoted by SEQ ID NO. 32, and wherein said frataxin is C-terminal to said MTS of human lipoamide dehydrogenase.

In some embodiments the fusion protein as herein defined has the amino acid sequence denoted by SEQ ID NO. 28, comprising a HIV-1 transactivator of transcription (TAT) domain having the amino acid sequence denoted by SEQ ID NO. 27 fused to human frataxin having the amino acid sequence denoted by SEQ ID NO. 26 and a mitochondria targeting sequence (MTS) of human citrate synthase having the amino acid sequence denoted by SEQ ID NO. 23, said MTS situated between said TAT domain and said frataxin, and is linked to said TAT domain via a linker having the amino acid sequence denoted by SEQ ID NO. 32, and wherein said frataxin is C-terminal to said MTS of human citrate synthase.

In some embodiments the fusion protein as herein defined has the amino acid sequence denoted by SEQ ID NO. 45, comprising a HIV-1 transactivator of transcription (TAT) domain having the amino acid sequence denoted by SEQ ID NO. 27 fused to human ornithine transcarbamoylase (OTC) having the amino acid sequence denoted by SEQ ID NO. 39 and a mitochondria targeting sequence (MTS) of human citrate synthase having the amino acid sequence denoted by SEQ ID NO. 23, said MTS situated between said TAT domain and said OTC, and is linked to said TAT domain via a linker having the amino acid sequence denoted by SEQ ID NO. 32, and wherein said OTC is C-terminal to said MTS of human citrate synthase.

The presently disclosed subject matter further provides a composition comprising a physiologically acceptable carrier and as an active ingredient a fusion protein as herein defined.

In specific embodiments the presently disclosed subject matter provides a composition comprising as an active ingredient a fusion protein having the amino acid sequence denoted by SEQ ID NO. 45, denoted by SEQ ID NO. 30, or having the amino acid sequence denoted by SEQ ID NO. 28 and a physiologically acceptable carrier.

Also provided by the presently disclosed subject matter is a pharmaceutical composition comprising a pharmaceutically acceptable carrier and as an active ingredient a fusion protein construct as herein defined.

The "composition" as herein defined generally comprises a buffering agent, an agent which adjusts the osmolarity thereof, and optionally, one or more pharmaceutically (or physiologically) acceptable carriers, diluents, additives and excipients as known in the art. Supplementary active ingredients can also be incorporated into the compositions. The pharmaceutically acceptable carrier can be solvent or dispersion medium containing, for example, water, ethanol, polyol (for example, glycerol, propylene glycol and liquid polyethylene glycol, and the like), suitable mixtures thereof, and vegetable oils. Each carrier should be physiologically or pharmaceutically acceptable, as the case may be, in the sense of being compatible with the other ingredients and not injurious to the patient.

The additives may be but are not limited to at least one of a protease inhibitor, for example phenylmethanesulfonylfluoride or phenylmethylsulfonyl fluoride (PMSF), Nafamostat Mesylate, 4-(2-Aminoethyl)benzenesulfonyl fluoride hydrochloride (AEBSF), Bestatin, Pepstatin A, E-64, Leupeptin, 1,10-Phenanthroline and any other protease inhibitor known in the art.

The "pharmaceutical compositions" of the presently disclosed subject matter are compositions as described above, comprising pharmaceutically acceptable carriers, diluent, adjuvant and/or excipients and/or additives as known in the art.

The presently disclosed subject matter further provides a pharmaceutical composition as herein defined for treating or alleviating a mitochondrial disorder.

The term "mitochondrial disorder" as encompassed by the presently disclosed subject matter refers to a group of systemic diseases caused by inherited or acquired damage to the mitochondria causing an energy shortage within those areas of the body that consume large amounts of energy such as the liver, muscles, brain, and the heart. The result is often liver failure, muscle weakness, fatigue, and problems with the heart, eyes, and various other systems.

The mitochondrial disorder may be any one of frataxin deficiency which causes or is associated with Friedreich's ataxia; a deficiency in OTC (X-linked recessive genetic disorder caused by non-conservative mutations in the OTC gene); disorder associated with LAD deficiency; or the mitochondrial metabolic disorder is Complex I deficiency (OMIM:252010). Complex I deficiency can be caused by a mutation in any of the subunits thereof. Alternatively, the Complex I deficiency is caused by a mutation in a gene selected from NDUFV1 (OMIM: 161015), NDUFV2 (OMIM:600532), NDUFS1 (OMIM: 157655), NDUFS2 (OMIM:602985), NDUFS3 (OMIM:603846), NDUFS4 (OMIM:602694), NDUFS6 (OMIM:603848), NDUFS7 (OMIM:601825), NDUFS8 (OMIM:602141), and NDUF A2 (OMIM: 602137).

In other embodiments, the mitochondrial disorder is Complex IV deficiency (Cytochrome C oxidase; OMIM:220110). Complex IV deficiency can be caused by a mutation in any of the subunits thereof. In another embodiment, the Complex IV deficiency is caused by a mutation in a gene selected from the group consisting of MTCO1 (OMIM:516030), MTCO2 (OMIM:516040), MTCO3 (OMIM:516050), COX1O (OMIM:602125), COX6B1 (OMIM: 124089), SCO1 (OMIM:603644), FASTKD2 (OMIM:612322), and SC02 (OMIM:604272).

In other embodiments, the mitochondrial disorder is a neurodegenerative disease. As provided herein, compositions of the present invention exhibit the ability to traverse the blood-brain barrier (BBB).

In further embodiments of the presently disclosed subject matter, the mitochondrial disorder is selected from the group consisting of encephalopathy and liver failure that is accompanied by stormy lactic acidosis, hyperammonemia and coagulopathy. In other embodiments, the mitochondrial disorder is selected from the group consisting of Ornithine Transcarbamoylase deficiency (hyperammonemia) (OTCD), Carnitine O-palmitoyltransferase II deficiency (CPT2), Fumarase deficiency, Cytochrome c oxidase deficiency associated with Leigh syndrome, Maple Syrup Urine Disease (MSUD), Medium-Chain Acyl-CoA Dehydrogenase deficiency (MCAD), Acyl-CoA Dehydrogenase Very Long-Chain deficiency (LCAD), Trifunctional Protein deficiency, Progressive External Ophthalmoplegia with Mitochondrial DNA Deletions (POLG), DGUOK, TK2, Pyruvate Decarboxylase deficiency, and Leigh Syndrome (LS). In another embodiment, the mitochondrial metabolic disorder is selected from the group consisting of Alpers Disease; Barth syndrome; beta-oxidation defects; carnitine-acyl-carnitine deficiency; carnitine deficiency, co-enzyme Q1O deficiency, Complex II deficiency (OMIM:252011), Complex III deficiency (OMIM: 124000), Complex V deficiency (OMIM: 604273), LHON-Leber Hereditary Optic Neuropathy; MM-Mitochondrial Myopathy; LIMM-Lethal Infantile Mitochondrial Myopathy; MMC-Maternal Myopathy and Cardiomyopathy, NARP-Neurogenic muscle weakness, Ataxia, and Retinitis Pigmentosa; Leigh Disease; FICP-Fatal Infantile Cardiomyopathy Plus, a MELAS-associated cardiomyopathy, MELAS-Mitochondrial Encephalomyopathy with Lactic Acidosis and Strokelike episodes; LDYT-Leber's hereditary optic neuropathy and Dystonia; MERRF-Myoclonic Epilepsy and Ragged Red Muscle Fibers; MHCM-Maternally inherited Hypertrophic CardioMyopathy; CPEO-Chronic Progressive External Ophthalmoplegia; KSS-Kearns Sayre Syndrome; DM-Diabetes Mellitus; DMDF Diabetes Mellitus+Deafness; CIPO-Chronic Intestinal Pseudoobstruction with myopathy and Ophthalmoplegia; DEAF-Maternally inherited DEAFness or aminoglycoside-induced DEAFness; PEM-Progressive encephalopathy; SNHL-SensoriNeural Hearing Loss; Encephalomyopathy; Mitochondrial cytopathy; Dilated Cardiomyopathy; GER-Gastro intestinal Reflux; DEMCHO-Dementia and Chorea; AMDF-Ataxia, Myoclonus; Exercise Intolerance; ESOC Epilepsy, Strokes, Optic atrophy, and Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardio myopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young, and MNGIE.

Each mitochondrial disease represents an embodiment of the present invention.

In the above and other embodiments, the presently disclosed subject matter provides a pharmaceutical composition as herein defined for use in the treatment of Friedreich's ataxia or any other disorder associated with deficiency of frataxin or defective frataxin or for use in the treatment of a disorder associated with a deficiency of OTC or with defective OTC.

In still further embodiments, the presently disclosed subject matter provides a pharmaceutical composition for the treatment of Friedreich's Ataxia by intravenous administration to a subject in need thereof, said composition comprising a therapeutically effective amount of a fusion protein as herein defined.

In specific embodiments the presently disclosed subject matter provides a pharmaceutical composition for the treatment of Friedreich's Ataxia by intravenous administration to a subject in need thereof, said composition comprising a therapeutically effective amount of a fusion protein having the amino acid sequence denoted by SEQ ID NO. 30 or having the amino acid sequence denoted by SEQ ID NO. 28.

In further specific embodiments the presently disclosed subject matter provides a pharmaceutical composition for the treatment of Friedreich's Ataxia by intravenous administration to a subject in need thereof, said composition comprising a therapeutically effective amount of a fusion protein having the amino acid sequence denoted by SEQ ID NO. 30.

In still further specific embodiments the presently disclosed subject matter provides a pharmaceutical composition for the treatment of Friedreich's Ataxia by intravenous administration to a subject in need thereof, said composition comprising a therapeutically effective amount of a fusion protein having the amino acid sequence denoted by SEQ ID NO. 28.

The presently disclosed subject matter further provides a fusion protein according to the invention for use in a method for the treatment of a mitochondrial disorder.

In the above and other embodiments of the presently disclosed subject matter the functional human mitochondrial protein is frataxin for use in a method for the treatment or alleviation of Friedreich's ataxia or any other disorder associated with deficiency of frataxin or defective frataxin.

In the above and other embodiments of the presently disclosed subject matter the functional human mitochondrial protein is OTC for use in a method for the treatment or alleviation of a disorder associated with a deficiency of OTC or with defective OTC.

As shown below in Example 7, the inventors have shown that fusion proteins comprising TAT, MTS and frataxin (TAT-MTS-FRA) were able to partially rescue cells obtained from Friedreich's ataxia patients, as well as normal cells, from oxidative stress, exhibiting a clear biological activity of the fusion protein constructs of the presently disclosed subject matter.

L-Buthionine sulphoximine (BSO) is an inhibitor of gamma-glutamylcysteine synthetase (gamma-GCS) and, consequently lowers tissue glutathione (GSH) concentrations. GSH plays an important role in cellular defense against a wide variety of toxic electrophiles via the formation of thioether conjugates. Therefore, BSO was used by the inventors to model oxidative stress, through its ability to inhibit de novo glutathione synthesis, thereby depleting an important component of these cells' intrinsic defenses against reactive oxygen species (ROS) and allowing for the accumulation of ROS produced by natural cell processes, known to result in cell death.

It is known that Friedreich ataxia cells are extremely sensitive to BSO-induced oxidative stress compared with normal cells because they lack Frataxin, and thus are used as an in vitro model of the long-term consequences of absent Frataxin.

As shown in the Examples below, oxidative stress was induced with various concentrations of BSO in cells obtained from patients as well as in normal healthy cells and the effect of the various TAT-MTS-FRA fusion proteins on cell death was measured. As can be seen in FIG. 11, BSO caused cell death of normal lymphocytes as well as of cells obtained from Friedreich ataxia patients. However, cells obtained from patients were more sensitive to BSO-induced oxidative stress, consistent with previous findings. Most importantly, the various TAT-MTS-FRA fusion proteins, which were added a few hours before oxidative stress induction, were demonstrated to partially rescue both normal lymphocytes as well as patients' cells from cell death. This partial rescue was determined by both reduction in cell death and by reduction in caspase 3 activity.

Surprisingly, as also shown in FIG. 11, at least two out of the three fusion proteins carrying a heterologous MTS (namely, MTSorf and MTScs) demonstrated a superior protective effect with respect to the effect demonstrated by the fusion protein carrying the native MTS.

In addition, in an independent comparative experiment shown in FIG. 12, in which the effect of the various TAT-MTS-FRA fusion proteins on oxidative stress was examined, a fusion protein carrying another heterologous MTS, namely, MTSlad also demonstrated a superior protective effect with respect to the effect demonstrated by the fusion protein carrying the native MTS (FIG. 12C).

Thus the presently disclosed subject matter further provides a method for treating or alleviating a mitochondrial disorder, said method comprising the step of administering to a subject in need of such treatment a therapeutically effective amount of the fusion protein as defined herein, thereby treating a mitochondria disorder.

In the above and other embodiments, the method for treating or alleviating a mitochondrial disorder according to the invention is wherein said functional protein is frataxin or OTC, and the mitochondrial disorder is Friedreich's ataxia or any other disorder associated with deficiency of frataxin or defective frataxin or respectively, a disorder associated with a deficiency of OTC or with defective OTC.

The term "treat" or "treatment" or forms thereof as herein defined means to prevent worsening or arrest or alleviate or cure the disease or condition in a subject in need thereof. Thus the term "treatment", "treating" or "alleviating" in the context of the intention does not refers to complete curing of the diseases, as it does not change the mutated genetics causing the disease. This term refers to alleviating at least one of the undesired symptoms associated with the disease, improving the quality of life of the subject, decreasing disease-caused mortality, or (if the treatment in administered early enough) preventing the full manifestation of the mitochondrial disorder before it occurs, mainly to organs and tissues that have a high energy demand. The treatment may be a continuous prolonged treatment for a chronic disease or a single, several or multiple administrations for the treatment of an acute condition such as encephalopathy and liver failure that is accompanied by stormy lactic acidosis, hyperammonemia and coagulopathy.

Notably, in the case of metabolic or mitochondrial disorders there is no need to restore protein activity back to 100%, but rather raise it above a certain energetic threshold which can vary from patient to patient depending on basal protein activity.

In addition, treatment of mitochondrial disorders using replacement therapy is necessarily more complex than replacement of a cytosolic gene product and must consider not only the need to target and cross multiple membranes in mitochondria, but also the fact that many proteins in the mitochondria act as multi-component complexes which require appropriate assembly in order to integrate properly.

Additionally, many of the mitochondrial gene defects cause severe neurologic symptoms as the primary or most prominent phenotype, and, as mentioned above, drug delivery across the BBB is difficult.

Therapeutic formulations may be administered in any conventional route and dosage formulation. Formulations typically comprise at least one active ingredient, as defined above, together with one or more acceptable carriers thereof. Thus, administration can be any one of intravenous, intraperitoneal, intramuscular and intratechal administration. Oral administration is also contemplated.

The term "therapeutically effective amount" (or amounts) of the peptide for purposes herein defined is determined by such considerations as are known in the art in order to cure or at least arrest or at least alleviate the medical condition.

As indicated above, in the case of metabolic or mitochondrial disorders it is not required to restore protein activity back to 100%. Rather, raising the protein activity to above a certain energetic threshold, which can vary from patient to patient depending on basal protein activity, can be sufficient to provide a therapeutic effect.

In some embodiments the therapeutically effective amount may be determined for each patient individually, based on the patient's basal protein activity. The patient's basal protein activity, or the level of protein activity may in turn be determined using any method known in the art, for example, by subjecting a biological sample obtained from a patient (e.g. blood (white cells), skin fibroblast cells, whole tissue biopsies) to an in vitro enzymatic assay or immunohistochemistry or any specific imaging such as PET.

In some embodiments the functional human mitochondrial protein is OTC and the patient's basal OTC activity is determined by liver biopsy.

In some embodiments the therapeutically effective amount according to the presently disclosed subject matter is between about 0.5 mg/kg to about 2.0 mg/kg body weight of the subject in need thereof which is the Human Equivalent Dose (HED) of an effective amount in mice of between about 7 mg/kg to about 25 mg/kg.

Thus in specific embodiments disclosed is a pharmaceutical composition as herein defined wherein the therapeutically effective amount administered is from about 0.5 mg/Kg to about 2 mg/Kg body weight of said subject.

As used herein, the term "subject in need" is to be taken to mean a human suffering from a mitochondrial disorder as herein defined.

In the above and other embodiments, the method for treating or alleviating a mitochondrial disorder according to the invention further comprises administering an additional therapeutic agent.

The term "additional therapeutic agent" as herein defined refers to any agent that is administered in addition to the fusion protein according to the invention in order to alleviate the symptoms associated with the disease or disorder the treatment of which is desirable. In the above and other embodiments of the disclosed subject matter, the fusion protein of the invention and said additional therapeutic agent are administered simultaneously. Alternatively or additionally, said fusion protein and said additional therapeutic agent are administered at different time points, at different intervals between administrations, for different durations of time, or in a different order.

The disclosed subject matter further provides a method for introducing a functional mitochondrial protein into mitochondria of a subject, said method comprising the step of administering to a subject in need of such treatment a therapeutically effective amount of the fusion protein as defined herein, thereby introducing a functional mitochondrial protein into the mitochondria of a subject in need thereof.

In some embodiments the functional human mitochondrial protein thereby introduced restores at least partial activity of the wild type human mitochondrial protein, for example at least 5%, at least 10%, at least 15%, at least 20%, at least 30%, at least 40%, at least 50%, at least 60%, at least 70%, at least 80%, at least 90% or up to 100% of the activity of a wild type human mitochondrial protein.

Thus, the disclosed subject matter further provides a method for restoring at least in part activity of a defective or deficient or unfunctional human mitochondrial protein in a subject in need, by administering a fusion as herein disclosed to said subject. The human mitochondrial protein may be active per se, or may be a member of a mitochondrial protein complex.

By another one of its aspects, the disclosed subject matter further provides a method for alleviating oxidative stress in a subject in need thereof, said method comprising the step of administering to a subject in need of such treatment a therapeutically effective amount of the fusion protein as herein defined, thereby alleviating oxidative stress in said subject.

The term "oxidative stress" as herein defined refers to an imbalance between the systemic manifestations of reactive oxygen species (ROS) and an ability of a biological system to readily detoxify the reactive intermediates or to repair the resulting damage. Disturbances in the normal redox state of cells can cause toxic effects through the production of peroxides and free radicals that damage all components of the cell. In addition, since some reactive oxidative species act as cellular messengers in redox signaling, accumulation of ROS can cause disruptions in normal mechanisms of cellular signaling. In humans, oxidative stress is thought to be involved in the development of various disorders and conditions, among which are cancer, Parkinson's disease, Alzheimer disease to name but a few.

It is appreciated that certain features of the presently disclosed subject matter, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless defined otherwise, all technical and scientific terms used herein have the same meaning as commonly understood by one of ordinary skill in the art to which this invention is related. The following terms are defined for purposes of the invention as described herein.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.
Experimental Procedures
Cell Cultures Lymphocytes (Lym 43) and fibroblasts (Fib. 78 and Fib. 65, F816) from Friedreich's ataxia patients were obtained from Coriell Cell Repositories (Camden, N.J.) and grown at the recommended medium (fibroblasts in Eagle's Minimum Essential Medium (EMEM) with Earle's salts and non-essential amino acids, and lymphocytes in Roswell Park Memorial Institute (RPMI) Medium 1640 with 2 m M L-glutamine, all supplemented with 15% fetal bovine serum not inactivated). Human BJAB cells (EBV-negative Burkitt's lymphoma cells; provided by Hanna Ben-Bassat, Hadassah Medical Center, Jerusalem, Israel) were grown in RPMI medium supplemented with 20% heat-inactivated fetal calf serum (FCS), 2 mM L-glutamine, 100 U/mL penicillin, and 100 µg/mL streptomycin. Normal lymphocytes [20] were grown in RPMI 1640 supplemented with 10% fetal calf serum (FCS) and antibiotics as above. HepG2 cells (ATCC: HB-8065) were grown in EMEM supplemented with 10% FCS, 2 mM L-Glutamine, non-essential amino acids, antibiotics and sodium pyruvate. All culture cells were grown in 37° C. with 5% $CO_2$. All media and supplements were purchased from Biological Industries (Bet Ha'emek, Israel). The cells were kept in a humidified atmosphere with 5% $CO_2$ at 37° C. All cultures were tested for mycoplasma contamination and were found to be negative.
Cloning of the Plasmids Encoding the Fusion Proteins
His-TAT-MTSfra-FRA The plasmid His-TAT-LAD was prepared as previously reported [23] and was cut with BamHI and XhoII to remove the LAD sequence, thus obtaining a vector fragment encoding the His-TAT domain. The full-length frataxin was generated by PCR using a frataxin clone (purchased from Open Biosystem, Ltd., clone no. 4842134) as a template and a pair primers covering the whole sequence, including its native MTS, 5'-CGCGGATCCGTGGACTCTCGGGCGCCG-3' (forward) and 5'-ACGCTCGAGTCAAGCATCTIITCCG-GAATAGGC-3' (reverse), as denoted by SEQ ID NO. 7 and SEQ ID NO. 8, respectively. The PCR fragment was cut with BamHI and XhoII and ligated with the vector fragment, thus obtaining the plasmid encoding the His-TAT-MTSfra-FRA fusion protein.

His-MTSlad-FRA

The plasmid encoding the His-TAT-MTSfra-FRA was cut with BamHI and BsaI to remove the MTSfra sequence. The MTSlad (the native MTS of lipoamide dehydrogenase) was obtained by PCR using the plasmid His-TAT-LAD [23] as a template and the following pair of primers: 5'-CGCGGATC-CACAGAGCTGGAGTCGTGTGTA-3' (forward) and 5'-CATAGG-TGGTCTCATCTAGAGAGCCTGGGTGGC-CCAAAGTTCCAGATGCGTAAGTTCT CAGAGGCA-3' (reverse) as denoted by SEQ ID NO. 9 and SEQ ID NO. 10, respectively. The PCR product was cut with BamHI and BsaI and ligated to the vector fragment thus obtaining the plasmid encoding the His-TAT-MTSlad-FRA fusion protein.

His-TAT-MTSorf-FRA

The plasmid encoding the His-TAT-MTSfra-FRA was cut with BamHI and BsaI to remove the MTSfra sequence as described above. The MTSorf (the native MTS of the protein C6ORF66 assembly factor) was obtained by PCR using the plasmid His-TAT-ORF as a template and the following pair of primers: 5'-CGCGGATCCGGGAGCACTAGTGAT-TCGC-3' (forward) and 5'-CATAGGTG GTCTCATCTA-GAGAGCCTGGGTGGCCCAAAGTTCCA-GAAGAGGGGTGTCTG GGAGCGA-3' (reverse), as denoted by SEQ ID NO. 11 and SEQ ID NO. 12, respectively. The PCR product was cut with BamHI and BsaI and ligated to the vector fragment thus obtaining the plasmid encoding the His-TAT-MTSorf-FRA fusion protein.

His-TAT-MTScs-FRA

The plasmid encoding the His-TAT-MTSfra-FRA was cut with BamHI and BsaI to remove the MTSfra sequence as described above. The MTScs (the native MTS of the protein citrate synthase) was generated by synthesizing two oligonucleotides covering the MTScs sequence and the BamHI and BsaI sites at the ends: 5'-GATCCGGCTTACTTACT-GCGGCCGCCCGGCTCTTGGGAACCAAGAATGCAT CTTGTCTTGTTCTGCAGCCCGGCATGCCAGTTCTG-GAACTTTGGGCCACCC AGGCTCTC-3' (forward) and 5'-TCTAGAGAGCCTGGGTGGCCCAAAGTTCCAG AACTGGCATGCCGCCTGCAAGAACAAGACAAGAT-GCATTCTTGGTTCCCA AGAGCCGGGCGGCCGCAG-TAAGTAAAGCCG-3' (reverse), as denoted by SEQ ID NO. 13 and SEQ ID NO. 14, respectively. The oligonucleotides were ligated to the vector fragment thus obtaining the plasmid encoding the His-TAT-MTScs-FRA fusion protein. In some of the assays described below the His-TAT-MTScs-FRA fusion protein construct used was obtained from Genscript (Lot #342511S03/P10011312; 2.5 mg/ml stock in 50 mM Tris-HCl, 300 mM NaCl, 10% Glycerol, pH 8.0).

All plasmids were confirmed by restriction enzymes and sequencing analyses.

TABLE 1

Nucleic acid and Amino acid sequences

| SEQ ID NO. | Sequence | Name |
|---|---|---|
| 1 | aggaagaagcggagacagcgacgaaga | nt seq. encoding TAT fragment |
| 2 | TGGACTCTCGGGCGCCGCgcagtagccggcctcctggcgtcacccagc ccggcccaggcccagaccctcacccgggtcccgcggccggcagagttggccccactc tgcggccgccgtggcctgcgcaccgacatcgatgcgacctgcacgccccgccgcgca agttcgaaccaacgtggcctcaaccagatttggaatgtcaaaaagcagagtgtctatttgat gaatttgaggaaa | nt seq. of MTSfra |
| 3 | GCTTTACTTACTGCGGCCGCCCGGCTCTTGGGAACCA AGAATGCATCTTGTCTTGTTCTTGCAGCCCGGCATGCC AGT | nt seq. of MTScs |
| 4 | ggagcactagtgattcgcggtatcaggaatttcaacctagagaaccgagcggaacggga aatcagcaagatgaagccctctgtcgctcccagacaccccttct | nt seq. of MTSorf |
| 5 | cagagctggagtcgtgtgtactgctccttggccaagagaggccatttcaatcgaatatctc atggcctacagggactttctgcagtgcctctgagaacttacgca | nt seq. of MTSlad |
| 6 | tctggaactttgggccacccaggctctctagatgagaccacctatgaaagactagcagag gaaacgctggactctttagcagagtttttttgaagaccttgcagacaagccatacacgtttga ggactatgatgtctcctttgggagtggtgtcttaactgtcaaactgggtggagatctaggaa cctatgtgatcaacaagcagacgccaaacaagcaaatctggctatcttctccatccagtgg acctaagcgttatgactggactgggaaaaactgggtgtactcccacgacggcgtgtccct ccatgagctgctggccgcagagctcactaaagccttaaaaaccaaactggacttgtcttC CTTGGCCTATTCCGGAAAAGATGCTTGA | nt seq. of Mature Frataxin (FRA) |
| 7 | CGCGGATCCGTGGACTCTCGGGCGCCG | forward primer for precursor frataxin cloning |
| 8 | ACGCTCGAGTCAAGCATCTTTTCCGGAATAGGC | reverse primer for precursor frataxin cloning |

TABLE 1-continued

Nucleic acid and Amino acid sequences

| SEQ ID NO. | Sequence | Name |
|---|---|---|
| 9 | CGCGGATCCACAGAGCTGGAGTCGTGTGTA | forward primer for MTS lad cloning |
| 10 | CATAGGTGGTCTCATCTAGAGAGCCTGGGTGGCCCAA AGTTCCAGATGCGTAAGTTCTCAGAGGCA | reverse primer for MTS lad cloning |
| 11 | CGCGGATCCGGGAGCACTAGTGATTCGC | forward primer for MTS orf cloning |
| 12 | CATAGGTGGTCTCATCTAGAGAGCCTGGGTGGCCCAA AGTTCCAGAAGAGGGGTGTCTGGGAGCGA | reverse primer for MTS orf cloning |
| 13 | GATCCGGCTTTACTTACTGCGGCCGCCCGGCTCTTGGG AACCAAGAATGCATCTTGTCTTGTTCTTGCAGCCCGGC ATGCCAGTTCTGGAACTTTGGGCCACCCAGGCTCTC | forward oligo for MTS cs cloning |
| 14 | TCTAGAGAGCCTGGGTGGCCCAAAGTTCCAGAACTGG CATGCCGGGCTGCAAGAACAAGACAAGATGCATTCTT GGTTCCCAAGAGCCGGGCGGCCGCAGTAAGTAAAGCC G | reverse primer for MTS cs cloning |
| 15 | CTGAAGGGCCGTGACCTTCTCACTCTAAGAAACTTTA CCGGAGAAGAAATTAAATATATGCTATGGCTATCAGC AGATCTGAAATTTAGGATAAAACAGAAAGGAGAGTA TTTGCCTTTATTGCAAGGGAAGTCCTTAGGCATGATTT TTGAGAAAAGAAGTACTCGAACAAGATTGTCTACAGA AACAGGCTTTGCACTTCTGGGAGGACATCCTTGTTTTC TTACCACACAAGATATTCATTTGGGTGTGAATGAAAG TCTCACGGACACGGCCCGTGTATTGTCTAGCATGGCA GATGCAGTATTGGCTGAGTGTATAAACAATCAGATT TGGACACCCTGGCTAAAGAAGCATCCATCCCAATTAT CAATGGGCTGTCAGATTTGTACCATCCTATCCAGATCC TGGCTGATTACCTCACGCTCCAGGAACACTATAGCTCT CTGAAAGGTCTTACCCTCAGCTGGATCGGGGATGGGA ACAATATCCTGCACTCCATCATGATGAGCGCAGCGAA ATTCGGAATGCACCTTCAGGCAGCTACTCCAAAGGGT TATGAGCCGGATGCTAGTGTAACCAAGTTGGCAGAGC AGTATGCCAAAGAGAATGGTACCAAGCTGTTGCTGAC AAATGATCCATTGGAAGCAGCGCATGGAGGCAATGTA TTAATTACAGACACTTGGATAAGCATGGGACAAGAAG AGGAGAAGAAAAAGCGGCTCCAGGCTTTCCAAGGTTA CCAGGTTACAATGAAGACTGCTAAAGTTGCTGCCTCT GACTGGACATTTTTACACTGCTTGCCCAGAAAGCCAG AAGAAGTGGATGATGAAGTCTTTTATTCTCCTCGATCA CTAGTGTTCCCAGAGGCAGAAAACAGAAAGTGGACA ATCATGGCTGTCATGGTGTCCCTGCTGACAGATTACTC ACCTCAGCTCCAGAAGCCTAAATTTTGA | nt seq. of Mature OTC |
| 16 | ATGTACCGCTACCTGGCCAAAGCGCTGCTGCCGTCCC GGGCCGGGCCCGCTGCCCTGGGCTCCGCGGCCAACCA CTCGGCCGCGTTGCTGGGCCGGGGCCGCGGACAGCCC GCCGCGCCTCGCAGCCGGGGCTCGCATTGGCCGCCC GGCGCCACTAC | nt seq. of MTS of human mitochon. GLUD2 |
| 17 | MGSSHHHHHHSSGLVPRGSHMRKKRRQRRRGSDPALLT AAARLLGTKNASCLVLAARHASSGTLGHPGSLDETTYE RLAEETLDSLAEFFEDLADKPYTFEDYDVSFGSGVLTVK LGGDLGTYVINKQTPNKQIWLSSPSSGPKRYDWTGKNW VYSHDGVSLHELLAAELTKALKTKLDLSSLAYSGKDA | aa seq. of His TAT MTS(cs) 81-210 FRA |
| 18 | MGSSHHHHHHSSGLVPRGSHMRKKRRQRRRGSDPWTL GRRAVAGLLASPSPAQAQTLTRVPRPAELAPLCGRRGLR TDIDATCTPRRASSNQRGLNQIWNVKKQSVYLMNLRKS GTLGHPGSLDETTYERLAEETLDSLAEFFEDLADKPYTFE DYDVSFGSGVLTVKLGGDLGTYVINKQTPNKQIWLSSPS | aa seq. of HTFrataxin [His TAT MTS(fra) |

TABLE 1-continued

Nucleic acid and Amino acid sequences

| SEQ ID NO. | Sequence | Name |
|---|---|---|
| | SGPKRYDWTGKNWVYSHDGVSLHELLAAELTKALKTK<br>LDLSSLAYSGKDA | 81-210<br>FRA] |
| 19 | MGSSHHHHHHSSGLVPRGSHMRKKRRQRRRGSDPQSW<br>SRVYCSLAKRGHFNRISHGLQGLSAVPLRTYASGTLGHP<br>GSLDETTYERLAEETLDSLAEFFEDLADKPYTFEDYDVS<br>FGSGVLTVKLGGDLGTYVINKQTPNKQIWLSSPSSGPKR<br>YDWTGKNWVYSHDGVSLHELLAAELTKALKTKLDLSS<br>LAYSGKDA | aa seq. of<br>His TAT<br>MTS(lad)<br>81-210<br>FRA |
| 20 | MGSSHHHHHHSSGLVPRGSHMRKKRRQRRRGSDPGAL<br>VIRGIRNFNLENRAEREISKMKPSVAPRHPSSGTLGHPGS<br>LDETTYERLAEETLDSLAEFFEDLADKPYTFEDYDVSFG<br>SGVLTVKLGGDLGTYVINKQTPNKQIWLSSPSSGPKRYD<br>WTGKNWVYSHDGVSLHELLAAELTKALKTKLDLSSLA<br>YSGKDA | aa seq. of<br>His TAT<br>MTS(orf)<br>81-210<br>FRA |
| 21 | YGRKKRRQRRR | aa seq. of<br>TAT |
| 22 | WTLGRRAVAGLLASPSPAQAQTLTRVPRPAELAPLCGR<br>RGLRTDIDATCTPRRASSNQRGLNQIWNVKKQSVYLMN<br>LRK | aa seq. of<br>MTS (fra) |
| 23 | ALLTAAARLLGTKNASCLVLAARHAS | aa seq. of<br>MTS (cs) |
| 24 | QSWSRVYCSLAKRGHFNRISHGLQGLSAVPLRTYA | aa seq. of<br>MTS (lad) |
| 25 | GALVIRGIRNFNLENRAEREISKMKPSVAPRHPS | aa seq. of<br>MTS (orf) |
| 26 | SGTLGHPGSLDETTYERLAEETLDSLAEFFEDLADKPYTF<br>EDYDVSFGSGVLTVKLGGDLGTYVINKQTPNKQIWLSSP<br>SSGPKRYDWTGKNWVYSHDGVSLHELLAAELTKALKT<br>KLDLSSLAYSGKDA | aa seq. of<br>Mature<br>frataxin |
| 27 | RKKRRQRRR | aa seq. of<br>TAT<br>fragment |
| 28 | MRKKRRQRRRGSDPALLTAAARLLGTKNASCLVLAAR<br>HASSGTLGHPGSLDETTYERLAEETLDSLAEFFEDLADK<br>PYTFEDYDVSFGSGVLTVKLGGDLGTYVINKQTPNKQI<br>WLSSPSSGPKRYDWTGKNWVYSHDGVSLHELLAAELT<br>KALKTKLDLSSLAYSGKDA | aa seq. of<br>TAT<br>MTS(cs)<br>81-210<br>FRA |
| 29 | MRKKRRQRRRGSDPWTLGRRAVAGLLASPSPAQAQTLT<br>RVPRPAELAPLCGRRGLRTDIDATCTPRRASSNQRGLNQI<br>WNVKKQSVYLMNLRKSGTLGHPGSLDETTYERLAEETL<br>DSLAEFFEDLADKPYTFEDYDVSFGSGVLTVKLGGDLGT<br>YVINKQTPNKQIWLSSPSSGPKRYDWTGKNWVYSHDGV<br>SLHELLAAELTKALKTKLDLSSLAYSGKDA | aa seq. of<br>TAT<br>MTS(fra)<br>81-210<br>FRA |
| 30 | MRKKRRQRRRGSDPQSWSRVYCSLAKRGHFNRISHGLQ<br>GLSAVPLRTYASGTLGHPGSLDETTYERLAEETLDSLAE<br>FFEDLADKPYTFEDYDVSFGSGVLTVKLGGDLGTYVINK<br>QTPNKQIWLSSPSSGPKRYDWTGKNWVYSHDGVSLHEL<br>LAAELTKALKTKLDLSSLAYSGKDA | aa seq. of<br>TAT<br>MTS(lad)<br>81-210<br>FRA |
| 31 | MRKKRRQRRRGSDPGALVIRGIRNFNLENRAEREISKMK<br>PSVAPRHPSSGTLGHPGSLDETTYERLAEETLDSLAEFFE<br>DLADKPYTFEDYDVSFGSGVLTVKLGGDLGTYVINKQT<br>PNKQIWLSSPSSGPKRYDWTGKNWVYSHDGVSLHELLA<br>AELTKALKTKLDLSSLAYSGKDA | aa seq. of<br>TAT<br>MTS(orf)<br>81-210<br>FRA |
| 32 | GSDP | aa seq. of<br>linker |
| 33 | MRKKRRQRRRALLTAAARLLGTKNASCLVLAARHASS<br>GTLGHPGSLDETTYERLAEETLDSLAEFFEDLADKPYFE<br>DYDVSFGSGVLTVKLGGDLGTYVINKQTPNKQIWLSSPS | aa seq. of<br>TAT<br>Mts(cs) |

TABLE 1-continued

Nucleic acid and Amino acid sequences

| SEQ ID NO. | Sequence | Name |
|---|---|---|
|  | SGPKRYDWTGKNWVYSHDGVSLHELLAAELTKALKTK LDLSSLAYSGKDA | 81-210 FRA Δ linker |
| 34 | MRKKRRQRRRWTLGRRAVAGLLASPSPAQAQTLTRVPR PAELAPLCGRRGLRTDIDATCTPRRASSNQRGLNQIWNV KKQSVYLMNLRKSGTLGHPGSLDETTYERLAEETLDSL AEFFEDLADKPYTFEDYDVSFGSGVLTVKLGGDLGTYVI NKQTPNKQIWLSSPSSGPKRYDWTGKNWVYSHDGVSL HELLAAELTKALKTKLDLSSLAYSGKDA | aa seq. of TAT MTS(fra) 81-210 FRA Δ linker |
| 35 | MRKKRRQRRRQSWSRVYCSLAKRGHFNRISHGLQGLSA VPLRTYASGTLGHPGSLDETTYERLAEETLDSLAEFFEDL ADKPYTFEDYDVSFGSGVLTVKLGGDLGTYVINKQTPN KQIWLSSPSSGPKRYDWTGKNWVYSHDGVSLHELLAAE LTKALKTKLDLSSLAYSGKDA | aa seq. of TAT MTS(lad) 81-210 FRA Δ linker |
| 36 | MRKKRRQRRRGALVIRGIRNFNLENRAEREISKMKPSVA PRHPSSGTLGHPGSLDETTYERLAEETLDSLAEFFEDLAD KPYTFEDYDVSFGSGVLTVKLGGDLGTYVINKQTPNKQI WLSSPSSGPKRYDWTGKNWVYSHDGVSLHELLAAELT KALKTKLDLSSLAYSGKDA | aa seq. of TAT MTS(orf) 81-210 FRA Δ linker |

Table 1 above summarizes the nucleic acid sequences (nt) of the primers used as described above (i.e. the primers denoted by SEQ ID NO. 7-SEQ ID NO. 14), the amino acid sequence (aa) of the TAT domain (denoted by SEQ ID NO. 21), the amino acid sequence of a fragment of the TAT domain used in the present disclosure (denoted by SEQ ID NO. 27) and the nucleic acid sequence encoding therefor (denoted by SEQ ID NO. 1), the amino acid sequences of the various MTSs, namely MTS fra, MTS cs, MTS orf and MTS lad (denoted by SEQ ID NO. 22, SEQ ID NO. 23, SEQ ID NO. 25 and SEQ ID NO. 24, respectively) and the nucleic acid sequences encoding therefor (denoted by SEQ ID NO. 2, SEQ ID NO. 3, SEQ ID NO. 4 and SEQ ID NO. 5, respectively), the amino acid sequence of mature frataxin (denoted by SEQ ID NO. 26) and the nucleic acid sequence encoding therefor (denoted by SEQ ID NO. 6), as well as the nucleic acid sequences encoding the OTC protein and the MTS of human mitochondrial GLUD2 (denoted by SEQ ID NO. 15 and SEQ ID NO. 16, respectively). A four-amino acid long linker, having the amino acid sequence of GSDP is also listed in Table 1 above and is denoted by SEQ ID NO. 32.

In addition Table 1 above indicates the amino acid sequences of the various His TAT MTS 81-210 FRA constructs, which comprise the mature frataxin, namely, His TAT MTS(cs) 81-210 FRA, His TAT MTS(fra) 81-210 FRA (also denoted herein as "HTFrataxin"), His TAT MTS(lad) 81-210 FRA and His TAT MTS(orf) 81-210 FRA (denoted by SEQ ID NO. 17, SEQ ID NO. 18, SEQ ID NO. 19 and SEQ ID NO. 20, respectively). The various His TAT MTS 81-210 FRA constructs denoted by SEQ ID NO. 17, SEQ ID NO. 18, SEQ ID NO. 19 and SEQ ID NO. 20 all comprise a short peptide linker denoted by SEQ ID NO. 32, which joins the TAT and MTS domains.

Table 1 above further indicates the amino acid sequences of the various fusion constructs constructed without a His tag at their N-termini and with a short peptide linker denoted by SEQ ID NO. 32 (which joins the TAT and MTS domains). These constructs comprise TAT, a linker, MTS and mature frataxin (81-210 FRA), namely TAT MTS(cs) 81-210 FRA, TAT MTS(fra) 81-210 FRA, TAT MTS(lad) 81-210 FRA and TAT MTS(orf) 81-210 FRA, denoted by SEQ ID NO. 28, SEQ ID NO. 29, SEQ ID NO. 30 and SEQ ID NO. 31, respectively.

In addition Table 1 above indicates the amino acid sequences of the various fusion constructs constructed without a His tag and without a linker. These fusion constructs comprise TAT, MTS and mature frataxin (81-210 FRA), namely TAT MTS(cs) 81-210 FRA Δ linker, TAT MTS(fra) 81-210 FRA Δ linker, TAT MTS(lad) 81-210 FRA Δ linker and TAT MTS(orf) 81-210 FRA Δ linker, denoted by SEQ ID NO. 33, SEQ ID NO. 34, SEQ ID NO. 35 and SEQ ID NO. 36, respectively.

Proteins Expression and Purification

*E. coli* BL21-CodonPlus (λDE3) or HMS competent cells transformed with plasmids encoding the fusion proteins were incubated at 37° C. in a saline lactose broth (SLB medium) containing kanamycine (50 g/ml), tetracycline (12.5 µg/ml) and chloramphenicol (34 µg/ml). At an $OD_{600}$ of 0.2-0.3, 0.1% glycerol and 0.1 mM potassium glutamate were added to the culture which was then heat-shocked for 20-30 min at 42° C., after which the bacteria were grown at 37° C. until an $OD_{600}$ of 0.8. Protein expression was induced by adding isopropyl-beta-D-thiogalactopyranoside (IPTG, for final concentrations see Table 2 below). After 18 hrs of incubation at 22° C., the cells were harvested by centrifugation (500 g for 15 min at 4° C.).

For the purification procedure, bacteria pellets from 0.5 L culture of expressed cells were sonicated in binding buffer (PBS, pH 7.4, 0.4 M NaCl, 10% Glycerol, 1 mM phenylmethylsulphonylfluoride (PMSF) and 30 mM imidazole (Sigma-Aldrich, St. Louis, Mo., USA)). The suspensions were clarified by centrifugation (35,000 g for 30 min at 4° C.), and the supernatants containing the fusion proteins were purified under native conditions, using binding buffer pre-equilibrated HiTrap Chelating HP columns (Amersham-Pharmacia Biotech, Uppsala, Sweden). Columns were washed by stepwise addition of increasing imidazole concentrations. Finally, the target proteins were eluted with elution buffer (PBS, pH 7.4, 0.4 M NaCl, 10% Glycerol, 250 mM imidazole). All purification procedures were carried out using the FPLC system ÄKTA (Amersham-Pharmacia Biotech). Imidazole, NaCl and glycerol were removed by transferring the purified proteins to PBS using PD-10 desalting columns (GE Healthcare, Piscataway, N.J., USA). Aliquots of the proteins were kept frozen at −80° C. until use.

TABLE 2

Expression conditions of TAT-MTS-FRA fusion proteins

| Protein | Bacterial Host | Heat Shock | Temp. for induction (° C.) | IPTG (mM) |
|---|---|---|---|---|
| TAT-MTSfra-FRA | codonPlus | yes | 22 over night | 0.5 |
| TAT-MTScs-FRA | codonPlus | yes | 22 over night | 0.5 |
| TAT-MTSorf-FRA | HMS | yes | 22 over night | 1.0 |
| TAT-MTSlad-FRA | HMS | yes | 22 over night | 1.0 |

Characterization of the Fusion Proteins

Determination of Protein Concentration Protein concentration was measured according to the Bradford method, using the Bradford reagent and the standard curve of BSA. Protein concentration was determined at a wavelength of 595 nm.

Separation of Proteins by Electrophoresis Samples from the various protein fractions (5-20 µg protein/lane) were loaded on 12% or 15% (w/v) SDS-PAGE gels. The separation of proteins was done using Sturdier Slab Gel Electrophoresis apparatus according to the manufacturer's instructions (Hoefer Sci Instruments, San Francisco, Calif., USA).

Western Blot Analysis Proteins (5-20 µg protein/lane) were resolved on 12%-15% SDS-PAGE gels and transferred onto an Immobilon-P Transfer membrane (Millipore, Bradford, Pa., USA). Western blot analysis was performed using either anti-frataxin (Abcam), or anti-His (Amersham-Pharmacia Biotech) antibodies at dilutions of 1:600 and 1:30,000, respectively, to identify the relevant proteins. Primary antibody binding was detected by blotting with a suitable secondary antibody conjugated to horseradish peroxidase (HRP) (1:10,000). Band visualization was done using an enhanced chemiluminescence kit (EZ-ECL, Biological Industries, Beit-Haemek, Israel).

Internalization of TAT-MTS-FRA into the Mitochondria of Patients' Fibroblasts

FA patient fibroblasts (Coriell repository, #GM03816, termed F816) were thawed and passed at least 2-3 times prior to assay performance and then incubated in the presence of the fusion protein construct TAT-MTS(cs)-FRA (20 µg/ml) comprising frataxin and citrate synthase as the mitochondrial targeting sequence (MTS) for 2, 6 and 48 hours, with fresh addition of TAT-MTS(CS)-FXN (at 20 µg/ml) after 24 hours. Vehicle was added as negative control. Cells were fractionated to cytosolic (C) and mitochondrial (M) fractions using Mitochondria isolation kit (Millipore, MIT1000). All fractions were analyzed in Western blot analysis using a monoclonal anti-frataxin antibody directed against the C-terminal region of frataxin (Abnova, cat. no. H00002395-M02, lot 08078-3F3) diluted 1:500 in blocking solution. Detection was performed using 1 ml at 1 mg/ml of a goat anti mouse IgG-h+1 alkaline phosphatase conjugated antibody (BETHYL, Cat#A90-116AP-16) diluted to 1:20,000 in blocking solution. Signal was developed using the ready-to-use buffered alkaline phosphatase substrate for use in immunoblotting BCIPÒ/NBT-Blue (Sigma, B3804).

Aconitase Activity Assay

Aconitase activity assay was performed using a commercial kit (Abcam, ab109712, microplate assay kit) according to the manufacturer's instructions. The conversion of isocitrate to cis-aconitate is measured as an increase in absorbance at OD 240 nm at specific time points and calculated as activity rate (mOD/min).

BSO Experiments for Inducing Oxidative Stress

Normal or patients' lymphocytes ($4\times10^3$ cells/100 µl) were seeded in Dulbecco's Modified Eagle Medium (DMEM, Bet Ha'emek, Israel) medium without phenol red and sodium pyruvate (experimental medium) and after 3-4 hr the tested TAT-MTS-FRA fusion protein (at a final concentration of 0.1 µg/µl) was added to the cells for 5 or 24 hr. Following the incubation time with the fusion protein, L-Buthionine-sulfoximine (BSO, Sigma B2640) at different concentrations was added for an additional period of 48 hr. At the end of the incubation time, cell cultures were subjected to cell viability or cell proliferation assays, using the CellTiter-Blue™ kit (Promega, Madison, Wis.) according to manufacturer's instructions, as detailed below. In experiments conducted in fibroblasts, cells ($3\times10^3$ cells/100 µl) were seeded in the growth medium as specified above and left for 24 hr to allow the cells to adhere. After 24 hr, the medium was changed to the experimental medium and the experiment was continued as described for lymphocytes above.

Cell Proliferation Assay $10^4$/100 µl/well cells growing in suspension or $5\times10^3$/100 µl/well adherent cells were seeded and treated with increasing concentrations of the fusion protein for 48-72 h, after which cellTiter-Blue® reagent (Promega, Madison, Wis., USA) was added according to the manufacturer's instructions to determine cell survival. All treatments were performed in triplicates.

In Vitro Caspase 3 Activity Assay $10^4$/100 µl/well cells growing in suspension or $5\times10^3$/100 µl/well adherent cells were treated with the fusion protein (0.15 µg/µl, final concentration). Caspase3 activity within the cells was assessed by Apo-ONE® Homogeneous Caspase3/7 Assay Kit (Promega). Caspase 3 activity assays were carried in parallel to cell viability assays.

Preparation of his-TAT-MTS-OTC Constructs

Fusion protein constructs comprising ornithine transcarbamoylase (OTC) conjugated to a His-TAT-MTS fragment, namely, His-TAT-MTS(otc)-OTC, His-TAT-MTS(lad)-OTC, His-TAT-MTS(cs)-OTC and His-TAT-MTS(orf)-OTC were obtained from GenScript. These fusion protein constructs were prepared by expressing vectors harboring these constructs in E. coli cells and purified from inclusion bodies to about 80% purity using Ni column chromatography.

TABLE 3

Nucleic acid and amino acid sequences of TAT-MTS-OTC constructs

| SEQ ID NO. | Sequence | Name |
|---|---|---|
| 37 | CTGTTTAACCTGCGCATTCTGCTGAACAATGCGGCCTTCCG TAACGGCCATAATTTTATGGTCCGCAACTTCCGTTGCGGTCA GCCGCTGCAAAATAAAGTGCAG | nt seq.of MIS of OTC |

TABLE 3-continued

Nucleic acid and amino acid sequences of TAT-MTS-OTC constructs

| SEQ ID NO. | Sequence | Name |
|---|---|---|
| 38 | LFNLRILLNNAAFRNGHNFMVRNFRCGQPLQNKVQ | aa seq. of MTS of OTC |
| 39 | LKGRDLLTLRNFTGEEIKYMLWLSADLKFRIKQKGEYLPLLQ G KSLGMIFEKRSTRTRLSTETGFALLGGHPCFLTTQDIHLG VNESLTDTARVLSSMADAVLARVYKQSDLDTLAKEASIPIIN GLSDLYHPIQILADYLTLQEHYSSLKGLTLSWIGDGNNILHS IMMSAAKFGMHLQAATPKGYEPDASVTKLAEQYAKENGTKLL LTNDPLEAAHGGNVLITDTWISMGQEEEKKKRLQAFQGYQVT MKTAKVAASDWTFLHCLPRKPEEVDDEVFYSPRSLVFPEAEN RKWTIMAVMVSLLTDYSPQLQKPKF | aa seq. of mature OTC |
| 40 | CATATGGCT CATCGCATCA TCATCATCAT CACTCATCAG GTCTGGTTCC GCGTGGCTCG CACATGTATG GTCGCAAAAA ACGTCGTCAA CGTCGCCGTC TGTTTAACCT GCGCATTCTG CTGAACAATG CGGCCTTCCG TAACGGCCAT AATTTTATGG TCCGCAACTT CCGTTGCGGT CAGCCGCTGC AAAATAAAGT GCAGCTGAAA GGCCGCGATC TGCTGACCCT GCGTAACTTC ACGGGTGAAG AAATCAAATA CATGCTGTGG CTGAGCGCAG ACCTGAAATT CCGCATCAAA CAAAAAGGCG AATACCTGCC GCTGCTGCAG GGCAAATCTC TGGGTATGAT TTTTGAAAAA CGTAGTACCC GCACGCGTCT GTCCACCGAA ACGGGCTTTG CCCTGCTGGG CGGTCATCCG TGTTTCCTGA CCACGCAAGA TATCCACCTG GGTGTGAACG AAAGTCTGAC CGATACGGCA CGCGTTCTGA GCTCTATGGC AGACGCTGTG CTGGCTCGTG TTTATAAACA GTCCGATCTG GACACCCTGG CGAAAGAAGC CTCAATTCCG ATTATCAATG GCCTGTCGGA TCTGTACCAT CCGATTCAAA TCCTGGCGGA CTATCTGACC CTGCAGGAAC ACTACAGTTC CCTGAAAGGT CTGACCCTGA GTTGGATCGG CGATGGTAAC AATATTCTGC ATAGCATCAT GATGTCTGCA GCTAAATTTG GCATGCACCT GCAAGCGGCC ACCCCGAAAG GTTATGAACC GGATGCCAGC GTTACGAAAC TGGCAGAACA GTACGCTAAA GAAAACGGTA CCAAACTGCT GCTGACGAAT GATCCGCTGG AAGCAGCTCA TGGCGGTAAC GTCCTGATTA CCGACACGTG GATCTCTATG GGCCAGGAAG AAGAAAAGAA AAAACGTCTG CAGGCGTTTC AAGGTTATCA GGTTACCATG AAAACGGCCA AAGTCGCGGC CAGCGATTGG ACCTTCCTGC ACTGCCTGCC GCGTAAACCG GAAGAAGTCG ATGACGAAGT GTTTTACTCA CCGCGCTCGC TGGTGTTCCC GGAAGCAGAA AATCGTAAAT GGACCATCAT GGCTGTTATG GTGTCCCTGC TGACCGACTA TTCCCCGCAA CTGCAAAAAC CGAAATTCTA ATGAAAGCTT | nt seq. of His-TAT-MTS(otc)-OTC Δ linker |
| 41 | CATATGGCT CATCTCATCA TCATCATCAT CATTCGTCAG GTCTGGTCCC GCGTGGCTCT CACATGCGTA AAAACGTCG TCAGCGTCGT CGTGGCAGTG ATCCGGCACT GCTGACCGCA GCAGCACGTC TGCTGGGTAC GAAAAACGCT AGCTGCCTGG TGCTGGCTGC GCGTCATGCG TCTGAATTTC TGAAAGGCCG TGATCTGCTG ACCCTGCGCA ACTTCACGGG TGAAGAAATC AAATACATGC TGTGGCTGAG TGCCGACCTG AAATTTCGTA TCAAACAAAA AGGCGAATAC CTGCCGCTGC TGCAGGGCAA ATCCCTGGGT ATGATTTTCG AAAAACGCAG TACCCGTACG CGCCTGTCCA CCGAAACGGG CTTTGCACTG CTGGGCGGTC ATCCGTGTTT CCTGACCACG CAAGATATCC ACCTGGGTGT GAACGAATCA CTGACCGATA CGGCTCGTGT TCTGAGCTCT ATGGCAGACG CAGTGCTGGC ACGTGTTTAT AAACAGTCGG ATCTGGACAC CCTGGCTAAA GAAGCGTCAA TTCCGATTAT CAATGGCCTG TCGGATCTGT ACCATCCGAT TCAAATCCTG GCGGACTATC TGACCCTGCA GGAACACTAC AGTTCCCTGA AAGGTCTGAC CCTGAGCTGG | nt seq. of His-TAT-MTS(cs)-OTC |

TABLE 3-continued

Nucleic acid and amino acid sequences of TAT-MTS-OTC constructs

| SEQ ID NO. | Sequence | Name |
|---|---|---|
| | ATCGGCGATG GTAACAATAT TCTGCATAGC<br>ATCATGATGT CTGCCGCAAA ATTTGGCATG<br>CACCTGCAAG CTGCGACCCC GAAAGGTTAT<br>GAACCGGACG CCAGCGTCAC GAAACTGGCC<br>GAACAGTACG CAAAAGAAAA CGGTACCAAA<br>CTGCTGCTGA CGAATGATCC GCTGGAAGCC<br>GCACATGGCG GTAACGTTCT GATTACCGAC<br>ACGTGGATCA GCATGGGCCA GGAAGAAGAA<br>AAGAAAAAAC GTCTGCAGGC CTTTCAAGGT<br>TATCAGGTTA CCATGAAAAC GGCAAAAGTC<br>GCTGCGTCTG ATTGGACCTT CCTGCACTGC<br>CTGCCGCGCA AACCGGAAGA AGTCGATGAC<br>GAAGTGTTTT ACTCACCGCG TTCGCTGGTT<br>TTCCCGGAAG CGGAAAATCG CAAATGGACC<br>ATTATGGCTG TGATGGTCTC TCTGCTGACG<br>GACTACTCGC CGCAACTGCA AAAACCGAAA<br>TTCTAATGAA AGCTT | |
| 42 | CATATGGGTT CATCACATCA TCATCATCAT<br>CATTCATCAG GTCTGGTCCC GCGTGGTTCA<br>CACATGCGTA AAAAACGTCG TCAGCGTCGT<br>CGTGGCAGTG ATCCGGGTGC GCTGGTCATT<br>CGTGGCATCC GCAACTTTAA TCTGGAAAAC<br>CGTGCGGAAC GCGAAATTAG TAAAATGAAA<br>CCGTCCGTGG CACCGCGTCA TCCGTCTGAA<br>TTTCTGAAAG CCGTGATCT GCTGACCCTG<br>CGCAACTTCA CGGGTGAAGA AATCAAATAC<br>ATGCTGTGGC TGAGTGCAGA CCTGAAATTC<br>CGTATCAAAC AAAAGGGTGA ATACCTGCCG<br>CTGCTGCAGG GCAAATCCCT GGGTATGATT<br>TTCGAAAAAC GCTCAACCCG TACGCGCCTG<br>TCGACCGAAA CGGGCTTTGC CCTGCTGGGC<br>GGTCATCCGT GCTTCCTGAC CACGCAAGAT<br>ATCCACCTGG GTGTGAACGA ATCACTGACC<br>GATACGGCAC GTGTTCTGAG CTCTATGGCA<br>GACGCAGTGC TGGCTCGTGT TTATAAACAG<br>TCGGATCTGG ACACCCTGGC AAAAGAAGCT<br>AGCATTCCGA TTATCAATGG CCTGTCTGAT<br>CTGTACCATC CGATTCAAAT CCTGGCGGAC<br>TATCTGACCC TGCAGGAACA CTACAGTTCC<br>CTGAAAGGTC TGACCCTGAG CTGGATCGGC<br>GATGGTAACA ATATTCTGCA TAGCATCATG<br>ATGTCTGCGG CCAAATTCGG CATGCACCTG<br>CAAGCAGCTA CCCCGAAAGG TTATGAACCG<br>GACGCCTCCG TTACGAAACT GGCGGAACAG<br>TACGCCAAAG AAAACGGCAC CAAACTGCTG<br>CTGACGAATG ATCCGCTGGA AGCGGCCCAT<br>GGCGGTAACG TCCTGATTAC CGACACGTGG<br>ATCAGCATGG GCCAGGAAGA AGAAAAAGAAA<br>AAACGTCTGC AGGCATTTCA AGGTTATCAG<br>GTTACCATGA AAACGGCTAA AGTCGCAGCT<br>TCTGATTGGA CCTTCCTGCA CTGTCTGCCG<br>CGCAAACCGG AAGAAGTCGA TGACGAAGTG<br>TTTTACTCAC CGCGTTCGCT GGTGTTCCCG<br>GAAGCGGAAA ATCGCAAATG GACCATTATG<br>GCTGTGATGG TGTCGCTGCT GACGGACTAC<br>TCGCCGCAAC TGCAAAAACC GAAATTCTAA TGAAAGCTT | nt seq. of<br>His-TAT-<br>MTS(orf)-<br>OTC |
| 43 | CATATGGGTA GTTCACATCA TCATCATCAT<br>CACTCGTCGG GTCTGGTGCC GCGTGGCTCA<br>CACATGCGTA AAAAACGTCG TCAGCGTCGT<br>CGTGGCTCAG ATCCGCAATC ATGGTCGCGC<br>GTCTATTGCT CGCTGGCGAA ACGTGGTCAT<br>TTTAACCGCA TTAGCCACGG CCTGCAGGGT<br>CTGTCTGCAG TGCCGCTGCG TACCTACGCT<br>GAATTTCTGA AAGGCCGTGA TCTGCTGACC<br>CTGCGCAACT TCACGGGTGA AGAAATCAAA<br>TACATGCTGT GGCTGAGCGC AGACCTGAAA<br>TTTCGTATCA AACAAAAAGG CGAATACCTG<br>CCGCTGCTGC AGGGCAAATC TCTGGGTATG<br>ATTTTCGAAA AACGCTCAAC CCGTACGCGC<br>CTGTCGACCG AAACGGGCTT TGCCCTGCTG<br>GGCGGTCATC CGTGTTTCCT GACCACGCAG<br>GATATCCACC TGGGTGTGAA CGAAAGTCTG<br>ACCGATACGG CACGTGTTCT GAGCTCTATG<br>GCAGACGCAG TGCTGGCTCG TGTTTATAAA | nt seq. of<br>His-TAT-<br>MTS(lad)-<br>OTC |

TABLE 3-continued

Nucleic acid and amino acid sequences of TAT-MTS-OTC constructs

| SEQ ID NO. | Sequence | Name |
|---|---|---|
| | CAGTCCGATC TGGACACCCT GGCAAAAGAA GCTAGTATTC CGATTATCAA TGGCCTGTCC GATCTGTACC ATCCGATTCA AATCCTGGCG GACTATCTGA CCCTGCAGGA ACACTACAGT TCCCTGAAAG GTCTGACGCT GAGCTGGATC GGCGATGGTA ACAATATTCT GCATAGTATC ATGATGTCCG CGGCCAAATT CGGCATGCAC CTGCAAGCAG CTACCCCGAA AGGTTATGAA CCGGACGCCT CTGTTACGAA ACTGGCGGAA CAGTACGCCA AAGAAAACGG TACCAAACTG CTGCTGACGA ATGATCCGCT GGAAGCGGCC CATGGCGGTA ACGTCCTGAT TACCGACACG TGGATCAGTA TGGGCCAGGA AGAAGAAAAG AAAAAACGTC TGCAGGCGTT TCAAGGTTAT CAGGTTACCA TGAAAACGGC CAAAGTCGCA GCTAGCGATT GGACCTTCCT GCACTGCCTG CCGCGCAAAC CGGAAGAAGT CGATGACGAA GTGTTTTATA GCCCGCGTTC TCTGGTGTTC CCGGAAGCGG AAAATCGCAA ATGGACCATC ATGGCCGTTA TGGTGTCGCT GCTGACCGAT TACTCCCCGC AACTGCAAAA ACCGAAATTC TAATGAAAGC TT | |
| 44 | MGSSHHHHHH SSGLVPRGSH MYGRKKRRQR RRLFNLRILL NNAAFRNGHN FMVRNFRCGQ PLQNKVQLKG RDLLTLRNFT GEEIKYMLWL SADLKFRIKQ KGEYLPLLQG KSLGMIFEKR STRTRLSTET GFALLGGHPC FLTTQDIHLG VNESLTDTAR VLSSMADAVL ARVYKQSDLD TLAKEASIPI INGLSDLYHP IQILADYLTL QEHYSSLKGL TLSWIGDGNN ILHSIMMSAA KFGMHLQAAT PKGYEPDASV TKLAEQYAKE NGTKLLLTND PLEAAHGGNV LITDTWISMG QEEEKKKRLQ AFQGYQVTMK TAKVAASDWT FLHCLPRKPE EVDDEVFYSP RSLVFPEAEN RKWTIMAVMV SLLTDYSPQL QKPKF | aa seq. of His-TAT-MTS(otc)-OTC Δ linker |
| 45 | MGSSHHHHHH SSGLVPRGSH MRKKRRQRRR GSDPALLTAA ARLLGTKNAS CLVLAARHAS EFLKGRDLLT LRNFTGEEIK YMLWLSADLK FRIKQKGEYL PLLQGKSLGM IFEKRSTRTR LSTETGFALL GGHPCFLTTQ DIHLGVNESL TDTARVLSSM ADAVLARVYK QSDLDTLAKE ASIPIINGLS DLYHPIQILA DYLTLQEHYS SLKGLTLSWI GDGNNILHSI MMSAAKFGMH LQAATPKGYE PDASVTKLAE QYAKENGTKL LLTNDPLEAA HGGNVLITDT WISMGQEEEK KKRLQAFQGY QVTMKTAKVA ASDWTFLHCL PRKPEEVDDE VFYSPRSLVF PEAENRKWTI MAVMVSLLTD YSPQLQKPKF | aa seq. of His-TAT-MTS(cs)-OTC |
| 46 | MGSSHHHHHH SSGLVPRGSH MRKKRRQRRR GSDPGALVIR GIRNFNLENR AEREISKMKP SVAPRHPSEF LKGRDLLTLR NFTGEEIKYM LWLSADLKFR IKQKGEYLPL LQGKSLGMIF EKRSTRTRLS TETGFALLGG HPCFLTTQDI HLGVNESLTD TARVLSSMAD AVLARVYKQS DLDTLAKEAS IPIINGLSDL YHPIQILADY LTLQEHYSSL KGLTLSWIGD GNNILHSIMM SAAKFGMHLQ AATPKGYEPD ASVTKLAEQY AKENGTKLLL TNDPLEAAHG GNVLITDTWI SMGQEEEKKK RLQAFQGYQV TMKTAKVAAS DWTFLHCLPR KPEEVDDEVF YSPRSLVFPE AENRKWTIMA VMVSLLTDYS PQLQKPKF | aa seq. of His-TAT-MTS(orf)-OTC |
| 47 | MGSSHHHHHH SSGLVPRGSH MRKKRRQRRR GSDPQSWSRV YCSLAKRGHF NRISHGLQGL SAVPLRTYAE FLKGRDLLTL RNFTGEEIKY MLWLSADLKF RIKQKGEYLP LLQGKSLGMI FEKRSTRTRL STETGFALLG GHPCFLTTQD IHLGVNESLT DTARVLSSMA DAVLARVYKQ SDLDTLAKEA SIPIINGLSD LYHPIQILAD YLTLQEHYSS LKGLTLSWIG DGNNILHSIM MSAAKFGMHL QAATPKGYEP DASVTKLAEQ YAKENGTKLL LTNDPLEAAH GGNVLITDTW ISMGQEEEKK KRLQAFQGYQ VTMKTAKVAA | aa seq. of His-TAT-MTS(lad)-OTC |

TABLE 3-continued

Nucleic acid and amino acid sequences of TAT-MTS-OTC constructs

| SEQ ID NO. | Sequence | Name |
|---|---|---|
| | SDWTFLHCLP RKPEEVDDEV FYSPRSLVFP<br>EAENRKWTIM AVMVSLLTDY SPQLQKPKF | |
| 48 | RKKRRQRRRL FNLRILLNNA AFRNGHNFMV<br>RNFRCGQPLQ NKVQLKGRDL LTLRNFTGEE<br>IKYMLWLSAD LKFRIKQKGE YLPLLQGKSL<br>GMIFEKRSTR TRLSTETGFA LLGGHPCFLT<br>TQDIHLGVNE SLTDTARVLS SMADAVLARV<br>YKQSDLDTLA KEASIPIING LSDLYHPIQI<br>LADYLTQEH YSSLKGLTLS WIGDGNNILH<br>SIMMSAAKFG MHLQAATPKG YEPDASVTKL<br>AEQYAKENGT KLLLTNDPLE AAHGGNVLIT<br>DTWISMGQEE EKKKRLQAFQ GYQVTMKTAK<br>VAASDWTFLH CLPRKPEEVD DEVFYSPRSL<br>VFPEAENRKW TIMAVMVSLL TDYSPQLQKPKF | aa seq. of<br>TAT-<br>MTS(otc)-<br>OTC<br>Δ linker |
| 49 | MRKKRRQRRR GSDPALLTAA ARLLGTKNAS<br>CLVLAARHAS EFLKGRDLLT LRNFTGEEIK<br>YMLWLSADLK FRIKQKGEYL PLLQGKSLGM<br>IFEKRSTRTR LSTETGFALL GGHPCFLTTQ<br>DIHLGVNESL TDTARVLSSM ADAVLARVYK<br>QSDLDTLAKE ASIPIINGLS DLYHPIQILA<br>DYLTQEHYS SLKGLTLSWI GDGNNILHSI<br>MMSAAKFGMH LQAATPKGYE PDASVTKLAE<br>QYAKENGTKL LLTNDPLEAA HGGNVLITDT<br>WISMGQEEEK KKRLQAFQGY QVTMKTAKVA<br>ASDWTFLHCL PRKPEEVDDE VFYSPRSLVF<br>PEAENRKWTI MAVMVSLLTD YSPQLQKPKF | aa seq. of<br>TAT-<br>MTS(cs)-<br>OTC |
| 50 | MRKKRRQRRR GSDPGALVIR GIRNFNLENR<br>AEREISKMKP<br>SVAPRHPSEF LKGRDLLTLR NFTGEEIKYM<br>LWLSADLKFR IKQKGEYLPL QGKSLGMIF<br>EKRSTRTRLS TETGFALLGG HPCFLTTQDI<br>HLGVNESLTD TARVLSSMAD AVLARVYKQS<br>DLDTLAKEAS IPIINGLSDL YHPIQILADY<br>LTQEHYSSL KGLTLSWIGD GNNILHSIMM<br>SAAKFGMHLQ AATPKGYEPD ASVTKLAEQY<br>AKENGTKLLL TNDPLEAAHG GNVLITDTWI<br>SMGQEEEKKK RLQAFQGYQV TMKTAKVAAS<br>DWTFLHCLPR KPEEVDDEVF YSPRSLVFPE<br>AENRKWTIMA VMVSLLTDYS PQLQKPKF | aa seq. of<br>TAT-<br>MTS(orf)-<br>OTC |
| 51 | MRKKRRQRRR GSDPQSWSRV YCSLAKRGHF<br>NRISHGLQGL<br>SAVPLRTYAE FLKGRDLLTL RNFTGEEIKY<br>MLWLSADLKF RIKQKGEYLP LLQGKSLGMI<br>FEKRSTRTRL STETGFALLG GHPCFLTTQD<br>IHLGVNESLT DTARVLSSMA DAVLARVYKQ<br>SDLDTLAKEA SIPIINGLSD LYHPIQILAD<br>YLTQEHYSS LKGLTLSWIG DGNNILHSIM<br>MSAAKFGMHL QAATPKGYEP DASVTKLAEQ<br>YAKENGTKLL LTNDPLEAAH GGNVLITDTW<br>ISMGQEEEKK KRLQAFQGYQ VTMKTAKVAA<br>SDWTFLHCLP RKPEEVDDEV FYSPRSLVFP<br>EAENRKWTIM AVMVSLLTDY SPQLQKPKF | aa seq. of<br>TAT-<br>MTS(lad)-<br>OTC |
| 52 | MRKKRRQRRR ALLTAA ARLLGTKNAS CLVLAARHAS<br>EFLKGRDLLT LRNFTGEEIK YMLWLSADLK<br>FRIKQKGEYL PLLQGKSLGM IFEKRSTRTR<br>LSTETGFALL GGHPCFLTTQ DIHLGVNESL<br>TDTARVLSSM ADAVLARVYK QSDLDTLAKE<br>ASIPIINGLS DLYHPIQILA DYLTQEHYS<br>SLKGLTLSWI GDGNNILHSI MMSAAKFGMH<br>LQAATPKGYE PDASVTKLAE QYAKENGTKL<br>LLTNDPLEAA HGGNVLITDT WISMGQEEEK<br>KKRLQAFQGY QVTMKTAKVA ASDWTFLHCL<br>PRKPEEVDDE VFYSPRSLVF PEAENRKWTI<br>MAVMVSLLTD YSPQLQKPKF | aa seq. of<br>TAT-<br>MTS(cs)-<br>OTC Δ<br>linker |
| 53 | MRKKRRQRRR GALVIR GIRNFNLENR AEREISKMKP<br>SVAPRHPSEF LKGRDLLTLR NFTGEEIKYM<br>LWLSADLKFR IKQKGEYLPL QGKSLGMIF<br>EKRSTRTRLS TETGFALLGG HPCFLTTQDI<br>HLGVNESLTD TARVLSSMAD AVLARVYKQS<br>DLDTLAKEAS IPIINGLSDL YHPIQILADY | aa seq. of<br>TAT-<br>MTS(orf)-<br>OTC Δ<br>linker |

TABLE 3-continued

Nucleic acid and amino acid sequences of TAT-MTS-OTC constructs

| SEQ ID NO. | Sequence | Name |
|---|---|---|
| | LTLQEHYSSL KGLTLSWIGD GNNILHSIMM<br>SAAKFGMHLQ AATPKGYEPD ASVTKLAEQY<br>AKENGTKLLL TNDPLEAAHG GNVLITDTWI<br>SMGQEEEKKK RLQAFQGYQV TMKTAKVAAS<br>DWTFLHCLPR KPEEVDDEVF YSPRSLVFPE<br>AENRKWTIMA VMVSLLTDYS PQLQKPKF | |
| 54 | MRKKRRQRRR QSWSRV YCSLAKRGHF NRISHGLQGL<br>SAVPLRTYAE FLKGRDLLTL RNFTGEEIKY<br>MLWLSADLKF RIKQKGEYLP LLQGKSLGMI<br>FEKRSTRTRL STETGFALLG GHPCFLTTQD<br>IHLGVNESLT DTARVLSSMA DAVLARVYKQ<br>SDLDTLAKEA SIPIINGLSD LYHPIQILAD<br>YLTLQEHYSS LKGLTLSWIG DGNNILHSIM<br>MSAAKFGMHL QAATPKGYEP DASVTKLAEQ<br>YAKENGTKLL LTNDPLEAAH GGNVLITDTW<br>ISMGQEEEKK KRLQAFQGYQ VTMKTAKVAA<br>SDWTFLHCLP RKPEEVDDEV FYSPRSLVFP<br>EAENRKWTIM AVMVSLLTDY SPQLQKPKF | aa seq. of<br>TAT-<br>MTS(lad)-<br>OTC Δ<br>linker |

Table 3 recites the amino acid sequence of the MTS of the OTC protein and the nucleotide sequence encoding therefor (denoted by SEQ ID NO. 38 and by SEQ ID NO. 37, respectively), the amino acid sequence of mature OTC (denoted by SEQ ID NO. 39), and the nucleotide sequences encoding the fusion protein constructs His-TAT-MTS(otc)-OTC Δ linker, His-TAT-MTS(cs)-OTC, His-TAT-MTS(orf)-OTC and His-TAT-MTS(lad)-OTC (denoted by SEQ ID NO. 40, denoted by SEQ ID NO. 41, SEQ ID NO. 42 and by SEQ ID NO. 43, respectively).

Table 3 also indicates the amino acid sequences of the fusion protein constructs His-TAT-MTS(otc)-OTC Δ linker, His-TAT-MTS(cs)-OTC, His-TAT-MTS(orf)-OTC and His-TAT-MTS(lad)-OTC (denoted by SEQ ID NO. 44, SEQ ID NO. 45, SEQ ID NO. 46 and by SEQ ID NO. 47, respectively).

Also recited are fusion protein constructs comprising the mitochondrial active protein OTC where the fusion protein construct does not include a His tag, namely the constructs TAT-MTS(otc)-OTC Δ linker having the amino acid sequences denoted by SEQ ID NO. 48, TAT-MTS(cs)-OTC (denoted by SEQ ID NO. 49), TAT-MTS(orf)-OTC (denoted by SEQ ID NO. 50) and TAT-MTS(lad)-OTC (denoted by SEQ ID NO. 51).

The fusion protein constructs according to the present disclosure may be prepared in the presence of a linker situated between the TAT and the MTS fragments or in its absence. Thus table 3 also recites the sequences of the fusion protein constructs termed His-TAT-MTS(otc)-OTC Δ linker, TAT-MTS(cs)-OTC Δ linker, TAT-MTS(orf)-OTC Δ linker, TAT-MTS(lad)-OTC Δ linker (having the amino acid sequences denoted by SEQ ID NO. 44, SEQ ID NO. 52, SEQ ID NO. 53 and SEQ ID NO. 54, respectively).

Internalization of his-TAT-MTS-OTC Constructs into the Mitochondria

A culture of $10^7$ HepG2 cells (ATCC, #HB-8065) was seeded in T-75 flasks. The next day, TAT-MTS-OTC fusion protein constructs comprising either OTC, CS or LAD at 12 μg/ml prepared as described above were added to the cells in Eagle's Minimum Essential Medium (EMEM) complete medium, or in EMEM medium supplemented with DMSO (1%) and Trehalose (30 mM) or in EMEM medium supplemented with DMSO (1%), Trehalose (30 mM) and Ornithine (1 mM) for an incubation of 20 min, 1 or 3 hours. Cells were then fractionated to cytosolic and mitochondrial fractions using Mitochondria isolation kit (Millipore, MIT1000) according to the manufacturer's instructions. Fractions were analyzed in Western blot analysis using a monoclonal antibody directed to the C terminal region of OTC (Aviva Systems Biology, cat. no. ARP41767_P050), at 1 mg/ml diluted 1:1000. Detection was performed with the goat anti rabbit IgG (H_L) secondary antibody peroxidase conjugated (Jackson AffiniPure, Code 111-035-003) at 0.8 mg/ml, diluted 1:20,000 in blocking buffer ( ). Signal was developed with chemiluminescence mixture (SC-2048 Santa Cruz) according to the manufacturer's instructions.

In Vitro Production of Citrulline by the Enzymatic Activity of OTC

Purified TAT-MTS-OTC fusion protein constructs comprising the MTS of OTC or CS prepared as described above were tested for their enzymatic activity as described in [40]. Briefly, proteins were diluted in a mitochondria lysis buffer (0.5% Triton, 10 mM HEPES, pH 7.2 and 2 mM dithiothreitol) to a concentration of 20 μg in a volume of 80 μl. Then the volume of each of the reaction mixtures was completed to 600 μl by adding 520 μl reaction mixture (5 mM ornithine, 15 mM carbamoyl phosphate, and 270 mM triethanolamine, pH 7.7). Following vortexing, each reaction mixture was divided into two separate tubes, the first tube was incubated at 37° C. for 30 min and the second tube served as "no-reaction" background and used to subtract endogenous signal of OTC proteins. Reactions were terminated by adding 150 μl of 1:3 sulfuric acid/phosphoric acid (by volume). Citrulline production was then determined by adding 20 μl of 3% 2,3-butanedione monoxime, incubating at 100° C. in the dark for 15 min, and measuring absorbance at 490 nm. Commercially available OTC from *Bacillus subtilis* (Sigma, 5 ng) was used as Positive Control (data not shown).

Enzymatic Activity of OTC in HepG2 Cells in the Presence of Ammonia

HepG2 cells $2.5 \times 10^5$ (ATCC, #HB-8065) per well were seeded in two 6-well plates. The next day, TAT-MTS-OTC fusion protein constructs comprising the MTS of OTC or CS (prepared as described above) were applied to the cells for 72 hours with replenishment after each 24 hours. The final concentration of the fusion proteins was 14 μg/ml, in 3 ml complete medium and the final buffer dilution was 1:85. Proteins storage buffer (1×PBS, 0.5% Sodium Lauroyl Sarcosine at pH 7.4) served as vehicle control and untreated cells as negative control. At 48 hours prior to the termination of the assay, cells were treated with 0.5% serum growth medium in the absence or in the presence of 5 mM Ammonium chloride. Cells viability was monitored for 4 hours with alamarBlue Cell Viability Assay Reagent (Pierce). Fluorescence signal was obtained by excitation at 544 nm and emission at 590 nm.

Example 1

Cloning of Plasmids Encoding TAT-MTS-FRA Fusion Proteins

Expression plasmids encoding the TAT-fusion proteins were cloned and prepared by standard molecular biology tools known in the art. For a general reference see Molecular Cloning: A Laboratory manual (2001) Joseph Sambrook and David William Russell. TAT [9] having the amino acid sequence as denoted by SEQ ID NO. 27 (encoded by the nucleic acid sequence denoted by SEQ ID NO. 1) was fused (N-terminal) to the mature human frataxin protein (having the amino acid sequence as denoted by SEQ ID NO. 26 and encoded by the nucleic acid sequence as denoted by SEQ ID NO. 6).

Various fusion constructs were prepared, which differ in their mitochondrial targeting sequence present at the N terminus of human frataxin (and thus located between the TAT and mature human frataxin described above), being either the native mitochondrial targeting sequence of frataxin (referred to herein as MTSfra, having the amino acid sequence as denoted by SEQ ID NO. 22 and encoded by the nucleic acid sequence as denoted by SEQ ID NO. 2) or other defined MTSs of human mitochondrial proteins, including lipoamide dehydrogenase (referred to herein as MTSlad, having the amino acid sequence as denoted by SEQ ID NO. 24 and encoded by the nucleic acid sequence as denoted by SEQ ID NO. 5), C6ORF66 (referred to herein as MTSorf, having the amino acid sequence as denoted by SEQ ID NO. 25 and encoded by the nucleic acid sequence as denoted by SEQ ID NO. 4) and citrate synthase (referred to herein as MTScs, having the amino acid sequence as denoted by SEQ ID NO. 23 and encoded by the nucleic acid sequence as denoted by SEQ ID NO. 3). The various TAT-MTS-FRA fusion proteins are summarized in Table 4 below and schematically presented in FIG. 1.

All plasmids were cloned with His-tag at the 5'-terminus of the coding sequence and all coding sequences were under the control of the T7 promotor. All clones were confirmed by restriction enzymes and sequencing analyses.

TABLE 4

The cloned plasmid constructs

| No. | Plasmid name | Abbreviated name |
|---|---|---|
| 1 | His-TAT-MTSfra-FRA | FRA |
| 2 | His-TAT-MTSlad-FRA | (lad)FRA |
| 3 | His-TAT-MTSorf-FRA | (orf)FRA |
| 4 | His-TAT-MTScs-FRA | (cs)FRA |

Abbreviations: lad, Lipoamide dehydrogenase protein (E3 subunit); orf, C6ORF66 assembly factor; and cs, citrate synthase.

As indicated above, the amino acid sequences of the fusion proteins obtained from the cloned plasmid constructs indicated as 1-4 in Table 4 above are denoted by SEQ ID NO. 18, SEQ ID NO. 19, SEQ ID NO. 20 and SEQ ID NO. 17, respectively.

Example 2

Expression of the Fusion Proteins in *E. coli* Hosts

Expression of the fusion proteins was performed in *E. coli* hosts as described below and was calibrated for optimal expression conditions. As known in the art, there are several different bacterial expression systems. Successful expression of recombinant proteins is often dependent on the strain of the bacteria expression system used. Thus, for each fusion protein prepared as described above, four different *E. coli* bacterial stains were tested: BL21-CodonPlus, BL21, Rosetta and HMS (Invitrogen, USA) and the host for expression was thereby selected. The conditions for expression were also calibrated for each of the TAT-fusion proteins, by changing several parameters, including the concentration of the inducer Isopropyl β-D-1-thiogalactopyranoside (IPTG) and length of induction growth conditions (i.e. temperature, addition of chemicals, etc.)

Upon expression, bacterial cells were disrupted and cellular sub-fractions were prepared, separating the soluble and non-soluble fractions. Analysis was performed for the whole-cell bacteria (W.C. or whole-cell extract), the soluble fraction (Sol) and insoluble fraction (Insol) on sodium dodecyl sulfate polyacrylamide gel electrophoresis (SDS-PAGE) gels in order to examine whether the fusion protein was expressed and at which sub-cellular fraction it accumulates. The goal was to obtain high expression levels of the different TAT-fusion proteins in the soluble sub-fraction of the expressing bacteria, for future purification. The different TAT-fusion proteins were also characterized by Western blots analyses using both anti-His and anti-frataxin antibodies. Table 2 above summarizes the bacterial host, IPTG concentration and temperature for production of each TAT-MTS-FRA fusion proteins carrying a different MTS sequence.

Figure 2B:
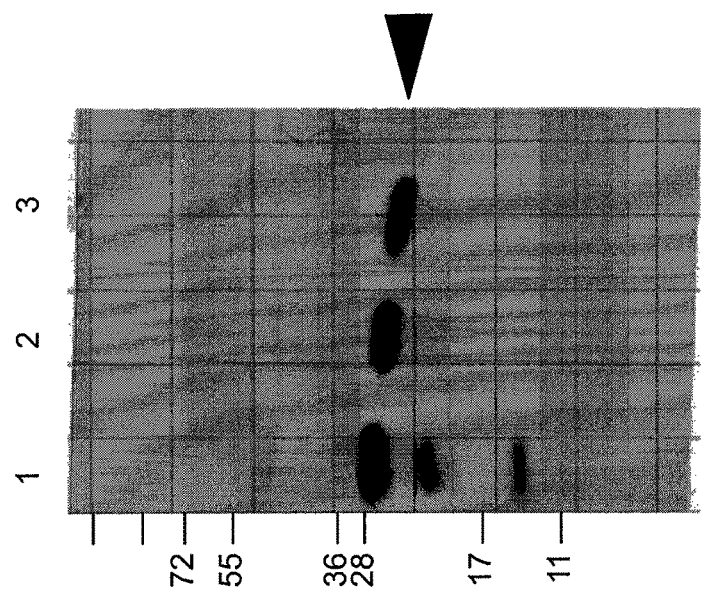
Figure 2A:
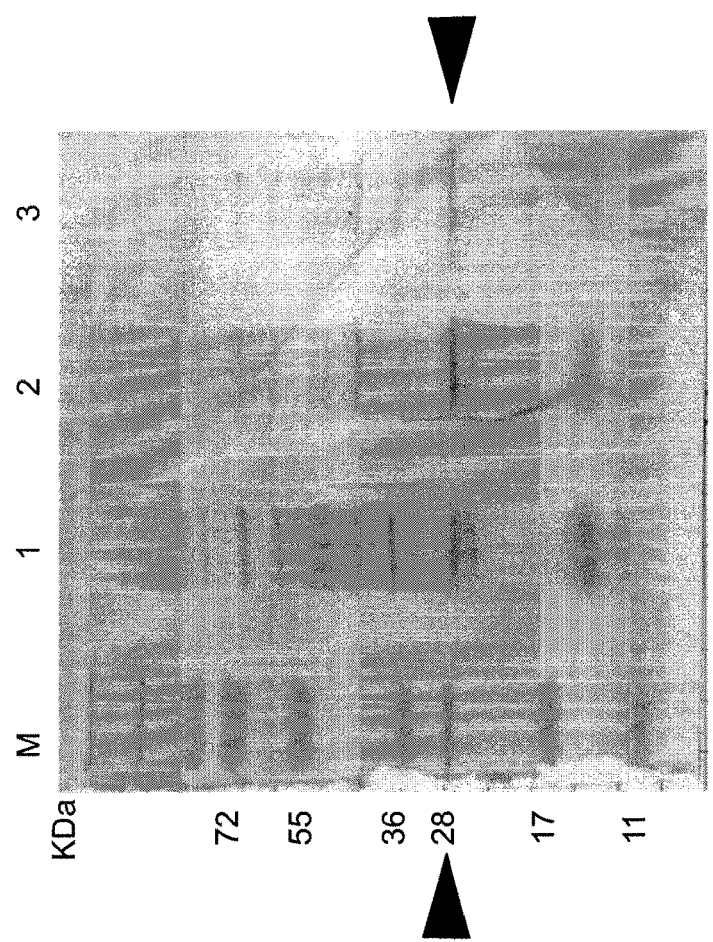
Figure 3B:
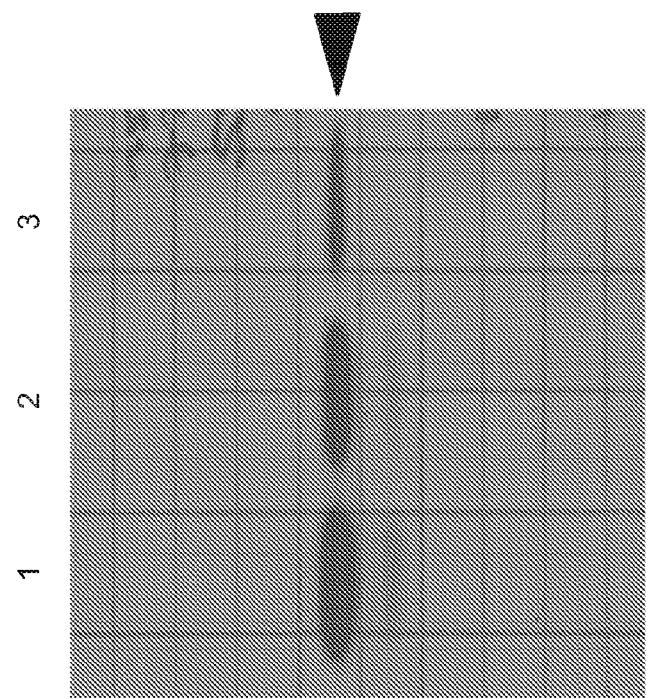
Figure 3A:
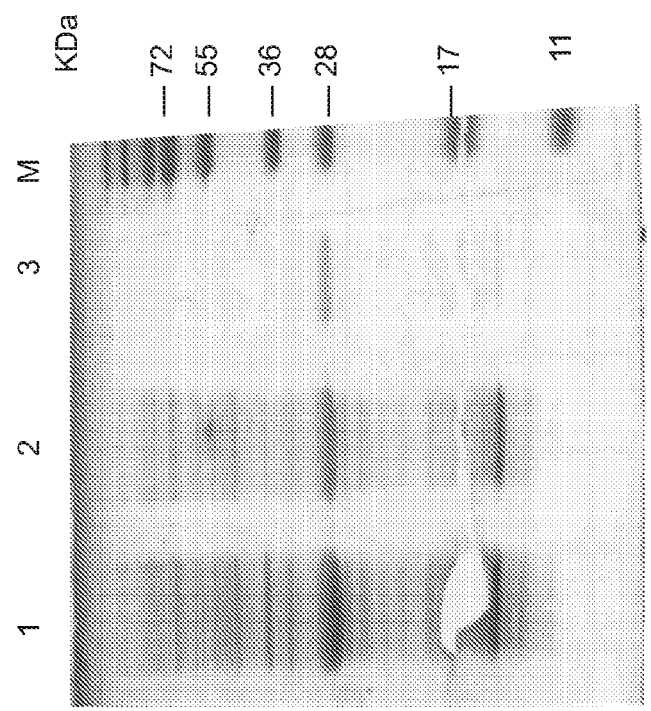
Figures 3C, 3D:
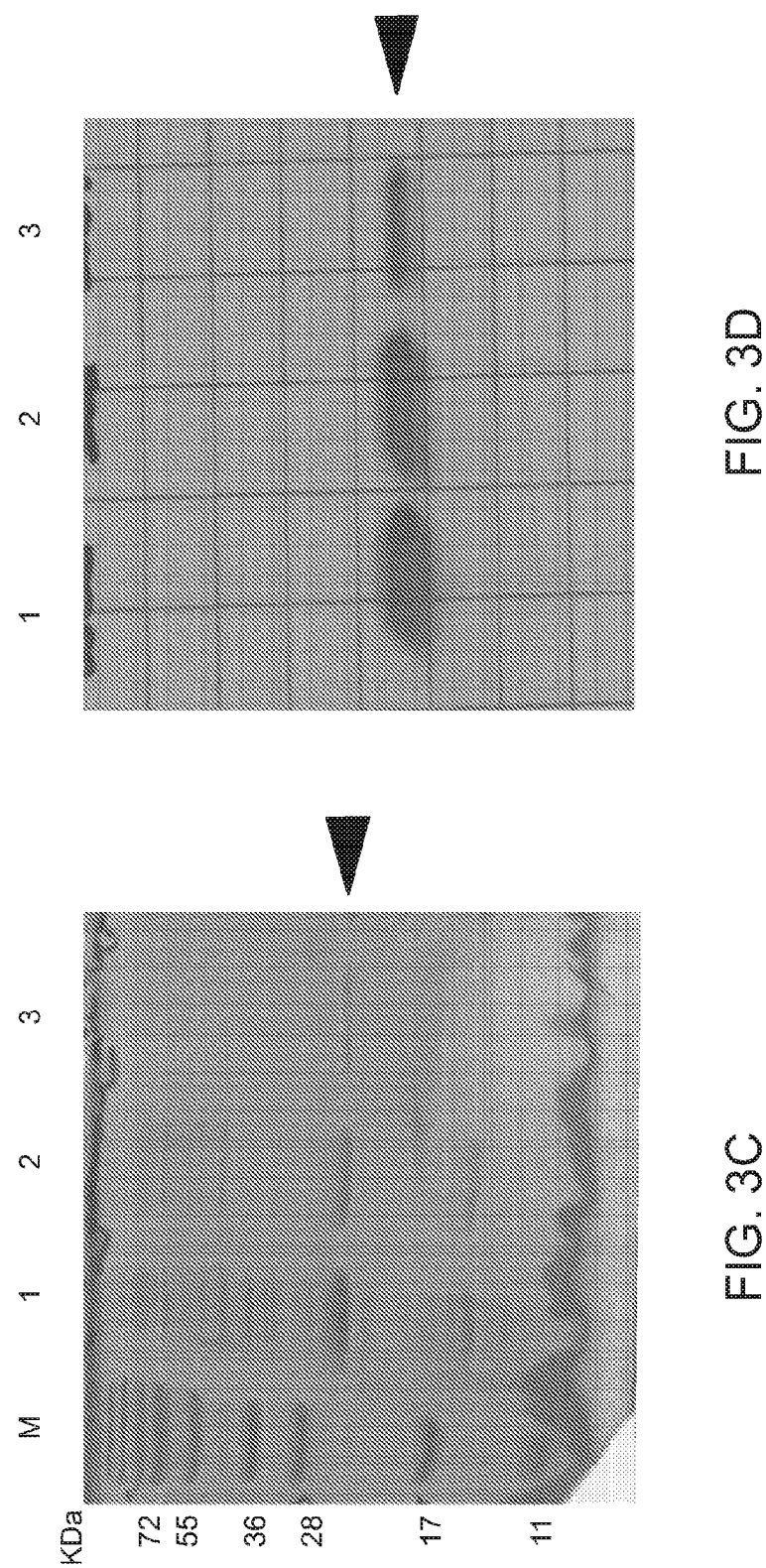

Typical expression and sub-cellular localization of each of the four fusion proteins as characterized by SDS-PAGE gels and Western blots using anti-His antibodies are demonstrated in FIG. 2 and in FIG. 3. Expression of the His-TAT-MTSfra-FRA fusion protein is shown in FIG. 2A-2B, Expression of the His-TAT-MTSorf-FRA fusion protein is shown in FIG. 2C-2D, Expression of the His-TAT-MTSlad-FRA fusion protein is shown in FIG. 3A-3B and Expression of the His-TAT-MTScs-FRA fusion protein is shown in FIG. 3C-3D. These experiments confirmed the full-length expression of the different TAT-fusion proteins and their identity.

It should be pointed out the anti-His antibodies recognize, most probably, the various fusion proteins with different efficacy, depending on the exposure or availability of the His sequence in the final protein preparation, for antibody interactions. Thus, expression levels of the various fusion proteins are determined based on the SDS-PAGE gels.

As can be seen in FIG. 2 and in FIG. 3, the TAT-MTSfra-FRA fusion protein (FIG. 2A & FIG. 2B) was expressed at low levels in the bacterial hosts, as compared to the other three fusion proteins carrying an heterologous MTS (FIG. 2C & FIG. 2D and FIG. 3A-3D), even under the best calibrated conditions. Thus, using a heterologous MTS instead of the native frataxin-MTS has an advantage in its expression levels in a bacterial host. This has major implications on its future development for human use, where large quantities of the fusion protein are needed to be produced (see also below).

Example 3

Purification of the TA T-MTS-FRA Fusion Proteins

The soluble fractions of the expressed TAT-MTS-FRA fusion proteins were loaded onto a nickel-chelating column to affinity-purify these proteins, as detailed above. Calibration experiments were performed for each of the fusion proteins, including specific conditions for binding of the fusion protein onto the affinity column, its elution and removal of the imidazole from the final protein preparations. One typical purification run of each of the fusion proteins is demonstrated in FIG. 4 (for His-TAT-MTSfra-FRA and His-TAT-MTSorf-FRA) and in FIG. 5 (for His-TAT-MTSlad-FRA and His-TAT-MTScs-FRA).

Figure 4A:
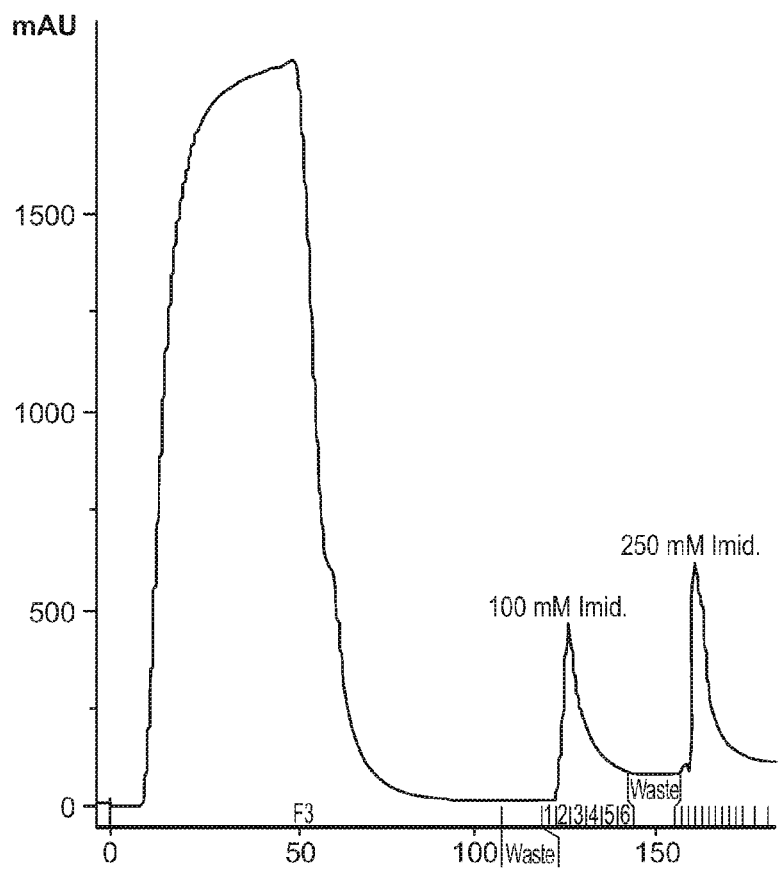
Figure 4B:
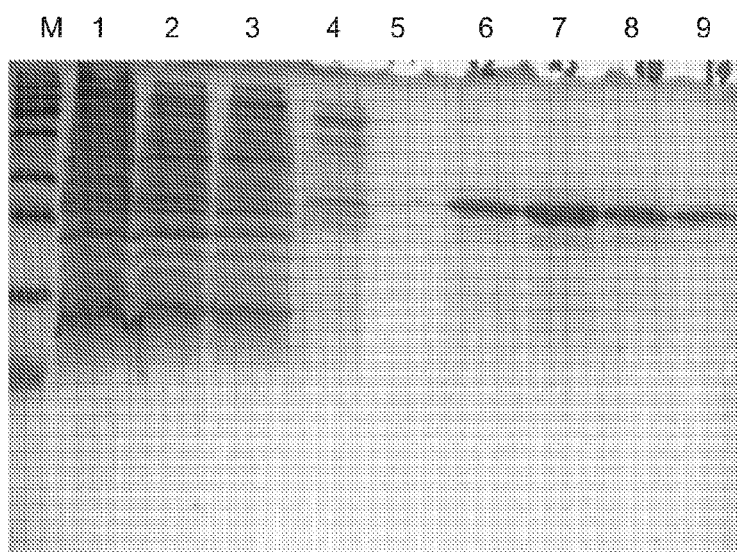

For example, FIG. 4A shows an image of an affinity chromatography purification profile obtained for the fusion protein TAT-MTSfra-FRA. As can be seen in FIG. 4B, which is an image of SDS-PAGE analysis of the purification steps of this protein construct, the protein fraction shown in FIG. 4B, lane 7, represents the fusion protein TAT-MTSfra-FRA that was eluted from the column at 250 mM imidazole.

Figure 4C:
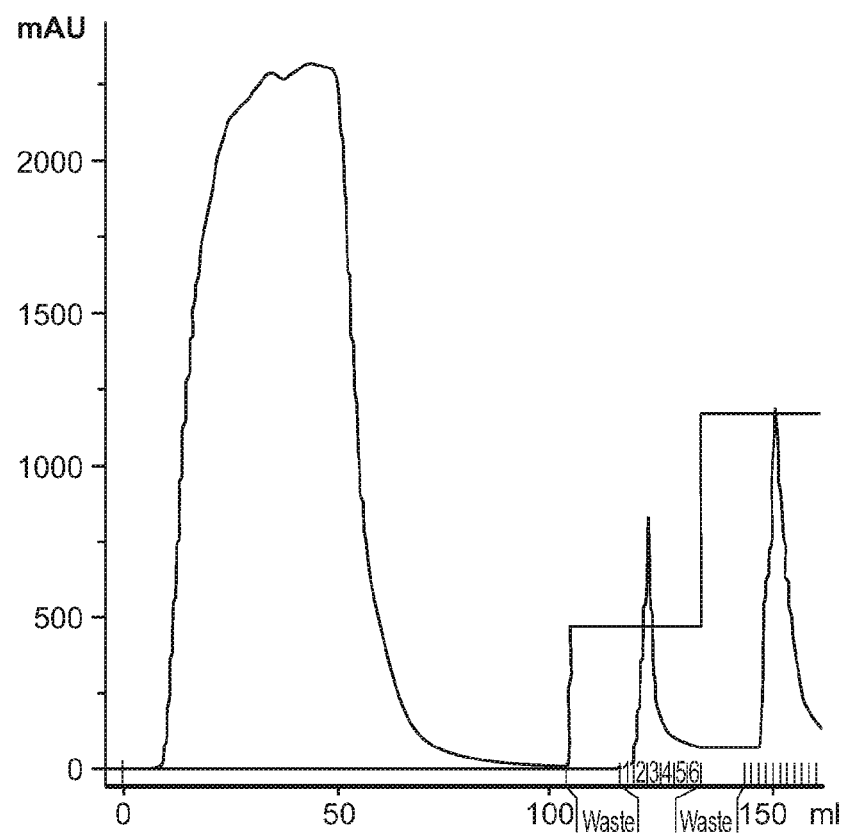
Figure 4D:
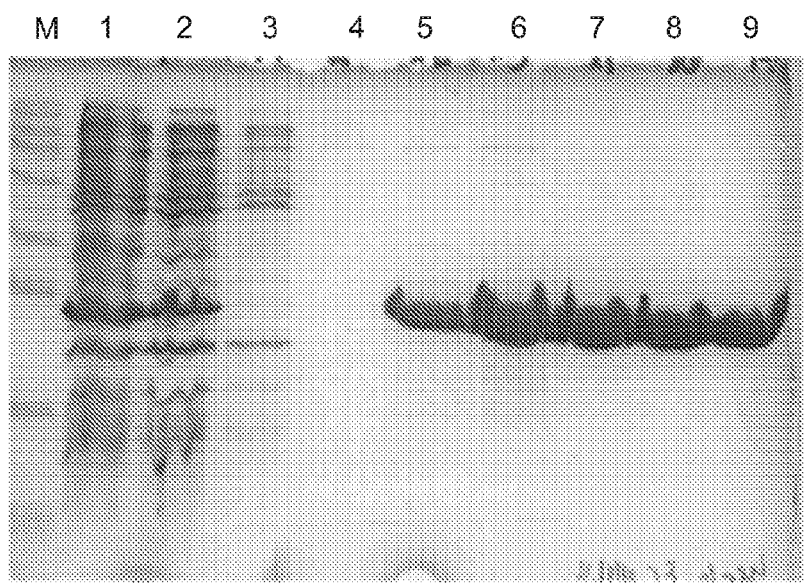
Figure 5C:
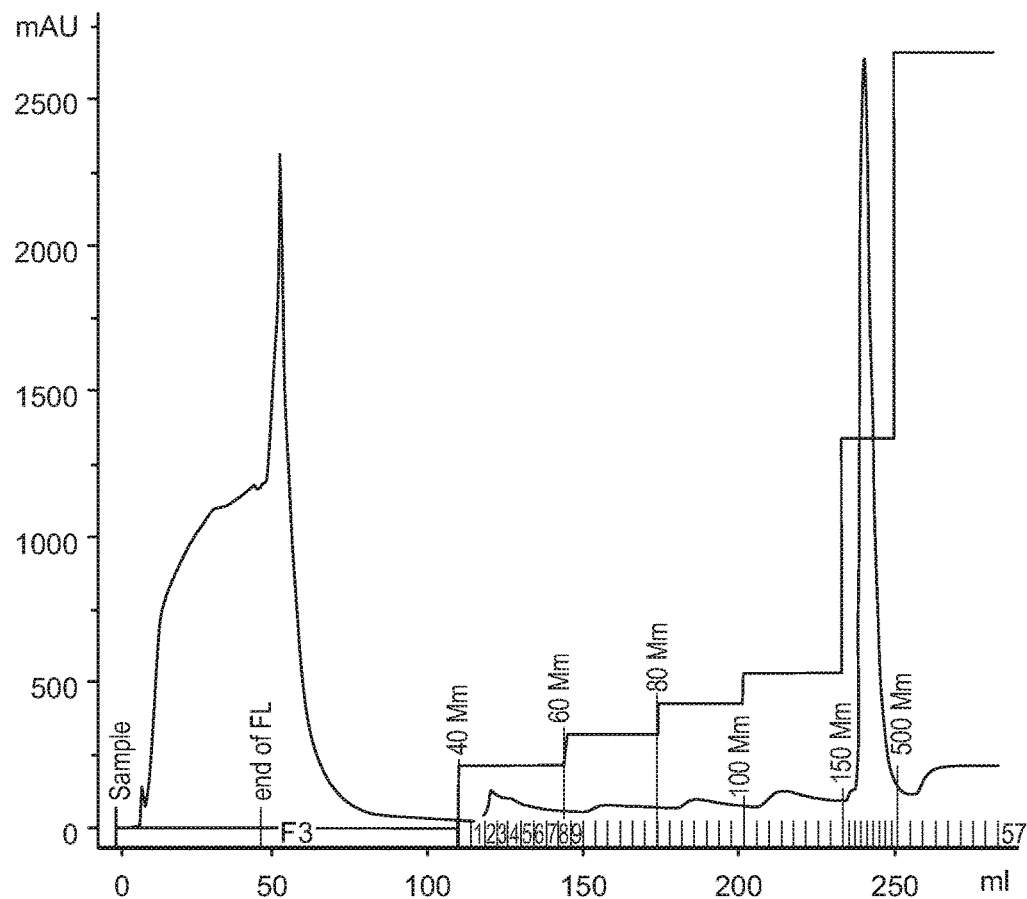
Figure 5D:
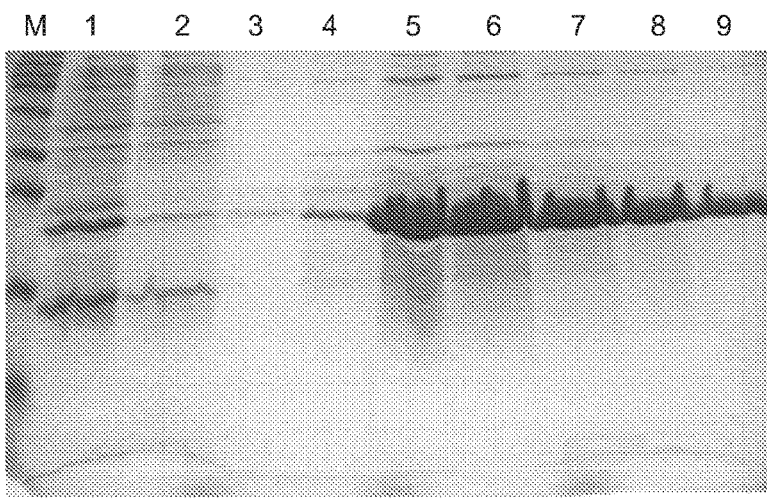

Corresponding analyses are shown for TAT-MTSorf-FRA in FIG. 4C and FIG. 4D, for TAT-MTSlad-FRA in FIG. 5A and FIG. 5B and for TAT-MTScs-FRA corresponding analyses are shown in FIG. 5C and FIG. 5D.

As shown in FIG. 6A, eluted proteins showed a major band of the expected size (approximately 20-27 kDa) and were >95% pure, as determined by SDS-PAGE analysis and by Western blot analyses using both anti-His (FIG. 6B) and anti-Fra antibodies (FIG. 6C). As can be seen in FIG. 6, TAT-MTS-FRA fusion proteins carrying a heterologous MTS were full-length, intact proteins with no evidence for protein degradation (see lane 2 for TAT-MTScs-FRA, lane 3 for TAT-TSlad-FRA and lane 4 for TAT-MTSorf-FRA). However, TAT-MTSfra-FRA carrying the native MTS sequence was partially degraded (see lane 1 in FIG. 6B and in FIG. 6C). Thus, using a heterologous MTS sequence for the TAT-FRA fusion protein has an advantage also for keeping the fusion protein intact and stable.

In addition, when comparing the total amounts and concentrations of each of the fusion proteins, which were produced from the same starting volume of bacterial cultures, fusion proteins carrying an heterologous MTS were produced in larger amounts and at higher concentration as compared to that of fusion protein carrying the native MTS (Table 5, below). This has again major implications on its future development for human use, where large quantities of the fusion protein are needed and at high concentrations. Moreover, the stability of the produced fusion protein has an additional advantage.

TABLE 5

TAT-MTS-FRA fusion proteins

| Protein | Final concentration (mg/ml) | Amount purified from 0.5 L bacterial culture (mg) |
| --- | --- | --- |
| TAT-MTSfra-FRA | 0.2 | 0.6-0.7 |
| TAT-MTScs-FRA | 1.0 | 3-4 |
| TAT-MTSorf-FRA | 1.0 | 3-4 |
| TAT-MTSlad-FRA | 0.8 | 2.4-3.2 |

Example 4

Internalization of TA T-MTS-FRA Fusion Proteins

In order to test the ability of the fusion protein to reach the mitochondria within intact cells, human BJAB cells were incubated with one of the purified fusion proteins, namely, TAT-MTSlad-FRA. After incubation, sub-cellular fractions were prepared, to separate the mitochondria and the cytosol. The mitochondria were then treated with proteinase K (Sigma P2308) to digest proteins nonspecifically adsorbed to the outer membrane, thereby ensuring that the mitochondrial extract represented only proteins within the mitochondria. Samples were then analyzed by Western blot assay for the presence of the FRA-based fusion protein, using both anti-His and anti-FRA antibodies (see FIG. 7).

As shown in FIG. 7A, using anti-His antibodies the results indicated the presence of the His-tagged TAT-MTSlad-FRA fusion protein within the mitochondrial fractions of the treated cells after 1 and 5 hours of incubation (lane 4 and lanes 6 & 7, respectively).

As shown in FIG. 7B, using anti-FRA antibodies, the presence of a frataxin fusion protein construct inside the mitochondria is indicated. From lane 2 of FIG. 7B it is evident that control cells that were not treated with the fusion protein have endogenous FRA protein, most probably, both the mature isoform and the intermediate isoform (indicated by the two arrows).

As shown in FIG. 7B (lanes 4, 6, 7), upon treatment with the TAT-MTSlad-FRA fusion protein, the relative amounts of both the unprocessed fusion protein as well as of the mature protein increased with the incubation time (FIG. 7B; upper and lower bands, respectively). Without wishing to be bound by theory, the increase in the upper band is explained by fusion protein construct that entered the mitochondria and was not processed.

Internalization of fusion proteins comprising frataxin into the mitochondria of cells was examined also for other TAT-MTS-FRA fusion proteins, namely, TAT-MTSfra-FRA, TAT-MTScs-FRA, and TAT-MTSorf-FRA (as well as for TAT-MTSlad-FRA), as shown in FIG. 8A. In this experiment, cells were incubated for 3 hours with each of the TAT-MTS-FRA fusion proteins (at a final concentration of 0.02 µg/µl). The cells were then washed, their mitochondria were isolated and then submitted to Western blot analysis using monoclonal anti-FRA antibodies (Abnova, Taiwan; 1 µg/ml) that are directed to the C-terminus of the frataxin protein.

As demonstrated in FIG. 8A, lanes 2-5, a slight size variation was observed among the various fusion protein constructs, resulting from the variation in the length of the various MTS polypeptides (see FIG. 1).

As shown in FIG. 8A, internalization into mitochondria was observed for all four TAT-MTS-FRA fusion proteins. Remarkably, as shown in lane 3 of FIG. 8A, among the fusion proteins with a MTS that is heterologous to frataxin, the citrate synthase MTS (MTScs) was demonstrated to be delivered most efficiently into the mitochondria.

As indicated above, there is a slight variation in the lengths of the fusion protein constructs that entered the mitochondria, indicating that under the present experimental conditions (namely incubation of cells for 3 hours with each of the TAT-MTS-FRA fusion proteins) the frataxin protein was not cleaved from its respective His-TAT-MTS-frataxin construct inside the mitochondria (protein constructs that still include intact His-TAT-MTS-frataxin are termed below as "un-processed fusion construct").

Notably, FIG. 8A also shows that while for the fusion proteins comprising an MTS which is heterologous to frataxin, namely the MTS of citrate synthase (cs), lipoamide dehydrogenase (lad) and C6ORF66 (orf), only a single band (representing the un-processed fusion construct) was demonstrated inside the mitochondria, two distinct bands appeared for the fusion protein comprising the native MTS of frataxin (FIG. 8A, lane 2). Without wishing to be bound by theory, this may be the result of instability of the intact fusion protein comprising the TAT and native frataxin MTS regions.

The antibodies used to detect frataxin in the internalization assay presented in FIG. 7B were polyclonal antibodies directed against human frataxin. These antibodies recognize the full-length, unprocessed human frataxin very well, as well as its processed products. In FIG. 8 referred to below, detection was performed using monoclonal antibodies specifically directed against the C-terminus of the frataxin protein. As these monoclonal antibodies are less efficient in recognizing the protein, particularly at the amounts of protein detected in FIG. 8, the results of FIG. 7 and FIG. 8 cannot be compared.

Control Western blot analysis using anti-E1α antibodies (Molecular Probes, Eugene, Oreg.) at a dilution of 1:1,000) are demonstrated in FIG. 8B.

Example 5

His-TAT-MTS(Cs)-FRA Enter the Mitochondria of Patients' fibroblasts

Further to the above results demonstrating the ability of the frataxin fusion proteins to enter mitochondria of human BJAB cells, the internalization of a frataxin fusion protein comprising the MTS of citrate synthase into the mitochondria of fibroblasts obtained from Friedreich's ataxia patients was examined, as detailed below.

Fibroblasts obtained from Friedreich's ataxia patients were treated as described above and incubated in the presence of His-TAT-MTS(cs)-FRA (at 20 µg/ml) for 2, 6 and 48 hours, with fresh addition after 24 hours. Mitochondrial and cytosolic fractions of the fibroblasts were analyzed by Western blot analysis as described above.

As demonstrated in FIG. 9, the fusion protein construct His-TAT-MTS(cs)-FRA was detected in mitochondrial fractions of fibroblasts after an incubation of 2, 6 and 48 hours. The two bands detected by the anti-frataxin antibody (indicated by the upper and lower arrows in FIG. 9) indicate that the fusion protein was processed inside mitochondria. Frataxin was not detected in the cytosolic fractions of the fibroblasts indicating that all of the His-TAT-MTS(cs)-FRA fusion protein construct has entered mitochondria.

Example 6

Aconitase Activity in Fibroblasts Obtained from Patients Following Administration of His-TAT-MTS(cs)-FRA It has been reported that the reduction in the levels of frataxin within the mitochondria has two direct effects on several tissue types, namely impaired formation of iron-sulfur (Fe—S) clusters and a rise in intracellular reactive oxygen species (ROS) [35]. The decrease in Fe—S containing proteins, such as heme, electron transport chain (ETC) complexes I-III and the Kreb's cycle protein aconitase severely impairs cellular respiration [36], which is further complicated by simultaneous oxidative damage to these mitochondrial proteins. These events all culminate in an inability of the mitochondria to fulfill the cell's energy requirements resulting in cell death [35].

In order to assess the activity of frataxin inside mitochondria, the level of aconitase activity in mitochondria obtained from Friedreich's ataxia patients was examined upon administration of His-TAT-MTS(cs)-FRA.

Aconitase activity (mOD/min) was measured by following the conversion of isocitrate to cis-aconitate, as described above, in mitochondrial fractions of fibroblasts (F816) obtained from Friedreich's ataxia patients that were treated as described above and incubated in the presence of His-TAT-MTS(cs)-FRA or vehicle for 48 hours (FXN or VEH, respectively). His-TAT-MTS(cs)-FRA was administered at 20 µg/ml and an additional dose of 20 µg/ml was administered 24 hours after the first administration). HepG2 whole cells homogenate served as positive control (POS.CON).

As shown in FIG. 10, aconitase activity was higher in fibroblasts that were incubated with His-TAT-MTS(cs)-FRA (FXN, 14.5) compared to fibroblasts that were incubated in the presence of the vehicle control (VEH, 10.5). This finding is a clear demonstration that the fusion protein not only enters mitochondria, but is also active and available for its various cellular activities.

HepG2 whole cells homogenate served as positive control (POS.CON).

Example 7

TAT-MTS-FRA Fusion Proteins Partially Rescue FA-Patients' Cells as Well as Normal Cells from Oxidative Stress As indicated above, the reduction in the levels of frataxin within the mitochondria leads to a rise in intracellular reactive oxygen species (ROS) [35].

L-Buthionine sulphoximine (BSO) is an inhibitor of gamma-glutamylcysteine synthetase (gamma-GCS) and, consequently lowers tissue glutathione (GSH) concentrations. GSH plays an important role in cellular defense or protection against a wide variety of toxic electrophiles via the formation of thioether conjugates. Therefore, BSO assay was used to inhibit de novo glutathione synthesis, depleting an important component of these cells' intrinsic defenses against reactive oxygen species (ROS) and allowing for the accumulation of ROS produced by natural cell processes, known to result in cell death [37]. The mechanism by which BSO inhibits production of GSH and results in cell death was described by Richardson, T. E. et al. [37]. Because they are lacking in Frataxin, Friedreich ataxia cells are extremely sensitive to BSO-induced oxidative stress compared with normal cells [37], and thus are used as an in vitro model of the long-term consequences of absent Frataxin.

Oxidative stress was induced with various concentrations of BSO in patients' cells as well as in normal healthy cells and the effect of the various TAT-MTS-FRA fusion proteins on cell death was measured. As can be seen in FIG. 11, BSO caused cell death of normal lymphocytes as well as of cells obtained from Friedreich ataxia patients. However, patients' cells were more sensitive to BSO-induced oxidative stress, consistent with previous findings, showing higher percentages of cell death. Most importantly, the various TAT-MTS-FRA fusion proteins, which were added a few hours before oxidative stress induction, were demonstrated to partially rescue both normal lymphocytes as well as patients' cells from cell death. This partial rescue was determined by both reduction in cell death and by reduction in caspase 3 activity, as demonstrated in FIG. 11B.

As shown in FIG. 11A and FIG. 11B, at least two out of the three fusion proteins carrying a heterologous MTS (namely, MTSorf and MTScs) demonstrated a superior protective effect with respect to the effect demonstrated by the fusion protein carrying the native MTS, in both patients' cells as well as in healthy cells, from BSO-induced oxidative stress.

A comparative study of the ability of the various TAT-MTS-FRA fusion proteins to rescue BSO-induced oxidative stress of patients' fibroblasts performed as detailed above is shown in FIG. 12A-FIG. 12D for the fusion protein constructs TAT-MTSfra-FRA, TAT-MTScs-FRA, TAT-MTSlad-FRA and TAT-MTSorf-FRA, respectively.

Interestingly, as demonstrated in FIG. 12B and in FIG. 12C, respectively, two of the protein constructs comprising heterologous MTS, namely the TAT-MTScs-FRA and TAT-MTSlad fusion proteins were more efficient than the fusion protein comprising the native frataxin MTS (TAT-MTSfra-FRA) in partially rescuing BSO-induced oxidative stress of patients' fibroblasts.

Similar protective effects in patients' cells induced with various concentrations of BSO were also observed for TAT-MTSorf-FRA and TAT-MTSlad fusion proteins when assayed alone (FIG. 13 and FIG. 14, respectively).

Example 8

Pharmacodynamic and Pharmacokinetic Assessment of TAT-MTS-FRA Fusion Proteins in Friedreich's Ataxia Mice In an ongoing study, in order to evaluate pharmacodynamic, pharmacokinetic (PK/PD) and safety of TAT-MTS-FRA fusion proteins in a Friedreich's ataxia preclinical mouse model, the mouse model JR#18299 FVB; B6-Tg(FXN)1Sars Fxn$_{tm1Mkn}$/J is used in an ongoing study. The information obtained from these studies will be used for determining dose and time interval for further clinical studies. Briefly, the study requires 45 female mice, 6-8 weeks of age that are homozygous for the targeted mutation at the mouse Frataxin locus and hemizygous for the transgene. It is noted that strain 18299 is the original Sarsero mouse on a mixed genetic background, which was selected over the original C57BL/6J congenic strain due to its superior breeding performance and since no behavioral phenotyping is performed in this study.

In order to perform the preclinical study, two doses of TAT-MTScs-FRA fusion protein (at 100 μg and 400 μg) are administered twice per week for a maximal period of three weeks along with a vehicle, via tail vein injection into 18229 FVB; B6-Tg(FXN)1Sars Fxntm1Mkn/J mice. Mice are sacrificed 1, 4, 7, 14 or 21 days post injection and then blood is collected by cardiac puncture and various tissues are harvested (e.g. brain, heart, liver and kidney). Brain and heart tissue are processed to measure aconitase activity. Brain and heart tissue are also processed to measure frataxin levels by ELISA assay in mitochondrial extracts. Blood, liver and kidney are flash-frozen and stored.

The effect of the treatment is then assessed in the harvested tissues.

Example 9

TAT-MTS-OTC Protein Constructs Internalize into Mitochondria

Fusion protein constructs comprising OTC fused to a His-TAT-MTS were prepared as described above. As shown in FIG. 16, purified fusion protein constructs comprising the native MTS of OTC, the MTS of citrate synthase, the MTS of C6ORF66 and the MTS of lipoamide dehydrogenase were obtained (FIG. 16A, FIG. 16B, FIG. 16C and FIG. 16D, respectively). The size of the purified fusion protein constructs obtained was about 40 kDa as determined based on comparing their gel migration to the migration of the protein marker shown in FIG. 16E,). Similar expression yields were obtained for all four fusion protein constructs that were prepared.

In order to examine the ability of the various OTC fusion protein constructs to enter mitochondria, HepG2 cells were incubated in the presence of the OTC fusion proteins constructs comprising either the native MTS of OTC or an MTS that is heterologous to OTC, namely, His-TAT-MTSotc-OTC, His-TAT-MTScs-OTC and TAT-MTSlad-OTC as described above.

First, as shown in FIG. 17A, it is noteworthy that the fusion protein constructs His-TAT-MTSotc-OTC, His-TAT-MTScs-OTC and His-TAT-MTSlad-OTC (and His-TAT-MTSorf-OTC, data not shown) were soluble under the various assay conditions based on the fact that no precipitation or degradation products were detected.

Analysis of mitochondrial fractions of HepG2 cells incubated with the above constructs revealed that the OTC fusion protein construct comprising the native MTS of OTC (His-TAT-MTSotc-OTC) as well as the OTC fusion protein constructs comprising an MTS that is heterologous to the OTC protein, namely citrate synthase (cs) and lipoamide dehydrogenase (lad) were able to enter mitochondria after an incubation period of 1 hour (FIG. 17A). FIG. 17A also shows that prolonging the incubation period to 3 hours resulted in an increase in the level of the fusion protein construct inside the mitochondria.

Interestingly, by comparing the ability of the protein construct comprising the native MTS of OTC (His-TAT-MTSotc-OTC) to the ability of OTC fusion protein constructs comprising an MTS that is heterologous to the OTC protein (namely His-TAT-MTScs-OTC and His-TAT-MTSlad-OTC) for example upon incubation of 3 hours in EMEM, it appears that the internalization ability of the fusion protein constructs comprising an MTS that is heterologous to OTC was slightly higher than the internalization ability of the fusion protein construct comprising the native MTS of OTC.

In order to further confirm the internalization of the OTC fusion protein constructs into mitochondria, the cytosolic fractions of the cells incubated with the various His-TAT-MTS-OTC protein constructs were also analyzed. As shown in FIG. 18A and FIG. 18B, no fusion protein constructs were observed in any of the assayed cytosolic fractions.

Example 10

In Vitro Enzymatic Activity of OTC

As indicated above, OTC is a protein having enzymatic activity that catalyzes the reaction between carbamoyl phosphate and ornithine to form citrulline and phosphate. In order to assess the activity of the purified fusion protein constructs comprising OTC described herein above, the production of citrulline from ornithine and carbamoyl phosphate by various fusion protein constructs was evaluated, as described above.

As shown in FIG. 19, the fusion protein construct His-TAT-MTScs-OTC assayed had relatively low enzymatic activity, where the fusion protein construct His-TAT-MTSotc-OTC had none. Without wishing to be bound by theory, this may be due to the fact that OTC is probably not present in the reaction mixture at its native trimeric state, which is necessary for its enzymatic activity, since it is conjugated to a His-TAT-MTS fragment.

However, as shown in FIG. 19 a low level of enzymatic activity was indeed observed for the fusion protein construct comprising the MTS of CS.

Example 11

Enzymatic Activity of OTC in HepG2 Cells Suffering from Ammonia Stress

OTC deficiency is the most common urea cycle disorder in humans. OTC, the defective enzyme in this disorder, is the final enzyme in the proximal portion of the urea cycle, and is responsible for converting carbamoyl phosphate and ornithine into citrulline, as indicated above. In severely affected individuals, ammonia concentrations increase rapidly causing ataxia, lethargy and death without rapid intervention.

In order to test the ability of the OTC fusion protein constructs to rescue ammonia stress in cells, HepG2 cells were administered daily (for 3 days) with a fusion protein construct comprising the native MTS of OTC or with fusion protein construct comprising the MTS of CS then treated with ammonium chloride, and finally, their cell viability was evaluated using the alamarBlue indicator, as described above.

As shown in FIG. 20, the level of cell viability in the presence of fusion protein constructs comprising OTC and citrate synthase as the MTS was similar to the level of cell viability for cells which were not exposed to ammonium chloride (untreated cells). Furthermore, the level of cell viability in the presence of a fusion protein construct comprising OTC and citrate synthase as the MTS was higher from the level of cell viability in cells treated with the fusion protein construct comprising the native MTS of OTC.

Taken together, the above results demonstrate that fusion protein constructs comprising TAT, MTS and OTC and in particular such fusion protein which comprise an MTS which is heterologous to OTC are able to enter mitochondria, the OTC is then processed, thereby enabling its enzymatic activity.

The results also indicated that the fusion protein constructs without ammonia were not cytotoxic (data not shown).

Example 12

Kinetics of Liver Entry and Dose Determination of TAT-MTS-OTC Fusion Protein Constructs in Mice In order to assess the kinetics of liver entry of OTC, liver levels of any of the TAT-MTS-OTC fusion protein constructs described herein are determined in OTC-deficient spf$^{ash}$ mice (3 hemizygous males and 3 homozygous females at group) 4, 8, 24 and 48 hours after administration of a fusion protein construct comprising OTC (500 μg/mouse). Liver pieces and other tissues (e.g. skeletal muscle, brain) are then harvested and analyzed for their OTC protein levels by Western blot analysis. In addition, the activity of OTC is examined in harvested liver, by using an OTC enzymatic assay (for example the citrulline assay described above).

Blood is collected by cardiac puncture and plasma is isolated for liver function tests (ALT/AST), amino acids (including citrulline), ammonia determination and OTC protein levels (Western blot). Urine is collected for orotic acid analysis.

Male mice are used for further studies in case the above experiments do not indicate any differences between males and females.

Then, protein levels are determined in tissues of mice administered with various doses of a TAT-MTS-OTC fusion protein construct (100-500 μg/mouse) at the time point for which the highest OTC protein levels were detected in the above assay.

Example 13

Phenotype Protection by TAT-MTS-OTC Fusion Protein Constructs

OTC-deficient spf$^{ash}$ mice (6 males or 3 males and 3 females) are administered with OTC-shRNA knockdown rAAV according to Cunningham, S. C. et al. [41]. At a designated time-point (based on the activity of the OTC-shRNA batch and results obtained from the above experiments) dosing with a TAT-MTS-OTC fusion protein construct is commenced by administering 0, 1, 2 or 3 dose(s) per week to each tested group of mice.

Analysis is performed by first measuring baseline plasma levels of ammonia, amino acids (including citrulline) and ALT/AST as well as urinary orotic acid prior to injection of OTC-shRNA knockdown rAAV (blood is collected via tail vein nicking). Blood and urine are collected again prior to administration of a TAT-MTS-OTC fusion protein construct for the above analyses and then weekly for the duration of the experiment.

Mice are monitored and sacrificed upon observation of clinical signs of hyperammonaemia (lethargy, tremors, ataxia) or 1 month post-injection of a TAT-MTS-OTC fusion protein construct. At the termination of the experiment, liver, muscle and brain are frozen in liquid nitrogen or fixed in 4% PFA for vector copy analysis (quantitative PCR), OTC activity (in liver lysate and frozen sections) and protein levels (Western blot).

The invention claimed is:

1. A fusion protein comprising an HIV-1 transactivator of transcription (TAT) domain fused to human ornithine transcarbamoylase (OTC) and a mitochondria targeting sequence (MTS) of human citrate synthase situated between said TAT domain and said OTC, wherein said OTC is C-terminal to said MTS of human citrate synthase.

2. The fusion protein according to claim 1, further comprising a linker covalently linking said TAT domain to said MTS.

3. A pharmaceutical composition comprising a pharmaceutically acceptable carrier and the fusion protein according to claim 1 as an active ingredient.

4. A fusion protein having the amino acid sequence denoted by SEQ ID NO: 49, comprising a HIV-1 transactivator of transcription (TAT) domain having the amino acid sequence denoted by SEQ ID NO: 27 fused to human ornithine transcarbamoylase (OTC) having the amino acid sequence denoted by SEQ ID NO: 39 and a mitochondria targeting sequence (MTS) of human citrate synthase having the amino acid sequence denoted by SEQ ID NO: 23, said MTS situated between said TAT domain and said OTC, and is linked to said TAT domain via a linker having the amino acid sequence denoted by SEQ ID NO: 32, and wherein said OTC is C-terminal to said MTS of human citrate synthase.

5. A pharmaceutical composition comprising a pharmaceutically acceptable carrier and the fusion protein according to claim 4 as an active ingredient.

6. A method for introducing a human ornithine transcarbamoylase (OTC) protein into a subject, comprising administering to the subject the fusion protein according to claim 1.

7. The method of claim 6, wherein the fusion protein further comprises a linker covalently linking said TAT domain to said MTS.

* * * * *

SEQUENCE LISTING

<160> NUMBER OF SEQ ID NOS: 54

<210> SEQ ID NO 1
<211> LENGTH: 27
<212> TYPE: DNA
<213> ORGANISM: Human immunodeficiency virus type 1

<400> SEQUENCE: 1
aggaagaagc ggagacagcg acgaaga                                        27

<210> SEQ ID NO 2
<211> LENGTH: 237
<212> TYPE: DNA
<213> ORGANISM: Homo sapiens

<400> SEQUENCE: 2
tggactctcg ggcgccgcgc agtagccggc ctcctggcgt cacccagccc ggcccaggcc    60
cagaccctca cccgggtccc gcggccggca gagttggccc cactctgcgg ccgccgtggc   120

```
ctgcgcaccg acatcgatgc gacctgcacg ccccgccgcg caagttcgaa ccaacgtggc    180
ctcaaccaga tttggaatgt caaaaagcag agtgtctatt tgatgaattt gaggaaa      237

<210> SEQ ID NO 3
<211> LENGTH: 78
<212> TYPE: DNA
<213> ORGANISM: Homo sapiens

<400> SEQUENCE: 3
gctttactta ctgcggccgc ccggctcttg ggaaccaaga atgcatcttg tcttgttctt    60
gcagcccggc atgccagt                                                  78

<210> SEQ ID NO 4
<211> LENGTH: 102
<212> TYPE: DNA
<213> ORGANISM: Homo sapiens

<400> SEQUENCE: 4
ggagcactag tgattcgcgg tatcaggaat ttcaacctag agaaccgagc ggaacgggaa    60
atcagcaaga tgaagccctc tgtcgctccc agacacccct ct                      102

<210> SEQ ID NO 5
<211> LENGTH: 105
<212> TYPE: DNA
<213> ORGANISM: Homo sapiens

<400> SEQUENCE: 5
cagagctgga gtcgtgtgta ctgctccttg gccaagagag gccatttcaa tcgaatatct    60
catggcctac agggactttc tgcagtgcct ctgagaactt acgca                   105

<210> SEQ ID NO 6
<211> LENGTH: 393
<212> TYPE: DNA
<213> ORGANISM: Homo sapiens

<400> SEQUENCE: 6
tctggaactt tgggccaccc aggctctcta gatgagacca cctatgaaag actagcagag    60
gaaacgctgg actctttagc agagtttttt gaagaccttg cagacaagcc atacacgttt   120
gaggactatg atgtctcctt tgggagtggt gtcttaactg tcaaactggg tggagatcta   180
ggaacctatg tgatcaacaa gcagacgcca acaagcaaa tctggctatc ttctccatcc    240
agtggaccta agcgttatga ctggactggg aaaaactggg tgtactccca cgacggcgtg   300
tccctccatg agctgctggc cgcagagctc actaaagcct taaaaccaa actggacttg   360 tcttccttgg cctattccgg aaaagatgct tga                                393

<210> SEQ ID NO 7
<211> LENGTH: 27
<212> TYPE: DNA
<213> ORGANISM: Artificial Sequence
<220> FEATURE:
<223> OTHER INFORMATION: forward primer for precursor frataxin cloning

<400> SEQUENCE: 7
cgcggatccg tggactctcg ggcgccg                                        27

<210> SEQ ID NO 8
<211> LENGTH: 33
<212> TYPE: DNA
```

```
<213> ORGANISM: Artificial Sequence
<220> FEATURE:
<223> OTHER INFORMATION: reverse primer for precursor frataxin cloning

<400> SEQUENCE: 8
acgctcgagt caagcatctt ttccggaata ggc                                33

<210> SEQ ID NO 9
<211> LENGTH: 30
<212> TYPE: DNA
<213> ORGANISM: Artificial Sequence
<220> FEATURE:
<223> OTHER INFORMATION: forward primer for MTS lad cloning

<400> SEQUENCE: 9
cgcggatcca cagagctgga gtcgtgtgta                                    30

<210> SEQ ID NO 10
<211> LENGTH: 66
<212> TYPE: DNA
<213> ORGANISM: Artificial Sequence
<220> FEATURE:
<223> OTHER INFORMATION: reverse primer for MTS lad cloning

<400> SEQUENCE: 10
cataggtggt ctcatctaga gagcctgggt ggcccaaagt tccagatgcg taagttctca   60
gaggca                                                              66

<210> SEQ ID NO 11
<211> LENGTH: 28
<212> TYPE: DNA
<213> ORGANISM: Artificial Sequence
<220> FEATURE:
<223> OTHER INFORMATION: forward primer for MTS orf cloning

<400> SEQUENCE: 11
cgcggatccg ggagcactag tgattcgc                                      28

<210> SEQ ID NO 12
<211> LENGTH: 66
<212> TYPE: DNA
<213> ORGANISM: Artificial Sequence
<220> FEATURE:
<223> OTHER INFORMATION: reverse primer for MTS orf cloning

<400> SEQUENCE: 12
cataggtggt ctcatctaga gagcctgggt ggcccaaagt tccagaagag gggtgtctgg   60
gagcga                                                              66

<210> SEQ ID NO 13
<211> LENGTH: 112
<212> TYPE: DNA
<213> ORGANISM: Artificial Sequence
<220> FEATURE:
<223> OTHER INFORMATION: forward oligo for MTS cs cloning

<400> SEQUENCE: 13
gatccggctt tacttactgc ggccgcccgg ctcttgggaa ccaagaatgc atcttgtctt   60
gttcttgcag cccggcatgc cagttctgga actttgggcc acccaggctc tc          112

<210> SEQ ID NO 14
<211> LENGTH: 112
<212> TYPE: DNA
<213> ORGANISM: Artificial Sequence
```

<220> FEATURE:
<223> OTHER INFORMATION: reverse primer for MTS cs cloning

<400> SEQUENCE: 14

```
tctagagagc ctgggtggcc caaagttcca gaactggcat gccgggctgc aagaacaaga    60
caagatgcat tcttggttcc caagagccgg gcggccgcag taagtaaagc cg           112
```

<210> SEQ ID NO 15
<211> LENGTH: 957
<212> TYPE: DNA
<213> ORGANISM: Homo sapiens

<400> SEQUENCE: 15

```
ctgaagggcc gtgaccttct cactctaaga aactttaccg agaagaaat taaatatatg    60
ctatggctat cagcagatct gaaatttagg ataaaacaga aaggagagta tttgccttta   120
ttgcaaggga agtccttagg catgattttt gagaaaagaa gtactcgaac aagattgtct   180
acagaaacag gctttgcact tctgggagga catccttgtt ttcttaccac acaagatatt   240
catttgggtg tgaatgaaag tctcacggac acggcccgtg tattgtctag catggcagat   300
gcagtattgg ctcgagtgta taacaatca gatttggaca ccctggctaa agaagcatcc   360
atcccaatta tcaatgggct gtcagatttg taccatccta tccagatcct ggctgattac   420
ctcacgctcc aggaacacta tagctctctg aaaggtctta ccctcagctg gatcggggat   480
gggaacaata tcctgcactc catcatgatg agcgcagcga aattcggaat gcaccttcag   540
gcagctactc caaagggtta tgagccggat gctagtgtaa ccaagttggc agagcagtat   600
gccaaagaga atggtaccaa gctgttgctg acaaatgatc cattggaagc agcgcatgga   660
ggcaatgtat taattacaga cacttggata agcatgggac aagaagagga gaagaaaaag   720
cggctccagg ctttccaagg ttaccaggtt acaatgaaga ctgctaaagt tgctgcctct   780
gactggacat ttttacactg cttgcccaga aagccagaag aagtggatga tgaagtcttt   840
tattctcctc gatcactagt gttcccagag gcagaaaaca gaaagtggac aatcatggct   900
gtcatggtgt ccctgctgac agattactca cctcagctcc agaagcctaa attttga     957
```

<210> SEQ ID NO 16
<211> LENGTH: 159
<212> TYPE: DNA
<213> ORGANISM: Homo sapiens

<400> SEQUENCE: 16

```
atgtaccgct acctggccaa agcgctgctg ccgtcccggg ccgggcccgc tgccctgggc    60
tccgcggcca accactcggc cgcgttgctg ggccggggcc gcggacagcc cgccgccgcc   120
tcgcagccgg ggctcgcatt ggccgcccgg cgccactac                         159
```

<210> SEQ ID NO 17
<211> LENGTH: 190
<212> TYPE: PRT
<213> ORGANISM: Artificial Sequence
<220> FEATURE:
<223> OTHER INFORMATION: His TAT MTS(cs) 81-210 FRA

<400> SEQUENCE: 17

```
Met Gly Ser Ser His His His His His His Ser Ser Gly Leu Val Pro
1               5                   10                  15
Arg Gly Ser His Met Arg Lys Lys Arg Arg Gln Arg Arg Arg Gly Ser
            20                  25                  30
```

Asp Pro Ala Leu Leu Thr Ala Ala Arg Leu Leu Gly Thr Lys Asn
                35                  40                  45

Ala Ser Cys Leu Val Leu Ala Ala Arg His Ala Ser Ser Gly Thr Leu
 50                  55                  60

Gly His Pro Gly Ser Leu Asp Glu Thr Thr Tyr Glu Arg Leu Ala Glu
 65                  70                  75                  80

Glu Thr Leu Asp Ser Leu Ala Glu Phe Phe Glu Asp Leu Ala Asp Lys
                 85                  90                  95

Pro Tyr Thr Phe Glu Asp Tyr Asp Val Ser Phe Gly Ser Gly Val Leu
            100                 105                 110

Thr Val Lys Leu Gly Gly Asp Leu Gly Thr Tyr Val Ile Asn Lys Gln
            115                 120                 125

Thr Pro Asn Lys Gln Ile Trp Leu Ser Ser Pro Ser Ser Gly Pro Lys
    130                 135                 140

Arg Tyr Asp Trp Thr Gly Lys Asn Trp Val Tyr Ser His Asp Gly Val
145                 150                 155                 160

Ser Leu His Glu Leu Leu Ala Ala Glu Leu Thr Lys Ala Leu Lys Thr
                165                 170                 175

Lys Leu Asp Leu Ser Ser Leu Ala Tyr Ser Gly Lys Asp Ala
            180                 185                 190

<210> SEQ ID NO 18
<211> LENGTH: 243
<212> TYPE: PRT
<213> ORGANISM: Artificial Sequence
<220> FEATURE:
<223> OTHER INFORMATION: HTFrataxin [His TAT MTS(fra)81-210 FRA]

<400> SEQUENCE: 18

Met Gly Ser Ser His His His His His His Ser Ser Gly Leu Val Pro
 1                   5                  10                  15

Arg Gly Ser His Met Arg Lys Lys Arg Arg Gln Arg Arg Arg Gly Ser
                20                  25                  30

Asp Pro Trp Thr Leu Gly Arg Arg Ala Val Ala Gly Leu Leu Ala Ser
                35                  40                  45

Pro Ser Pro Ala Gln Ala Gln Thr Leu Thr Arg Val Pro Arg Pro Ala
 50                  55                  60

Glu Leu Ala Pro Leu Cys Gly Arg Arg Gly Leu Arg Thr Asp Ile Asp
 65                  70                  75                  80

Ala Thr Cys Thr Pro Arg Arg Ala Ser Ser Asn Gln Arg Gly Leu Asn
                 85                  90                  95

Gln Ile Trp Asn Val Lys Lys Gln Ser Val Tyr Leu Met Asn Leu Arg
            100                 105                 110

Lys Ser Gly Thr Leu Gly His Pro Gly Ser Leu Asp Glu Thr Thr Tyr
            115                 120                 125

Glu Arg Leu Ala Glu Glu Thr Leu Asp Ser Leu Ala Glu Phe Phe Glu
    130                 135                 140

Asp Leu Ala Asp Lys Pro Tyr Thr Phe Glu Asp Tyr Asp Val Ser Phe
145                 150                 155                 160

Gly Ser Gly Val Leu Thr Val Lys Leu Gly Gly Asp Leu Gly Thr Tyr
                165                 170                 175

Val Ile Asn Lys Gln Thr Pro Asn Lys Gln Ile Trp Leu Ser Ser Pro
            180                 185                 190

Ser Ser Gly Pro Lys Arg Tyr Asp Trp Thr Gly Lys Asn Trp Val Tyr
            195                 200                 205

```
Ser His Asp Gly Val Ser Leu His Glu Leu Leu Ala Glu Leu Thr
    210                 215                 220

Lys Ala Leu Lys Thr Lys Leu Asp Leu Ser Ser Leu Ala Tyr Ser Gly
225                 230                 235                 240

Lys Asp Ala

<210> SEQ ID NO 19
<211> LENGTH: 199
<212> TYPE: PRT
<213> ORGANISM: Artificial Sequence
<220> FEATURE:
<223> OTHER INFORMATION: His TAT MTS(lad) 81-210 FRA

<400> SEQUENCE: 19

Met Gly Ser Ser His His His His His His Ser Ser Gly Leu Val Pro
1               5                   10                  15

Arg Gly Ser His Met Arg Lys Lys Arg Arg Gln Arg Arg Gly Ser
            20                  25                  30

Asp Pro Gln Ser Trp Ser Arg Val Tyr Cys Ser Leu Ala Lys Arg Gly
        35                  40                  45

His Phe Asn Arg Ile Ser His Gly Leu Gln Gly Leu Ser Ala Val Pro
    50                  55                  60

Leu Arg Thr Tyr Ala Ser Gly Thr Leu Gly His Pro Gly Ser Leu Asp
65                  70                  75                  80

Glu Thr Thr Tyr Glu Arg Leu Ala Glu Thr Leu Asp Ser Leu Ala
                85                  90                  95

Glu Phe Phe Glu Asp Leu Ala Asp Lys Pro Tyr Thr Phe Glu Asp Tyr
            100                 105                 110

Asp Val Ser Phe Gly Ser Gly Val Leu Thr Val Lys Leu Gly Gly Asp
        115                 120                 125

Leu Gly Thr Tyr Val Ile Asn Lys Gln Thr Pro Asn Lys Gln Ile Trp
    130                 135                 140

Leu Ser Ser Pro Ser Ser Gly Pro Lys Arg Tyr Asp Trp Thr Gly Lys
145                 150                 155                 160

Asn Trp Val Tyr Ser His Asp Gly Val Ser Leu His Glu Leu Ala
                165                 170                 175

Ala Glu Leu Thr Lys Ala Leu Lys Thr Lys Leu Asp Leu Ser Ser Leu
            180                 185                 190

Ala Tyr Ser Gly Lys Asp Ala
        195

<210> SEQ ID NO 20
<211> LENGTH: 198
<212> TYPE: PRT
<213> ORGANISM: Artificial Sequence
<220> FEATURE:
<223> OTHER INFORMATION: His TAT MTS(orf) 81-210 FRA

<400> SEQUENCE: 20

Met Gly Ser Ser His His His His His His Ser Ser Gly Leu Val Pro
1               5                   10                  15

Arg Gly Ser His Met Arg Lys Lys Arg Arg Gln Arg Arg Gly Ser
            20                  25                  30

Asp Pro Gly Ala Leu Val Ile Arg Gly Ile Arg Asn Phe Asn Leu Glu
        35                  40                  45

Asn Arg Ala Glu Arg Glu Ile Ser Lys Met Lys Pro Ser Val Ala Pro
    50                  55                  60
```

```
Arg His Pro Ser Ser Gly Thr Leu Gly His Pro Gly Ser Leu Asp Glu
 65                  70                  75                  80

Thr Thr Tyr Glu Arg Leu Ala Glu Glu Thr Leu Asp Ser Leu Ala Glu
                 85                  90                  95

Phe Phe Glu Asp Leu Ala Asp Lys Pro Tyr Thr Phe Glu Asp Tyr Asp
            100                 105                 110

Val Ser Phe Gly Ser Gly Val Leu Thr Val Lys Leu Gly Gly Asp Leu
        115                 120                 125

Gly Thr Tyr Val Ile Asn Lys Gln Thr Pro Asn Lys Gln Ile Trp Leu
130                 135                 140

Ser Ser Pro Ser Ser Gly Pro Lys Arg Tyr Asp Trp Thr Gly Lys Asn
145                 150                 155                 160

Trp Val Tyr Ser His Asp Gly Val Ser Leu His Glu Leu Leu Ala Ala
                165                 170                 175

Glu Leu Thr Lys Ala Leu Lys Thr Lys Leu Asp Leu Ser Ser Leu Ala
            180                 185                 190

Tyr Ser Gly Lys Asp Ala
        195
```

```
<210> SEQ ID NO 21
<211> LENGTH: 11
<212> TYPE: PRT
<213> ORGANISM: Human immunodeficiency virus type 1

<400> SEQUENCE: 21

Tyr Gly Arg Lys Lys Arg Arg Gln Arg Arg
1               5                   10

<210> SEQ ID NO 22
<211> LENGTH: 79
<212> TYPE: PRT
<213> ORGANISM: Homo sapiens

<400> SEQUENCE: 22

Trp Thr Leu Gly Arg Arg Ala Val Ala Gly Leu Leu Ala Ser Pro Ser
1               5                   10                  15

Pro Ala Gln Ala Gln Thr Leu Thr Arg Val Pro Arg Pro Ala Glu Leu
            20                  25                  30

Ala Pro Leu Cys Gly Arg Arg Gly Leu Arg Thr Asp Ile Asp Ala Thr
        35                  40                  45

Cys Thr Pro Arg Arg Ala Ser Ser Asn Gln Arg Gly Leu Asn Gln Ile
    50                  55                  60

Trp Asn Val Lys Lys Gln Ser Val Tyr Leu Met Asn Leu Arg Lys
65                  70                  75

<210> SEQ ID NO 23
<211> LENGTH: 26
<212> TYPE: PRT
<213> ORGANISM: Homo sapiens

<400> SEQUENCE: 23

Ala Leu Leu Thr Ala Ala Ala Arg Leu Leu Gly Thr Lys Asn Ala Ser
1               5                   10                  15

Cys Leu Val Leu Ala Ala Arg His Ala Ser
            20                  25

<210> SEQ ID NO 24
<211> LENGTH: 35
<212> TYPE: PRT
```

<213> ORGANISM: Homo sapiens

<400> SEQUENCE: 24

Gln Ser Trp Ser Arg Val Tyr Cys Ser Leu Ala Lys Arg Gly His Phe
1               5                   10                  15

Asn Arg Ile Ser His Gly Leu Gln Gly Leu Ser Ala Val Pro Leu Arg
            20                  25                  30

Thr Tyr Ala
        35

<210> SEQ ID NO 25
<211> LENGTH: 34
<212> TYPE: PRT
<213> ORGANISM: Homo sapiens

<400> SEQUENCE: 25

Gly Ala Leu Val Ile Arg Gly Ile Arg Asn Phe Asn Leu Glu Asn Arg
1               5                   10                  15

Ala Glu Arg Glu Ile Ser Lys Met Lys Pro Ser Val Ala Pro Arg His
            20                  25                  30

Pro Ser

<210> SEQ ID NO 26
<211> LENGTH: 130
<212> TYPE: PRT
<213> ORGANISM: Homo sapiens

<400> SEQUENCE: 26

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys
            100                 105                 110

Ala Leu Lys Thr Lys Leu Asp Leu Ser Ser Leu Ala Tyr Ser Gly Lys
        115                 120                 125

Asp Ala
    130

<210> SEQ ID NO 27
<211> LENGTH: 9
<212> TYPE: PRT
<213> ORGANISM: Human immunodeficiency virus type 2

<400> SEQUENCE: 27

Arg Lys Lys Arg Arg Gln Arg Arg Arg
1               5

<210> SEQ ID NO 28
<211> LENGTH: 170
<212> TYPE: PRT

<213> ORGANISM: Artificial Sequence
<220> FEATURE:
<223> OTHER INFORMATION: TAT MTS(cs) 81-210 FRA

<400> SEQUENCE: 28

```
Met Arg Lys Lys Arg Arg Gln Arg Arg Gly Ser Asp Pro Ala Leu
1               5                   10                  15

Leu Thr Ala Ala Ala Arg Leu Leu Gly Thr Lys Asn Ala Ser Cys Leu
            20                  25                  30

Val Leu Ala Ala Arg His Ala Ser Gly Thr Leu Gly His Pro Gly
        35                  40                  45

Ser Leu Asp Glu Thr Thr Tyr Glu Arg Leu Ala Glu Glu Thr Leu Asp
65          50                  55                  60

Ser Leu Ala Glu Phe Phe Glu Asp Leu Ala Asp Lys Pro Tyr Thr Phe
65              70                  75                  80

Glu Asp Tyr Asp Val Ser Phe Gly Ser Gly Val Leu Thr Val Lys Leu
                85                  90                  95

Gly Gly Asp Leu Gly Thr Tyr Val Ile Asn Lys Gln Thr Pro Asn Lys
            100                 105                 110

Gln Ile Trp Leu Ser Ser Pro Ser Gly Pro Lys Arg Tyr Asp Trp
        115                 120                 125

Thr Gly Lys Asn Trp Val Tyr Ser His Asp Gly Val Ser Leu His Glu
130                 135                 140

Leu Leu Ala Ala Glu Leu Thr Lys Ala Leu Lys Thr Lys Leu Asp Leu
145                 150                 155                 160

Ser Ser Leu Ala Tyr Ser Gly Lys Asp Ala
                165                 170
```

<210> SEQ ID NO 29
<211> LENGTH: 223
<212> TYPE: PRT
<213> ORGANISM: Artificial Sequence
<220> FEATURE:
<223> OTHER INFORMATION: TAT MTS(fra)81-210 FRA

<400> SEQUENCE: 29

```
Met Arg Lys Lys Arg Arg Gln Arg Arg Gly Ser Asp Pro Trp Thr
1               5                   10                  15

Leu Gly Arg Arg Ala Val Ala Gly Leu Leu Ala Ser Pro Ser Pro Ala
            20                  25                  30

Gln Ala Gln Thr Leu Thr Arg Val Pro Arg Pro Ala Glu Leu Ala Pro
        35                  40                  45

Leu Cys Gly Arg Arg Gly Leu Arg Thr Asp Ile Asp Ala Thr Cys Thr
    50                  55                  60

Pro Arg Arg Ala Ser Ser Asn Gln Arg Gly Leu Asn Gln Ile Trp Asn
65              70                  75                  80

Val Lys Lys Gln Ser Val Tyr Leu Met Asn Leu Arg Lys Ser Gly Thr
                85                  90                  95

Leu Gly His Pro Gly Ser Leu Asp Glu Thr Thr Tyr Glu Arg Leu Ala
            100                 105                 110

Glu Glu Thr Leu Asp Ser Leu Ala Glu Phe Phe Glu Asp Leu Ala Asp
        115                 120                 125

Lys Pro Tyr Thr Phe Glu Asp Tyr Asp Val Ser Phe Gly Ser Gly Val
    130                 135                 140

Leu Thr Val Lys Leu Gly Gly Asp Leu Gly Thr Tyr Val Ile Asn Lys
145                 150                 155                 160
```

```
Gln Thr Pro Asn Lys Gln Ile Trp Leu Ser Ser Pro Ser Ser Gly Pro
            165                 170                 175

Lys Arg Tyr Asp Trp Thr Gly Lys Asn Trp Val Tyr Ser His Asp Gly
        180                 185                 190

Val Ser Leu His Glu Leu Leu Ala Ala Glu Leu Thr Lys Ala Leu Lys
        195                 200                 205

Thr Lys Leu Asp Leu Ser Ser Leu Ala Tyr Ser Gly Lys Asp Ala
    210                 215                 220
```

<210> SEQ ID NO 30
<211> LENGTH: 179
<212> TYPE: PRT
<213> ORGANISM: Artificial Sequence
<220> FEATURE:
<223> OTHER INFORMATION: TAT MTS(lad) 81-210 FRA

<400> SEQUENCE: 30

```
Met Arg Lys Lys Arg Arg Gln Arg Arg Gly Ser Asp Pro Gln Ser
1               5                   10                  15

Trp Ser Arg Val Tyr Cys Ser Leu Ala Lys Arg Gly His Phe Asn Arg
            20                  25                  30

Ile Ser His Gly Leu Gln Gly Leu Ser Ala Val Pro Leu Arg Thr Tyr
        35                  40                  45

Ala Ser Gly Thr Leu Gly His Pro Gly Ser Leu Asp Glu Thr Thr Tyr
    50                  55                  60

Glu Arg Leu Ala Glu Glu Thr Leu Asp Ser Leu Ala Glu Phe Phe Glu
65                  70                  75                  80

Asp Leu Ala Asp Lys Pro Tyr Thr Phe Glu Asp Tyr Asp Val Ser Phe
                85                  90                  95

Gly Ser Gly Val Leu Thr Val Lys Leu Gly Gly Asp Leu Gly Thr Tyr
            100                 105                 110

Val Ile Asn Lys Gln Thr Pro Asn Lys Gln Ile Trp Leu Ser Ser Pro
        115                 120                 125

Ser Ser Gly Pro Lys Arg Tyr Asp Trp Thr Gly Lys Asn Trp Val Tyr
    130                 135                 140

Ser His Asp Gly Val Ser Leu His Glu Leu Leu Ala Ala Glu Leu Thr
145                 150                 155                 160

Lys Ala Leu Lys Thr Lys Leu Asp Leu Ser Ser Leu Ala Tyr Ser Gly
                165                 170                 175

Lys Asp Ala
```

<210> SEQ ID NO 31
<211> LENGTH: 178
<212> TYPE: PRT
<213> ORGANISM: Artificial Sequence
<220> FEATURE:
<223> OTHER INFORMATION: TAT MTS(orf) 81-210 FRA

<400> SEQUENCE: 31

```
Met Arg Lys Lys Arg Arg Gln Arg Arg Gly Ser Asp Pro Gly Ala
1               5                   10                  15

Leu Val Ile Arg Gly Ile Arg Asn Phe Asn Leu Glu Asn Arg Ala Glu
            20                  25                  30

Arg Glu Ile Ser Lys Met Lys Pro Ser Val Ala Pro Arg His Pro Ser
        35                  40                  45

Ser Gly Thr Leu Gly His Pro Gly Ser Leu Asp Glu Thr Thr Tyr Glu
    50                  55                  60
```

-continued

```
Arg Leu Ala Glu Glu Thr Leu Asp Ser Leu Ala Glu Phe Phe Glu Asp
 65                  70                  75                  80

Leu Ala Asp Lys Pro Tyr Thr Phe Glu Asp Tyr Asp Val Ser Phe Gly
                 85                  90                  95

Ser Gly Val Leu Thr Val Lys Leu Gly Gly Asp Leu Gly Thr Tyr Val
            100                 105                 110

Ile Asn Lys Gln Thr Pro Asn Lys Gln Ile Trp Leu Ser Ser Pro Ser
            115                 120                 125

Ser Gly Pro Lys Arg Tyr Asp Trp Thr Gly Lys Asn Trp Val Tyr Ser
        130                 135                 140

His Asp Gly Val Ser Leu His Glu Leu Leu Ala Ala Glu Leu Thr Lys
145                 150                 155                 160

Ala Leu Lys Thr Lys Leu Asp Leu Ser Ser Leu Ala Tyr Ser Gly Lys
                165                 170                 175

Asp Ala
```

<210> SEQ ID NO 32
<211> LENGTH: 4
<212> TYPE: PRT
<213> ORGANISM: Artificial Sequence
<220> FEATURE:
<223> OTHER INFORMATION: polypeptide linker

<400> SEQUENCE: 32

```
Gly Ser Asp Pro
  1
```

<210> SEQ ID NO 33
<211> LENGTH: 166
<212> TYPE: PRT
<213> ORGANISM: Artificial Sequence
<220> FEATURE:
<223> OTHER INFORMATION: TAT MTS(cs) 81-210 FRA delta linker

<400> SEQUENCE: 33

```
Met Arg Lys Lys Arg Arg Gln Arg Arg Arg Ala Leu Leu Thr Ala Ala
  1               5                  10                  15

Ala Arg Leu Leu Gly Thr Lys Asn Ala Ser Cys Leu Val Leu Ala Ala
                 20                  25                  30

Arg His Ala Ser Ser Gly Thr Leu Gly His Pro Gly Ser Leu Asp Glu
             35                  40                  45

Thr Thr Tyr Glu Arg Leu Ala Glu Glu Thr Leu Asp Ser Leu Ala Glu
         50                  55                  60

Phe Phe Glu Asp Leu Ala Asp Lys Pro Tyr Thr Phe Glu Asp Tyr Asp
 65                  70                  75                  80

Val Ser Phe Gly Ser Gly Val Leu Thr Val Lys Leu Gly Gly Asp Leu
                 85                  90                  95

Gly Thr Tyr Val Ile Asn Lys Gln Thr Pro Asn Lys Gln Ile Trp Leu
            100                 105                 110

Ser Ser Pro Ser Ser Gly Pro Lys Arg Tyr Asp Trp Thr Gly Lys Asn
            115                 120                 125

Trp Val Tyr Ser His Asp Gly Val Ser Leu His Glu Leu Leu Ala Ala
        130                 135                 140

Glu Leu Thr Lys Ala Leu Lys Thr Lys Leu Asp Leu Ser Ser Leu Ala
145                 150                 155                 160

Tyr Ser Gly Lys Asp Ala
                165
```

<210> SEQ ID NO 34
<211> LENGTH: 219
<212> TYPE: PRT
<213> ORGANISM: Artificial Sequence
<220> FEATURE:
<223> OTHER INFORMATION: TAT MTS(fra)81-210 FRA delta linker

<400> SEQUENCE: 34

```
Met Arg Lys Lys Arg Arg Gln Arg Arg Trp Thr Leu Gly Arg Arg
1               5                   10                  15

Ala Val Ala Gly Leu Leu Ala Ser Pro Ser Pro Ala Gln Ala Gln Thr
                20                  25                  30

Leu Thr Arg Val Pro Arg Pro Ala Glu Leu Ala Pro Leu Cys Gly Arg
            35                  40                  45

Arg Gly Leu Arg Thr Asp Ile Asp Ala Thr Cys Thr Pro Arg Arg Ala
        50                  55                  60

Ser Ser Asn Gln Arg Gly Leu Asn Gln Ile Trp Asn Val Lys Lys Gln
65                  70                  75                  80

Ser Val Tyr Leu Met Asn Leu Arg Lys Ser Gly Thr Leu Gly His Pro
                85                  90                  95

Gly Ser Leu Asp Glu Thr Thr Tyr Glu Arg Leu Ala Glu Glu Thr Leu
                100                 105                 110

Asp Ser Leu Ala Glu Phe Phe Glu Asp Leu Ala Asp Lys Pro Tyr Thr
            115                 120                 125

Phe Glu Asp Tyr Asp Val Ser Phe Gly Ser Gly Val Leu Thr Val Lys
        130                 135                 140

Leu Gly Gly Asp Leu Gly Thr Tyr Val Ile Asn Lys Gln Thr Pro Asn
145                 150                 155                 160

Lys Gln Ile Trp Leu Ser Ser Pro Ser Ser Gly Pro Lys Arg Tyr Asp
                165                 170                 175

Trp Thr Gly Lys Asn Trp Val Tyr Ser His Asp Gly Val Ser Leu His
            180                 185                 190

Glu Leu Leu Ala Ala Glu Leu Thr Lys Ala Leu Lys Thr Lys Leu Asp
        195                 200                 205

Leu Ser Ser Leu Ala Tyr Ser Gly Lys Asp Ala
    210                 215
```

<210> SEQ ID NO 35
<211> LENGTH: 175
<212> TYPE: PRT
<213> ORGANISM: Artificial Sequence
<220> FEATURE:
<223> OTHER INFORMATION: TAT MTS(lad) 81-210 FRA delta linker

<400> SEQUENCE: 35

```
Met Arg Lys Lys Arg Arg Gln Arg Arg Gln Ser Trp Ser Arg Val
1               5                   10                  15

Tyr Cys Ser Leu Ala Lys Arg Gly His Phe Asn Arg Ile Ser His Gly
                20                  25                  30

Leu Gln Gly Leu Ser Ala Val Pro Leu Arg Thr Tyr Ala Ser Gly Thr
            35                  40                  45

Leu Gly His Pro Gly Ser Leu Asp Glu Thr Thr Tyr Glu Arg Leu Ala
        50                  55                  60

Glu Glu Thr Leu Asp Ser Leu Ala Glu Phe Phe Glu Asp Leu Ala Asp
65                  70                  75                  80

Lys Pro Tyr Thr Phe Glu Asp Tyr Asp Val Ser Phe Gly Ser Gly Val
                85                  90                  95
```

```
Leu Thr Val Lys Leu Gly Gly Asp Leu Gly Thr Tyr Val Ile Asn Lys
            100                 105                 110

Gln Thr Pro Asn Lys Gln Ile Trp Leu Ser Ser Pro Ser Gly Pro
        115                 120                 125

Lys Arg Tyr Asp Trp Thr Gly Lys Asn Trp Val Tyr Ser His Asp Gly
130                 135                 140

Val Ser Leu His Glu Leu Leu Ala Ala Glu Leu Thr Lys Ala Leu Lys
145                 150                 155                 160

Thr Lys Leu Asp Leu Ser Ser Leu Ala Tyr Ser Gly Lys Asp Ala
                165                 170                 175
```

```
<210> SEQ ID NO 36
<211> LENGTH: 174
<212> TYPE: PRT
<213> ORGANISM: Artificial Sequence
<220> FEATURE:
<223> OTHER INFORMATION: TAT MTS(orf) 81-210 FRA delta linker

<400> SEQUENCE: 36
```

```
Met Arg Lys Lys Arg Arg Gln Arg Arg Gly Ala Leu Val Ile Arg
1               5                   10                  15

Gly Ile Arg Asn Phe Asn Leu Glu Asn Arg Ala Glu Arg Glu Ile Ser
                20                  25                  30

Lys Met Lys Pro Ser Val Ala Pro Arg His Pro Ser Ser Gly Thr Leu
            35                  40                  45

Gly His Pro Gly Ser Leu Asp Glu Thr Thr Tyr Glu Arg Leu Ala Glu
        50                  55                  60

Glu Thr Leu Asp Ser Leu Ala Glu Phe Phe Glu Asp Leu Ala Asp Lys
65                  70                  75                  80

Pro Tyr Thr Phe Glu Asp Tyr Asp Val Ser Phe Gly Ser Gly Val Leu
                85                  90                  95

Thr Val Lys Leu Gly Gly Asp Leu Gly Thr Tyr Val Ile Asn Lys Gln
            100                 105                 110

Thr Pro Asn Lys Gln Ile Trp Leu Ser Ser Pro Ser Ser Gly Pro Lys
        115                 120                 125

Arg Tyr Asp Trp Thr Gly Lys Asn Trp Val Tyr Ser His Asp Gly Val
    130                 135                 140

Ser Leu His Glu Leu Leu Ala Ala Glu Leu Thr Lys Ala Leu Lys Thr
145                 150                 155                 160

Lys Leu Asp Leu Ser Ser Leu Ala Tyr Ser Gly Lys Asp Ala
                165                 170
```

```
<210> SEQ ID NO 37
<211> LENGTH: 105
<212> TYPE: DNA
<213> ORGANISM: Homo sapiens

<400> SEQUENCE: 37
ctgtttaacc tgcgcattct gctgaacaat gcggccttcc gtaacggcca taattttatg      60
gtccgcaact tccgttgcgg tcagccgctg caaaataaag tgcag                    105
```

```
<210> SEQ ID NO 38
<211> LENGTH: 35
<212> TYPE: PRT
<213> ORGANISM: Homo sapiens

<400> SEQUENCE: 38
```

```
Leu Phe Asn Leu Arg Ile Leu Leu Asn Asn Ala Ala Phe Arg Asn Gly
1               5                   10                  15

His Asn Phe Met Val Arg Asn Phe Arg Cys Gly Gln Pro Leu Gln Asn
            20                  25                  30

Lys Val Gln
        35

<210> SEQ ID NO 39
<211> LENGTH: 318
<212> TYPE: PRT
<213> ORGANISM: Homo sapiens

<400> SEQUENCE: 39

Leu Lys Gly Arg Asp Leu Leu Thr Leu Arg Asn Phe Thr Gly Glu Glu
1               5                   10                  15

Ile Lys Tyr Met Leu Trp Leu Ser Ala Asp Leu Lys Phe Arg Ile Lys
            20                  25                  30

Gln Lys Gly Glu Tyr Leu Pro Leu Leu Gln Gly Lys Ser Leu Gly Met
            35                  40                  45

Ile Phe Glu Lys Arg Ser Thr Arg Thr Arg Leu Ser Thr Glu Thr Gly
50                  55                  60

Phe Ala Leu Leu Gly Gly His Pro Cys Phe Leu Thr Thr Gln Asp Ile
65                  70                  75                  80

His Leu Gly Val Asn Glu Ser Leu Thr Asp Thr Ala Arg Val Leu Ser
                85                  90                  95

Ser Met Ala Asp Ala Val Leu Ala Arg Val Tyr Lys Gln Ser Asp Leu
            100                 105                 110

Asp Thr Leu Ala Lys Glu Ala Ser Ile Pro Ile Ile Asn Gly Leu Ser
        115                 120                 125

Asp Leu Tyr His Pro Ile Gln Ile Leu Ala Asp Tyr Leu Thr Leu Gln
    130                 135                 140

Glu His Tyr Ser Ser Leu Lys Gly Leu Thr Leu Ser Trp Ile Gly Asp
145                 150                 155                 160

Gly Asn Asn Ile Leu His Ser Ile Met Met Ser Ala Ala Lys Phe Gly
                165                 170                 175

Met His Leu Gln Ala Ala Thr Pro Lys Gly Tyr Glu Pro Asp Ala Ser
            180                 185                 190

Val Thr Lys Leu Ala Glu Gln Tyr Ala Lys Glu Asn Gly Thr Lys Leu
        195                 200                 205

Leu Leu Thr Asn Asp Pro Leu Glu Ala Ala His Gly Gly Asn Val Leu
    210                 215                 220

Ile Thr Asp Thr Trp Ile Ser Met Gly Gln Glu Glu Lys Lys Lys
225                 230                 235                 240

Arg Leu Gln Ala Phe Gln Gly Tyr Gln Val Thr Met Lys Thr Ala Lys
                245                 250                 255

Val Ala Ala Ser Asp Trp Thr Phe Leu His Cys Leu Pro Arg Lys Pro
            260                 265                 270

Glu Glu Val Asp Asp Glu Val Phe Tyr Ser Pro Arg Ser Leu Val Phe
        275                 280                 285

Pro Glu Ala Glu Asn Arg Lys Trp Thr Ile Met Ala Val Met Val Ser
    290                 295                 300

Leu Leu Thr Asp Tyr Ser Pro Gln Leu Gln Lys Pro Lys Phe
305                 310                 315

<210> SEQ ID NO 40
```

<211> LENGTH: 1170
<212> TYPE: DNA
<213> ORGANISM: Artificial Sequence
<220> FEATURE:
<223> OTHER INFORMATION: His-TAT-MTS(otc)-OTC delta inker

<400> SEQUENCE: 40

| | | |
|---|---|---|
| catatgggct catcgcatca tcatcatcat cactcatcag gtctggttcc gcgtggctcg | 60 |
| cacatgtatg gtcgcaaaaa acgtcgtcaa cgtcgccgtc tgtttaacct gcgcattctg | 120 |
| ctgaacaatg cggccttccg taacggccat aattttatgg tccgcaactt ccgttgcggt | 180 |
| cagccgctgc aaaataaagt gcagctgaaa ggccgcgatc tgctgaccct gcgtaacttc | 240 |
| acgggtgaag aaatcaaata catgctgtgg ctgagcgcag acctgaaatt ccgcatcaaa | 300 |
| caaaaaggcg aatacctgcc gctgctgcag ggcaaatctc tgggtatgat ttttgaaaaa | 360 |
| cgtagtaccc gcacgcgtct gtccaccgaa acgggctttg ccctgctggg cggtcatccg | 420 |
| tgtttcctga ccacgcaaga tatccacctg ggtgtgaacg aaagtctgac cgatacggca | 480 |
| cgcgttctga gctctatggc agacgctgtg ctggctcgtg tttataaaca gtccgatctg | 540 |
| gacaccctgg cgaaagaagc ctcaattccg attatcaatg gcctgtcgga tctgtaccat | 600 |
| ccgattcaaa tcctggcgga ctatctgacc ctgcaggaac actacagttc cctgaaaggt | 660 |
| ctgaccctga gttggatcgg cgatggtaac aatattctgc atagcatcat gatgtctgca | 720 |
| gctaaatttg gcatgcacct gcaagcggcc accccgaaag gttatgaacc ggatgccagc | 780 |
| gttacgaaac tggcagaaca gtacgctaaa gaaaacggta ccaaactgct gctgacgaat | 840 |
| gatccgctgg aagcagctca tggcggtaac gtcctgatta ccgacacgtg gatctctatg | 900 |
| ggccaggaag aagaaaagaa aaaacgtctg caggcgtttc aaggttatca ggttaccatg | 960 |
| aaaacggcca agtcgcggc cagcgattgg accttcctgc actgcctgcc gcgtaaaccg | 1020 |
| gaagaagtcg atgacgaagt gttttactca ccgcgctcgc tggtgttccc ggaagcagaa | 1080 |
| aatcgtaaat ggaccatcat ggctgttatg gtgtccctgc tgaccgacta ttccccgcaa | 1140 |
| ctgcaaaaac cgaaattcta atgaaagctt | 1170 |

<210> SEQ ID NO 41
<211> LENGTH: 1155
<212> TYPE: DNA
<213> ORGANISM: Artificial Sequence
<220> FEATURE:
<223> OTHER INFORMATION: His-TAT-MTS(cs)-OTC

<400> SEQUENCE: 41

| | | |
|---|---|---|
| catatgggct catctcatca tcatcatcat cattcgtcag gtctggtccc gcgtggctct | 60 |
| cacatgcgta aaaacgtcg tcagcgtcgt cgtggcagtg atccggcact gctgaccgca | 120 |
| gcagcacgtc tgctgggtac gaaaaacgct agctgcctgg tgctggctgc gcgtcatgcg | 180 |
| tctgaatttc tgaaaggccg tgatctgctg accctgcgca acttcacggg tgaagaaatc | 240 |
| aaatacatgc tgtggctgag tgccgacctg aaatttcgta tcaaacaaaa aggcgaatac | 300 |
| ctgccgctgc tgcagggcaa atccctgggt atgatttcg aaaaacgcag tacccgtacg | 360 |
| cgcctgtcca ccgaaacggg cttgcactg ctggcggtc atccgtgttt cctgaccacg | 420 |
| caagatatcc acctgggtgt gaacgaatca ctgaccgata cggctcgtgt tctgagctct | 480 |
| atggcagacg cagtgctggc acgtgtttat aaacagtcgg atctggacac cctggctaaa | 540 |
| gaagcgtcaa ttccgattat caatggcctg tcggatctgt accatccgat tcaaatcctg | 600 |
| gcggactatc tgaccctgca ggaacactac agttccctga aggtctgac cctgagctgg | 660 |

```
atcggcgatg gtaacaatat tctgcatagc atcatgatgt ctgccgcaaa atttggcatg      720
cacctgcaag ctgcgacccc gaaaggttat gaaccggacg ccagcgtcac gaaactggcc      780
gaacagtacg caaagaaaaa cggtaccaaa ctgctgctga cgaatgatcc gctggaagcc      840
gcacatggcg gtaacgttct gattaccgac acgtggatca gcatgggcca ggaagaagaa      900
aagaaaaaac gtctgcaggc ctttcaaggt tatcaggtta ccatgaaaac ggcaaaagtc      960
gctgcgtctg attggacctt cctgcactgc ctgccgcgca aaccggaaga agtcgatgac     1020
gaagtgtttt actcaccgcg ttcgctggtt ttcccggaag cggaaaatcg caaatggacc     1080
attatggctg tgatggtctc tctgctgacg gactactcgc cgcaactgca aaaaccgaaa     1140
ttctaatgaa agctt                                                      1155

<210> SEQ ID NO 42
<211> LENGTH: 1179
<212> TYPE: DNA
<213> ORGANISM: Artificial Sequence
<220> FEATURE:
<223> OTHER INFORMATION: His-TAT-MTS(orf)-OTC

<400> SEQUENCE: 42
catatgggtt catcacatca tcatcatcat cattcatcag gtctggtccc gcgtggttca       60
cacatgcgta aaaaacgtcg tcagcgtcgt cgtggcagtg atccgggtgc gctggtcatt      120
cgtggcatcc gcaactttaa tctggaaaac cgtgcggaac gcgaaattag taaaatgaaa      180
ccgtccgtgg caccgcgtca tccgtctgaa tttctgaaag ccgtgatctg ctgaccctg      240 cgcaacttca cgggtgaaga aatcaaatac atgctgtggc tgagtgcaga cctgaaattc      300
cgtatcaaac aaaagggtga atacctgccg ctgctgcagg gcaaatccct gggtatgatt      360
ttcgaaaaac gctcaacccg tacgcgcctg tcgaccgaaa cgggctttgc cctgctgggc      420
ggtcatccgt gcttcctgac cacgcaagat atccacctgg gtgtgaacga atcactgacc      480
gatacggcac gtgttctgag ctctatggca gacgcagtgc tggctcgtgt ttataaacag      540
tcggatctgg acaccctggc aaaagaagct agcattccga ttatcaatgg cctgtctgat      600
ctgtaccatc cgattcaaat cctggcggac tatctgaccc tgcaggaaca ctacagttcc      660
ctgaaaggtc tgaccctgag ctggatcggc gatggtaaca atattctgca tagcatcatg      720
atgtctgcgc caaattcgg catgcacctg caagcagcta ccccgaaagg ttatgaaccg      780
gacgcctccg ttacgaaact ggcggaacag tacgccaaag aaaacggcac caaactgctg      840
ctgacgaatg atccgctgga gcggcccat ggcggtaacg tcctgattac cgacacgtgg      900
atcagcatgg gccaggaaga agaaaagaaa aacgtctgc aggcatttca aggttatcag      960
gttaccatga aaacggctaa agtcgcagct tctgattgga ccttcctgca ctgtctgccg     1020
cgcaaaccgg aagaagtcga tgacgaagtg ttttactcac cgcgttcgct ggtgttcccg     1080
gaagcggaaa atcgcaaatg gaccattatg gctgtgatgg tgtcgctgct gacggactac     1140
tcgccgcaac tgcaaaaacc gaaattctaa tgaaagctt                            1179

<210> SEQ ID NO 43
<211> LENGTH: 1182
<212> TYPE: DNA
<213> ORGANISM: Artificial Sequence
<220> FEATURE:
<223> OTHER INFORMATION: His-TAT-MTS(lad)-OTC

<400> SEQUENCE: 43
```

-continued

```
catatgggta gttcacatca tcatcatcat cactcgtcgg gtctggtgcc gcgtggctca    60
cacatgcgta aaaaacgtcg tcagcgtcgt cgtggctcag atccgcaatc atggtcgcgc   120
gtctattgct cgctggcgaa acgtggtcat tttaaccgca ttagccacgg cctgcagggt   180
ctgtctgcag tgccgctgcg tacctacgct gaatttctga aaggccgtga tctgctgacc   240
ctgcgcaact tcacgggtga agaaatcaaa tacatgctgt ggctgagcgc agacctgaaa   300
tttcgtatca acaaaaagg cgaatacctg ccgctgctgc agggcaaatc tctgggtatg   360
attttcgaaa aacgctcaac ccgtacgcgc ctgtcgaccg aaacgggctt tgccctgctg   420
ggcggtcatc cgtgtttcct gaccacgcag gatatccacc tgggtgtgaa cgaaagtctg   480
accgatacgg cacgtgttct gagctctatg gcagacgcag tgctggctcg tgtttataaa   540
cagtccgatc tggacaccct ggcaaaagaa gctagtattc cgattatcaa tggcctgtcc   600
gatctgtacc atccgattca atcctggcg gactatctga ccctgcagga acactacagt   660
tccctgaaag gtctgacgct gagctggatc ggcgatggta acaatattct gcatagtatc   720
atgatgtccg cggccaaatt cggcatgcac ctgcaagcag ctaccccgaa aggttatgaa   780
ccggacgcct ctgttacgaa actggcggaa cagtacgcca agaaaacgg taccaaactg   840
ctgctgacga atgatccgct ggaagcggcc catggcggta acgtcctgat taccgacacg   900
tggatcagta tgggccagga agaagaaaag aaaaaacgtc tgcaggcgtt tcaaggttat   960
caggttacca tgaaaacggc caaagtcgca gctagcgatt ggaccttcct gcactgcctg  1020
ccgcgcaaac cggaagaagt cgatgacgaa gtgttttata gccgcgttc tctggtgttc  1080
ccggaagcgg aaaatcgcaa atggaccatc atggccgtta tggtgtcgct gctgaccgat  1140
tactccccgc aactgcaaaa accgaaattc taatgaaagc tt                     1182
```

<210> SEQ ID NO 44
<211> LENGTH: 385
<212> TYPE: PRT
<213> ORGANISM: Artificial Sequence
<220> FEATURE:
<223> OTHER INFORMATION: His-TAT-MTS(otc)-OTC delta linker

<400> SEQUENCE: 44

```
Met Gly Ser Ser His His His His His His Ser Ser Gly Leu Val Pro
1               5                   10                  15

Arg Gly Ser His Met Tyr Gly Arg Lys Lys Arg Gln Arg Arg
            20                  25                  30

Leu Phe Asn Leu Arg Ile Leu Leu Asn Asn Ala Ala Phe Arg Asn Gly
        35                  40                  45

His Asn Phe Met Val Arg Asn Phe Arg Cys Gly Gln Pro Leu Gln Asn
    50                  55                  60

Lys Val Gln Leu Lys Gly Arg Asp Leu Leu Thr Leu Arg Asn Phe Thr
65                  70                  75                  80

Gly Glu Glu Ile Lys Tyr Met Leu Trp Leu Ser Ala Asp Leu Lys Phe
                85                  90                  95

Arg Ile Lys Gln Lys Gly Glu Tyr Leu Pro Leu Leu Gln Gly Lys Ser
            100                 105                 110

Leu Gly Met Ile Phe Glu Lys Arg Ser Thr Arg Thr Arg Leu Ser Thr
        115                 120                 125

Glu Thr Gly Phe Ala Leu Leu Gly Gly His Pro Cys Phe Leu Thr Thr
    130                 135                 140

Gln Asp Ile His Leu Gly Val Asn Glu Ser Leu Thr Asp Thr Ala Arg
145                 150                 155                 160
```

```
Val Leu Ser Ser Met Ala Asp Ala Val Leu Ala Arg Val Tyr Lys Gln
            165                 170                 175

Ser Asp Leu Asp Thr Leu Ala Lys Glu Ala Ser Ile Pro Ile Ile Asn
        180                 185                 190

Gly Leu Ser Asp Leu Tyr His Pro Ile Gln Ile Leu Ala Asp Tyr Leu
            195                 200                 205

Thr Leu Gln Glu His Tyr Ser Ser Leu Lys Gly Leu Thr Leu Ser Trp
        210                 215                 220

Ile Gly Asp Gly Asn Asn Ile Leu His Ser Ile Met Met Ser Ala Ala
225                 230                 235                 240

Lys Phe Gly Met His Leu Gln Ala Ala Thr Pro Lys Gly Tyr Glu Pro
            245                 250                 255

Asp Ala Ser Val Thr Lys Leu Ala Glu Gln Tyr Ala Lys Glu Asn Gly
        260                 265                 270

Thr Lys Leu Leu Leu Thr Asn Asp Pro Leu Glu Ala Ala His Gly Gly
            275                 280                 285

Asn Val Leu Ile Thr Asp Thr Trp Ile Ser Met Gly Gln Glu Glu Glu
        290                 295                 300

Lys Lys Lys Arg Leu Gln Ala Phe Gln Gly Tyr Gln Val Thr Met Lys
305                 310                 315                 320

Thr Ala Lys Val Ala Ala Ser Asp Trp Thr Phe Leu His Cys Leu Pro
            325                 330                 335

Arg Lys Pro Glu Glu Val Asp Asp Glu Val Phe Tyr Ser Pro Arg Ser
        340                 345                 350

Leu Val Phe Pro Glu Ala Glu Asn Arg Lys Trp Thr Ile Met Ala Val
            355                 360                 365

Met Val Ser Leu Leu Thr Asp Tyr Ser Pro Gln Leu Gln Lys Pro Lys
        370                 375                 380

Phe
385

<210> SEQ ID NO 45
<211> LENGTH: 380
<212> TYPE: PRT
<213> ORGANISM: Artificial Sequence
<220> FEATURE:
<223> OTHER INFORMATION: His-TAT-MTS(cs)-OTC

<400> SEQUENCE: 45

Met Gly Ser Ser His His His His His His Ser Ser Gly Leu Val Pro
1               5                   10                  15

Arg Gly Ser His Met Arg Lys Lys Arg Arg Gln Arg Arg Arg Gly Ser
            20                  25                  30

Asp Pro Ala Leu Leu Thr Ala Ala Arg Leu Leu Gly Thr Lys Asn
        35                  40                  45

Ala Ser Cys Leu Val Leu Ala Ala Arg His Ala Ser Glu Phe Leu Lys
        50                  55                  60

Gly Arg Asp Leu Leu Thr Leu Arg Asn Phe Thr Gly Glu Glu Ile Lys
65                  70                  75                  80

Tyr Met Leu Trp Leu Ser Ala Asp Leu Lys Phe Arg Ile Lys Gln Lys
            85                  90                  95

Gly Glu Tyr Leu Pro Leu Leu Gln Gly Lys Ser Leu Gly Met Ile Phe
        100                 105                 110

Glu Lys Arg Ser Thr Arg Thr Arg Leu Ser Thr Glu Thr Gly Phe Ala
            115                 120                 125
```

```
Leu Leu Gly Gly His Pro Cys Phe Leu Thr Thr Gln Asp Ile His Leu
    130                 135                 140

Gly Val Asn Glu Ser Leu Thr Asp Thr Ala Arg Val Leu Ser Ser Met
145                 150                 155                 160

Ala Asp Ala Val Leu Ala Arg Val Tyr Lys Gln Ser Asp Leu Asp Thr
                165                 170                 175

Leu Ala Lys Glu Ala Ser Ile Pro Ile Ile Asn Gly Leu Ser Asp Leu
            180                 185                 190

Tyr His Pro Ile Gln Ile Leu Ala Asp Tyr Leu Thr Leu Gln Glu His
        195                 200                 205

Tyr Ser Ser Leu Lys Gly Leu Thr Leu Ser Trp Ile Gly Asp Gly Asn
    210                 215                 220

Asn Ile Leu His Ser Ile Met Met Ser Ala Ala Lys Phe Gly Met His
225                 230                 235                 240

Leu Gln Ala Ala Thr Pro Lys Gly Tyr Glu Pro Asp Ala Ser Val Thr
                245                 250                 255

Lys Leu Ala Glu Gln Tyr Ala Lys Glu Asn Gly Thr Lys Leu Leu Leu
            260                 265                 270

Thr Asn Asp Pro Leu Glu Ala Ala His Gly Gly Asn Val Leu Ile Thr
        275                 280                 285

Asp Thr Trp Ile Ser Met Gly Gln Glu Glu Lys Lys Lys Arg Leu
    290                 295                 300

Gln Ala Phe Gln Gly Tyr Gln Val Thr Met Lys Thr Ala Lys Val Ala
305                 310                 315                 320

Ala Ser Asp Trp Thr Phe Leu His Cys Leu Pro Arg Lys Pro Glu Glu
                325                 330                 335

Val Asp Asp Glu Val Phe Tyr Ser Pro Arg Ser Leu Val Phe Pro Glu
            340                 345                 350

Ala Glu Asn Arg Lys Trp Thr Ile Met Ala Val Met Val Ser Leu Leu
        355                 360                 365

Thr Asp Tyr Ser Pro Gln Leu Gln Lys Pro Lys Phe
    370                 375                 380

<210> SEQ ID NO 46
<211> LENGTH: 388
<212> TYPE: PRT
<213> ORGANISM: Artificial Sequence
<220> FEATURE:
<223> OTHER INFORMATION: His-TAT-MTS(orf)-OTC

<400> SEQUENCE: 46

Met Gly Ser Ser His His His His His His Ser Ser Gly Leu Val Pro
1               5                   10                  15

Arg Gly Ser His Met Arg Lys Lys Arg Arg Gln Arg Arg Arg Gly Ser
                20                  25                  30

Asp Pro Gly Ala Leu Val Ile Arg Gly Ile Arg Asn Phe Asn Leu Glu
            35                  40                  45

Asn Arg Ala Glu Arg Glu Ile Ser Lys Met Lys Pro Ser Val Ala Pro
        50                  55                  60

Arg His Pro Ser Glu Phe Leu Lys Gly Arg Asp Leu Leu Thr Leu Arg
65                  70                  75                  80

Asn Phe Thr Gly Glu Glu Ile Lys Tyr Met Leu Trp Leu Ser Ala Asp
                85                  90                  95

Leu Lys Phe Arg Ile Lys Gln Lys Gly Glu Tyr Leu Pro Leu Leu Gln
            100                 105                 110
```

```
Gly Lys Ser Leu Gly Met Ile Phe Glu Lys Arg Ser Thr Arg Thr Arg
            115                 120                 125
Leu Ser Thr Glu Thr Gly Phe Ala Leu Leu Gly Gly His Pro Cys Phe
            130                 135                 140
Leu Thr Thr Gln Asp Ile His Leu Gly Val Asn Glu Ser Leu Thr Asp
145                 150                 155                 160
Thr Ala Arg Val Leu Ser Ser Met Ala Asp Ala Val Leu Ala Arg Val
                165                 170                 175
Tyr Lys Gln Ser Asp Leu Asp Thr Leu Ala Lys Glu Ala Ser Ile Pro
            180                 185                 190
Ile Ile Asn Gly Leu Ser Asp Leu Tyr His Pro Ile Gln Ile Leu Ala
            195                 200                 205
Asp Tyr Leu Thr Leu Gln Glu His Tyr Ser Ser Leu Lys Gly Leu Thr
            210                 215                 220
Leu Ser Trp Ile Gly Asp Gly Asn Asn Ile Leu His Ser Ile Met Met
225                 230                 235                 240
Ser Ala Ala Lys Phe Gly Met His Leu Gln Ala Ala Thr Pro Lys Gly
                245                 250                 255
Tyr Glu Pro Asp Ala Ser Val Thr Lys Leu Ala Glu Gln Tyr Ala Lys
            260                 265                 270
Glu Asn Gly Thr Lys Leu Leu Leu Thr Asn Asp Pro Leu Glu Ala Ala
            275                 280                 285
His Gly Gly Asn Val Leu Ile Thr Asp Thr Trp Ile Ser Met Gly Gln
            290                 295                 300
Glu Glu Glu Lys Lys Lys Arg Leu Gln Ala Phe Gln Gly Tyr Gln Val
305                 310                 315                 320
Thr Met Lys Thr Ala Lys Val Ala Ala Ser Asp Trp Thr Phe Leu His
                325                 330                 335
Cys Leu Pro Arg Lys Pro Glu Glu Val Asp Asp Glu Val Phe Tyr Ser
            340                 345                 350
Pro Arg Ser Leu Val Phe Pro Glu Ala Glu Asn Arg Lys Trp Thr Ile
            355                 360                 365
Met Ala Val Met Val Ser Leu Leu Thr Asp Tyr Ser Pro Gln Leu Gln
            370                 375                 380
Lys Pro Lys Phe
385

<210> SEQ ID NO 47
<211> LENGTH: 389
<212> TYPE: PRT
<213> ORGANISM: Artificial Sequence
<220> FEATURE:
<223> OTHER INFORMATION: His-TAT-MTS(lad)-OTC

<400> SEQUENCE: 47

Met Gly Ser Ser His His His His His His Ser Ser Gly Leu Val Pro
1               5                   10                  15
Arg Gly Ser His Met Arg Lys Lys Arg Arg Gln Arg Arg Gly Ser
            20                  25                  30
Asp Pro Gln Ser Trp Ser Arg Val Tyr Cys Ser Leu Ala Lys Arg Gly
            35                  40                  45
His Phe Asn Arg Ile Ser His Gly Leu Gln Gly Leu Ser Ala Val Pro
            50                  55                  60
Leu Arg Thr Tyr Ala Glu Phe Leu Lys Gly Arg Asp Leu Leu Thr Leu
65                  70                  75                  80
```

```
Arg Asn Phe Thr Gly Glu Glu Ile Lys Tyr Met Leu Trp Leu Ser Ala
                85                  90                  95

Asp Leu Lys Phe Arg Ile Lys Gln Lys Gly Glu Tyr Leu Pro Leu Leu
            100                 105                 110

Gln Gly Lys Ser Leu Gly Met Ile Phe Glu Lys Arg Ser Thr Arg Thr
        115                 120                 125

Arg Leu Ser Thr Glu Thr Gly Phe Ala Leu Leu Gly Gly His Pro Cys
    130                 135                 140

Phe Leu Thr Thr Gln Asp Ile His Leu Gly Val Asn Glu Ser Leu Thr
145                 150                 155                 160

Asp Thr Ala Arg Val Leu Ser Ser Met Ala Asp Ala Val Leu Ala Arg
                165                 170                 175

Val Tyr Lys Gln Ser Asp Leu Asp Thr Leu Ala Lys Glu Ala Ser Ile
            180                 185                 190

Pro Ile Ile Asn Gly Leu Ser Asp Leu Tyr His Pro Ile Gln Ile Leu
        195                 200                 205

Ala Asp Tyr Leu Thr Leu Gln Glu His Tyr Ser Ser Leu Lys Gly Leu
    210                 215                 220

Thr Leu Ser Trp Ile Gly Asp Gly Asn Asn Ile Leu His Ser Ile Met
225                 230                 235                 240

Met Ser Ala Ala Lys Phe Gly Met His Leu Gln Ala Ala Thr Pro Lys
                245                 250                 255

Gly Tyr Glu Pro Asp Ala Ser Val Thr Lys Leu Ala Glu Gln Tyr Ala
            260                 265                 270

Lys Glu Asn Gly Thr Lys Leu Leu Leu Thr Asn Asp Pro Leu Glu Ala
        275                 280                 285

Ala His Gly Gly Asn Val Leu Ile Thr Asp Thr Trp Ile Ser Met Gly
    290                 295                 300

Gln Glu Glu Glu Lys Lys Lys Arg Leu Gln Ala Phe Gln Gly Tyr Gln
305                 310                 315                 320

Val Thr Met Lys Thr Ala Lys Val Ala Ala Ser Asp Trp Thr Phe Leu
                325                 330                 335

His Cys Leu Pro Arg Lys Pro Glu Glu Val Asp Asp Glu Val Phe Tyr
            340                 345                 350

Ser Pro Arg Ser Leu Val Phe Pro Glu Ala Glu Asn Arg Lys Trp Thr
        355                 360                 365

Ile Met Ala Val Met Val Ser Leu Leu Thr Asp Tyr Ser Pro Gln Leu
    370                 375                 380

Gln Lys Pro Lys Phe
385

<210> SEQ ID NO 48
<211> LENGTH: 362
<212> TYPE: PRT
<213> ORGANISM: Artificial Sequence
<220> FEATURE:
<223> OTHER INFORMATION: TAT-MTS(otc)-OTC delta linker

<400> SEQUENCE: 48

Arg Lys Lys Arg Arg Gln Arg Arg Leu Phe Asn Leu Arg Ile Leu
1               5                   10                  15

Leu Asn Asn Ala Ala Phe Arg Asn Gly His Asn Phe Met Val Arg Asn
            20                  25                  30

Phe Arg Cys Gly Gln Pro Leu Gln Asn Lys Val Gln Leu Lys Gly Arg
        35                  40                  45
```

Asp Leu Leu Thr Leu Arg Asn Phe Thr Gly Glu Glu Ile Lys Tyr Met
            50                  55                  60

Leu Trp Leu Ser Ala Asp Leu Lys Phe Arg Ile Lys Gln Lys Gly Glu
 65                  70                  75                  80

Tyr Leu Pro Leu Leu Gln Gly Lys Ser Leu Gly Met Ile Phe Glu Lys
                 85                  90                  95

Arg Ser Thr Arg Thr Arg Leu Ser Thr Glu Thr Gly Phe Ala Leu Leu
            100                 105                 110

Gly Gly His Pro Cys Phe Leu Thr Thr Gln Asp Ile His Leu Gly Val
            115                 120                 125

Asn Glu Ser Leu Thr Asp Thr Ala Arg Val Leu Ser Ser Met Ala Asp
            130                 135                 140

Ala Val Leu Ala Arg Val Tyr Lys Gln Ser Asp Leu Asp Thr Leu Ala
145                 150                 155                 160

Lys Glu Ala Ser Ile Pro Ile Ile Asn Gly Leu Ser Asp Leu Tyr His
                165                 170                 175

Pro Ile Gln Ile Leu Ala Asp Tyr Leu Thr Leu Gln Glu His Tyr Ser
            180                 185                 190

Ser Leu Lys Gly Leu Thr Leu Ser Trp Ile Gly Asp Gly Asn Asn Ile
            195                 200                 205

Leu His Ser Ile Met Met Ser Ala Ala Lys Phe Gly Met His Leu Gln
210                 215                 220

Ala Ala Thr Pro Lys Gly Tyr Glu Pro Asp Ala Ser Val Thr Lys Leu
225                 230                 235                 240

Ala Glu Gln Tyr Ala Lys Glu Asn Gly Thr Lys Leu Leu Leu Thr Asn
                245                 250                 255

Asp Pro Leu Glu Ala Ala His Gly Gly Asn Val Leu Ile Thr Asp Thr
            260                 265                 270

Trp Ile Ser Met Gly Gln Glu Glu Lys Lys Lys Arg Leu Gln Ala
            275                 280                 285

Phe Gln Gly Tyr Gln Val Thr Met Lys Thr Ala Lys Val Ala Ala Ser
290                 295                 300

Asp Trp Thr Phe Leu His Cys Leu Pro Arg Lys Pro Glu Glu Val Asp
305                 310                 315                 320

Asp Glu Val Phe Tyr Ser Pro Arg Ser Leu Val Phe Pro Glu Ala Glu
                325                 330                 335

Asn Arg Lys Trp Thr Ile Met Ala Val Met Val Ser Leu Leu Thr Asp
            340                 345                 350

Tyr Ser Pro Gln Leu Gln Lys Pro Lys Phe
            355                 360

<210> SEQ ID NO 49
<211> LENGTH: 360
<212> TYPE: PRT
<213> ORGANISM: Artificial Sequence
<220> FEATURE:
<223> OTHER INFORMATION: TAT-MTS(cs)-OTC

<400> SEQUENCE: 49

Met Arg Lys Lys Arg Arg Gln Arg Arg Gly Ser Asp Pro Ala Leu
 1               5                  10                  15

Leu Thr Ala Ala Ala Arg Leu Leu Gly Thr Lys Asn Ala Ser Cys Leu
                 20                  25                  30

Val Leu Ala Ala Arg His Ala Ser Glu Phe Leu Lys Gly Arg Asp Leu
            35                  40                  45

```
Leu Thr Leu Arg Asn Phe Thr Gly Glu Glu Ile Lys Tyr Met Leu Trp
 50                  55                  60

Leu Ser Ala Asp Leu Lys Phe Arg Ile Lys Gln Lys Gly Glu Tyr Leu
 65                  70                  75                  80

Pro Leu Gln Gly Lys Ser Leu Gly Met Ile Phe Glu Lys Arg Ser
                 85                  90                  95

Thr Arg Thr Arg Leu Ser Thr Glu Thr Gly Phe Ala Leu Leu Gly Gly
                100                 105                 110

His Pro Cys Phe Leu Thr Thr Gln Asp Ile His Leu Gly Val Asn Glu
                115                 120                 125

Ser Leu Thr Asp Thr Ala Arg Val Leu Ser Ser Met Ala Asp Ala Val
                130                 135                 140

Leu Ala Arg Val Tyr Lys Gln Ser Asp Leu Asp Thr Leu Ala Lys Glu
145                 150                 155                 160

Ala Ser Ile Pro Ile Ile Asn Gly Leu Ser Asp Leu Tyr His Pro Ile
                165                 170                 175

Gln Ile Leu Ala Asp Tyr Leu Thr Leu Gln Glu His Tyr Ser Ser Leu
                180                 185                 190

Lys Gly Leu Thr Leu Ser Trp Ile Gly Asp Gly Asn Asn Ile Leu His
                195                 200                 205

Ser Ile Met Met Ser Ala Ala Lys Phe Gly Met His Leu Gln Ala Ala
210                 215                 220

Thr Pro Lys Gly Tyr Glu Pro Asp Ala Ser Val Thr Lys Leu Ala Glu
225                 230                 235                 240

Gln Tyr Ala Lys Glu Asn Gly Thr Lys Leu Leu Leu Thr Asn Asp Pro
                245                 250                 255

Leu Glu Ala Ala His Gly Gly Asn Val Leu Ile Thr Asp Thr Trp Ile
                260                 265                 270

Ser Met Gly Gln Glu Glu Glu Lys Lys Lys Arg Leu Gln Ala Phe Gln
                275                 280                 285

Gly Tyr Gln Val Thr Met Lys Thr Ala Lys Val Ala Ala Ser Asp Trp
                290                 295                 300

Thr Phe Leu His Cys Leu Pro Arg Lys Pro Glu Glu Val Asp Asp Glu
305                 310                 315                 320

Val Phe Tyr Ser Pro Arg Ser Leu Val Phe Pro Glu Ala Glu Asn Arg
                325                 330                 335

Lys Trp Thr Ile Met Ala Val Met Val Ser Leu Leu Thr Asp Tyr Ser
                340                 345                 350

Pro Gln Leu Gln Lys Pro Lys Phe
                355                 360

<210> SEQ ID NO 50
<211> LENGTH: 368
<212> TYPE: PRT
<213> ORGANISM: Artificial Sequence
<220> FEATURE:
<223> OTHER INFORMATION: TAT-MTS(orf)-OTC

<400> SEQUENCE: 50

Met Arg Lys Lys Arg Arg Gln Arg Arg Gly Ser Asp Pro Gly Ala
 1               5                  10                  15

Leu Val Ile Arg Gly Ile Arg Asn Phe Asn Leu Glu Asn Arg Ala Glu
                 20                  25                  30

Arg Glu Ile Ser Lys Met Lys Pro Ser Val Ala Pro His Pro Ser
                 35                  40                  45
```

```
Glu Phe Leu Lys Gly Arg Asp Leu Leu Thr Leu Arg Asn Phe Thr Gly
         50                  55                  60

Glu Glu Ile Lys Tyr Met Leu Trp Leu Ser Ala Asp Leu Lys Phe Arg
 65                  70                  75                  80

Ile Lys Gln Lys Gly Glu Tyr Leu Pro Leu Leu Gln Gly Lys Ser Leu
                 85                  90                  95

Gly Met Ile Phe Glu Lys Arg Ser Thr Arg Thr Arg Leu Ser Thr Glu
            100                 105                 110

Thr Gly Phe Ala Leu Leu Gly Gly His Pro Cys Phe Leu Thr Thr Gln
            115                 120                 125

Asp Ile His Leu Gly Val Asn Glu Ser Leu Thr Asp Thr Ala Arg Val
            130                 135                 140

Leu Ser Ser Met Ala Asp Ala Val Leu Ala Arg Val Tyr Lys Gln Ser
145                 150                 155                 160

Asp Leu Asp Thr Leu Ala Lys Glu Ala Ser Ile Pro Ile Ile Asn Gly
                165                 170                 175

Leu Ser Asp Leu Tyr His Pro Ile Gln Ile Leu Ala Asp Tyr Leu Thr
            180                 185                 190

Leu Gln Glu His Tyr Ser Ser Leu Lys Gly Leu Thr Leu Ser Trp Ile
            195                 200                 205

Gly Asp Gly Asn Asn Ile Leu His Ser Ile Met Met Ser Ala Ala Lys
210                 215                 220

Phe Gly Met His Leu Gln Ala Ala Thr Pro Lys Gly Tyr Glu Pro Asp
225                 230                 235                 240

Ala Ser Val Thr Lys Leu Ala Glu Gln Tyr Ala Lys Glu Asn Gly Thr
                245                 250                 255

Lys Leu Leu Leu Thr Asn Asp Pro Leu Glu Ala His Gly Gly Asn
            260                 265                 270

Val Leu Ile Thr Asp Thr Trp Ile Ser Met Gly Gln Glu Glu Glu Lys
            275                 280                 285

Lys Lys Arg Leu Gln Ala Phe Gln Gly Tyr Gln Val Thr Met Lys Thr
            290                 295                 300

Ala Lys Val Ala Ala Ser Asp Trp Thr Phe Leu His Cys Leu Pro Arg
305                 310                 315                 320

Lys Pro Glu Glu Val Asp Asp Glu Val Phe Tyr Ser Pro Arg Ser Leu
                325                 330                 335

Val Phe Pro Glu Ala Glu Asn Arg Lys Trp Thr Ile Met Ala Val Met
            340                 345                 350

Val Ser Leu Leu Thr Asp Tyr Ser Pro Gln Leu Gln Lys Pro Lys Phe
355                 360                 365

<210> SEQ ID NO 51
<211> LENGTH: 369
<212> TYPE: PRT
<213> ORGANISM: Artificial Sequence
<220> FEATURE:
<223> OTHER INFORMATION: TAT-MTS(1ad)-OTC

<400> SEQUENCE: 51

Met Arg Lys Lys Arg Arg Gln Arg Arg Gly Ser Asp Pro Gln Ser
1               5                   10                  15

Trp Ser Arg Val Tyr Cys Ser Leu Ala Lys Arg Gly His Phe Asn Arg
            20                  25                  30

Ile Ser His Gly Leu Gln Gly Leu Ser Ala Val Pro Leu Arg Thr Tyr
        35                  40                  45
```

Ala Glu Phe Leu Lys Gly Arg Asp Leu Leu Thr Leu Arg Asn Phe Thr
            50                  55                  60

Gly Glu Glu Ile Lys Tyr Met Leu Trp Leu Ser Ala Asp Leu Lys Phe
 65                  70                  75                  80

Arg Ile Lys Gln Lys Gly Glu Tyr Leu Pro Leu Leu Gln Gly Lys Ser
                 85                  90                  95

Leu Gly Met Ile Phe Glu Lys Arg Ser Thr Arg Thr Arg Leu Ser Thr
            100                 105                 110

Glu Thr Gly Phe Ala Leu Leu Gly Gly His Pro Cys Phe Leu Thr Thr
            115                 120                 125

Gln Asp Ile His Leu Gly Val Asn Glu Ser Leu Thr Asp Thr Ala Arg
            130                 135                 140

Val Leu Ser Ser Met Ala Asp Ala Val Leu Ala Arg Val Tyr Lys Gln
145                 150                 155                 160

Ser Asp Leu Asp Thr Leu Ala Lys Glu Ala Ser Ile Pro Ile Ile Asn
                165                 170                 175

Gly Leu Ser Asp Leu Tyr His Pro Ile Gln Ile Leu Ala Asp Tyr Leu
            180                 185                 190

Thr Leu Gln Glu His Tyr Ser Ser Leu Lys Gly Leu Thr Leu Ser Trp
            195                 200                 205

Ile Gly Asp Gly Asn Asn Ile Leu His Ser Ile Met Met Ser Ala Ala
            210                 215                 220

Lys Phe Gly Met His Leu Gln Ala Ala Thr Pro Lys Gly Tyr Glu Pro
225                 230                 235                 240

Asp Ala Ser Val Thr Lys Leu Ala Glu Gln Tyr Ala Lys Glu Asn Gly
                245                 250                 255

Thr Lys Leu Leu Leu Thr Asn Asp Pro Leu Glu Ala Ala His Gly Gly
            260                 265                 270

Asn Val Leu Ile Thr Asp Thr Trp Ile Ser Met Gly Gln Glu Glu Glu
            275                 280                 285

Lys Lys Lys Arg Leu Gln Ala Phe Gln Gly Tyr Gln Val Thr Met Lys
290                 295                 300

Thr Ala Lys Val Ala Ala Ser Asp Trp Thr Phe Leu His Cys Leu Pro
305                 310                 315                 320

Arg Lys Pro Glu Glu Val Asp Asp Glu Val Phe Tyr Ser Pro Arg Ser
                325                 330                 335

Leu Val Phe Pro Glu Ala Glu Asn Arg Lys Trp Thr Ile Met Ala Val
            340                 345                 350

Met Val Ser Leu Leu Thr Asp Tyr Ser Pro Gln Leu Gln Lys Pro Lys
            355                 360                 365

Phe

<210> SEQ ID NO 52
<211> LENGTH: 356
<212> TYPE: PRT
<213> ORGANISM: Artificial Sequence
<220> FEATURE:
<223> OTHER INFORMATION: TAT-MTS(cs)-OTC delta linker

<400> SEQUENCE: 52

Met Arg Lys Lys Arg Arg Gln Arg Arg Arg Ala Leu Leu Thr Ala Ala
 1               5                  10                  15

Ala Arg Leu Leu Gly Thr Lys Asn Ala Ser Cys Leu Val Leu Ala Ala
             20                  25                  30

```
Arg His Ala Ser Glu Phe Leu Lys Gly Arg Asp Leu Thr Leu Arg
         35                  40                  45

Asn Phe Thr Gly Glu Glu Ile Lys Tyr Met Leu Trp Leu Ser Ala Asp
 50                  55                  60

Leu Lys Phe Arg Ile Lys Gln Lys Gly Glu Tyr Leu Pro Leu Leu Gln
 65                  70                  75                  80

Gly Lys Ser Leu Gly Met Ile Phe Glu Lys Arg Ser Thr Arg Thr Arg
                 85                  90                  95

Leu Ser Thr Glu Thr Gly Phe Ala Leu Leu Gly His Pro Cys Phe
                100                 105                 110

Leu Thr Thr Gln Asp Ile His Leu Gly Val Asn Glu Ser Leu Thr Asp
                115                 120                 125

Thr Ala Arg Val Leu Ser Ser Met Ala Asp Ala Val Leu Ala Arg Val
130                 135                 140

Tyr Lys Gln Ser Asp Leu Asp Thr Leu Ala Lys Glu Ala Ser Ile Pro
145                 150                 155                 160

Ile Ile Asn Gly Leu Ser Asp Leu Tyr His Pro Ile Gln Ile Leu Ala
                165                 170                 175

Asp Tyr Leu Thr Leu Gln Glu His Tyr Ser Ser Leu Lys Gly Leu Thr
                180                 185                 190

Leu Ser Trp Ile Gly Asp Gly Asn Asn Ile Leu His Ser Ile Met Met
            195                 200                 205

Ser Ala Ala Lys Phe Gly Met His Leu Gln Ala Ala Thr Pro Lys Gly
        210                 215                 220

Tyr Glu Pro Asp Ala Ser Val Thr Lys Leu Ala Glu Gln Tyr Ala Lys
225                 230                 235                 240

Glu Asn Gly Thr Lys Leu Leu Leu Thr Asn Asp Pro Leu Glu Ala Ala
                245                 250                 255

His Gly Gly Asn Val Leu Ile Thr Asp Thr Trp Ile Ser Met Gly Gln
                260                 265                 270

Glu Glu Glu Lys Lys Lys Arg Leu Gln Ala Phe Gln Gly Tyr Gln Val
            275                 280                 285

Thr Met Lys Thr Ala Lys Val Ala Ala Ser Asp Trp Thr Phe Leu His
    290                 295                 300

Cys Leu Pro Arg Lys Pro Glu Glu Val Asp Asp Glu Val Phe Tyr Ser
305                 310                 315                 320

Pro Arg Ser Leu Val Phe Pro Glu Ala Glu Asn Arg Lys Trp Thr Ile
                325                 330                 335

Met Ala Val Met Val Ser Leu Leu Thr Asp Tyr Ser Pro Gln Leu Gln
                340                 345                 350

Lys Pro Lys Phe
        355

<210> SEQ ID NO 53
<211> LENGTH: 364
<212> TYPE: PRT
<213> ORGANISM: Artificial Sequence
<220> FEATURE:
<223> OTHER INFORMATION: TAT-MTS(orf)-OTC delta linker

<400> SEQUENCE: 53

Met Arg Lys Lys Arg Gln Arg Arg Gly Ala Leu Val Ile Arg
 1               5                  10                  15

Gly Ile Arg Asn Phe Asn Leu Glu Asn Arg Ala Glu Arg Glu Ile Ser
                 20                  25                  30
```

```
Lys Met Lys Pro Ser Val Ala Pro Arg His Pro Ser Glu Phe Leu Lys
         35                  40                  45

Gly Arg Asp Leu Leu Thr Leu Arg Asn Phe Thr Gly Glu Glu Ile Lys
 50                  55                  60

Tyr Met Leu Trp Leu Ser Ala Asp Leu Lys Phe Arg Ile Lys Gln Lys
 65                  70                  75                  80

Gly Glu Tyr Leu Pro Leu Leu Gln Gly Lys Ser Leu Gly Met Ile Phe
                 85                  90                  95

Glu Lys Arg Ser Thr Arg Thr Arg Leu Ser Thr Glu Thr Gly Phe Ala
            100                 105                 110

Leu Leu Gly Gly His Pro Cys Phe Leu Thr Thr Gln Asp Ile His Leu
        115                 120                 125

Gly Val Asn Glu Ser Leu Thr Asp Thr Ala Arg Val Leu Ser Ser Met
130                 135                 140

Ala Asp Ala Val Leu Ala Arg Val Tyr Lys Gln Ser Asp Leu Asp Thr
145                 150                 155                 160

Leu Ala Lys Glu Ala Ser Ile Pro Ile Ile Asn Gly Leu Ser Asp Leu
                165                 170                 175

Tyr His Pro Ile Gln Ile Leu Ala Asp Tyr Leu Thr Leu Gln Glu His
            180                 185                 190

Tyr Ser Ser Leu Lys Gly Leu Thr Leu Ser Trp Ile Gly Asp Gly Asn
        195                 200                 205

Asn Ile Leu His Ser Ile Met Met Ser Ala Ala Lys Phe Gly Met His
210                 215                 220

Leu Gln Ala Ala Thr Pro Lys Gly Tyr Glu Pro Asp Ala Ser Val Thr
225                 230                 235                 240

Lys Leu Ala Glu Gln Tyr Ala Lys Glu Asn Gly Thr Lys Leu Leu Leu
                245                 250                 255

Thr Asn Asp Pro Leu Glu Ala Ala His Gly Gly Asn Val Leu Ile Thr
            260                 265                 270

Asp Thr Trp Ile Ser Met Gly Gln Glu Glu Lys Lys Lys Arg Leu
        275                 280                 285

Gln Ala Phe Gln Gly Tyr Gln Val Thr Met Lys Thr Ala Lys Val Ala
290                 295                 300

Ala Ser Asp Trp Thr Phe Leu His Cys Leu Pro Arg Lys Pro Glu Glu
305                 310                 315                 320

Val Asp Asp Glu Val Phe Tyr Ser Pro Arg Ser Leu Val Phe Pro Glu
                325                 330                 335

Ala Glu Asn Arg Lys Trp Thr Ile Met Ala Val Met Val Ser Leu Leu
            340                 345                 350

Thr Asp Tyr Ser Pro Gln Leu Gln Lys Pro Lys Phe
        355                 360

<210> SEQ ID NO 54
<211> LENGTH: 365
<212> TYPE: PRT
<213> ORGANISM: Artificial Sequence
<220> FEATURE:
<223> OTHER INFORMATION: TAT-MTS(lad)-OTC delta linker

<400> SEQUENCE: 54

Met Arg Lys Lys Arg Arg Gln Arg Arg Gln Ser Trp Ser Arg Val
 1               5                  10                  15

Tyr Cys Ser Leu Ala Lys Arg Gly His Phe Asn Arg Ile Ser His Gly
                 20                  25                  30
```

-continued

```
Leu Gln Gly Leu Ser Ala Val Pro Leu Arg Thr Tyr Ala Glu Phe Leu
            35                  40                  45
Lys Gly Arg Asp Leu Leu Thr Leu Arg Asn Phe Thr Gly Glu Glu Ile
 50                  55                  60
Lys Tyr Met Leu Trp Leu Ser Ala Asp Leu Lys Phe Arg Ile Lys Gln
 65                  70                  75                  80
Lys Gly Glu Tyr Leu Pro Leu Leu Gln Gly Lys Ser Leu Gly Met Ile
            85                  90                  95
Phe Glu Lys Arg Ser Thr Arg Thr Arg Leu Ser Thr Glu Thr Gly Phe
            100                 105                 110
Ala Leu Leu Gly Gly His Pro Cys Phe Leu Thr Thr Gln Asp Ile His
            115                 120                 125
Leu Gly Val Asn Glu Ser Leu Thr Asp Thr Ala Arg Val Leu Ser Ser
            130                 135                 140
Met Ala Asp Ala Val Leu Ala Arg Val Tyr Lys Gln Ser Asp Leu Asp
145                 150                 155                 160
Thr Leu Ala Lys Glu Ala Ser Ile Pro Ile Ile Asn Gly Leu Ser Asp
                165                 170                 175
Leu Tyr His Pro Ile Gln Ile Leu Ala Asp Tyr Leu Thr Leu Gln Glu
            180                 185                 190
His Tyr Ser Ser Leu Lys Gly Leu Thr Leu Ser Trp Ile Gly Asp Gly
            195                 200                 205
Asn Asn Ile Leu His Ser Ile Met Met Ser Ala Ala Lys Phe Gly Met
            210                 215                 220
His Leu Gln Ala Ala Thr Pro Lys Gly Tyr Glu Pro Asp Ala Ser Val
225                 230                 235                 240
Thr Lys Leu Ala Glu Gln Tyr Ala Lys Glu Asn Gly Thr Lys Leu Leu
                245                 250                 255
Leu Thr Asn Asp Pro Leu Glu Ala Ala His Gly Gly Asn Val Leu Ile
            260                 265                 270
Thr Asp Thr Trp Ile Ser Met Gly Gln Glu Glu Glu Lys Lys Lys Arg
            275                 280                 285
Leu Gln Ala Phe Gln Gly Tyr Gln Val Thr Met Lys Thr Ala Lys Val
            290                 295                 300
Ala Ala Ser Asp Trp Thr Phe Leu His Cys Leu Pro Arg Lys Pro Glu
305                 310                 315                 320
Glu Val Asp Asp Glu Val Phe Tyr Ser Pro Arg Ser Leu Val Phe Pro
                325                 330                 335
Glu Ala Glu Asn Arg Lys Trp Thr Ile Met Ala Val Met Val Ser Leu
                340                 345                 350
Leu Thr Asp Tyr Ser Pro Gln Leu Gln Lys Pro Lys Phe
            355                 360                 365
```